US006800443B2

(12) United States Patent
Ford et al.

(10) Patent No.: US 6,800,443 B2
(45) Date of Patent: Oct. 5, 2004

(54) METHOD OF DETECTING A CANCEROUS CELL EXPRESSING AN EGF MOTIF POLYNUCLEOTIDE

(75) Inventors: John E. Ford, San Diego, CA (US); George Yeung, Mountain View, CA (US); Hua Zhou, Santa Clara, CA (US)

(73) Assignee: Nuvelo, Inc., Sunnyvale, CA (US)

( * ) Notice: Subject to any disclaimer, the term of this patent is extended or adjusted under 35 U.S.C. 154(b) by 70 days.

(21) Appl. No.: 10/136,227

(22) Filed: May 1, 2002

(65) Prior Publication Data

US 2003/0165886 A1 Sep. 4, 2003

Related U.S. Application Data

(63) Continuation of application No. 09/981,649, filed on Oct. 15, 2001, which is a continuation-in-part of application No. 09/687,860, filed on Oct. 13, 2000, which is a continuation-in-part of application No. 09/363,316, filed on Jul. 28, 1999, now Pat. No. 6,392,019, which is a continuation-in-part of application No. 09/249,697, filed on Feb. 12, 1999, now Pat. No. 6,392,018, which is a continuation-in-part of application No. 08/968,800, filed on Nov. 22, 1997, now abandoned.

(51) Int. Cl.[7] .......................... C12Q 1/68; C07H 21/04; G01N 33/53

(52) U.S. Cl. .......................... 435/6; 536/23.1; 536/23.5; 536/24.31; 436/501

(58) Field of Search .......................... 435/4, 6; 536/23.1, 536/23.5, 24.3, 24.31; 436/501, 504

(56) References Cited

U.S. PATENT DOCUMENTS

| | | | | |
|---|---|---|---|---|
| 5,194,596 A | | 3/1993 | Tischer et al. | 530/399 |
| 6,392,018 B1 | * | 5/2002 | Ford et al. | 530/351 |
| 6,392,019 B1 | * | 5/2002 | Ford et al. | 530/387.9 |

FOREIGN PATENT DOCUMENTS

| | | |
|---|---|---|
| WO | WO 92/19734 | 11/1992 |
| WO | WO 99/06553 | 2/1999 |
| WO | WO 99/46281 | 9/1999 |
| WO | WO 00/37638 | 6/2000 |
| WO | WO 00/39284 | 7/2000 |

OTHER PUBLICATIONS

Konety et al. Urine based markers of urological malignancies. J Urology 165: 600–611, 2001.*

Skolnick et al. From genes to protein structure and function: novel applications of computational approaches in the genomic era. Trends in Biotech 18(1): 34–39, 2000.*

Bork, A. Powers and pitfalls in sequence analysis: the 70% hurdle. Genome Res 10: 398–400, 2000.*

Doerks et al. Protein annotation: detective work for function prediction. Trends in Genetics 14(6): 248–250, 1998.*

Smith et al. The challenges of genome sequence annotation or "The devil is in the details". Nature Biotech 15: 1222–1223, 1997.*

Brenner, S.E. Errors in genome function. Trends in Genetics 15(4): 132–133, 1999.*

Bork et al. Go hunting in sequence databases but watch out for the traps. Trends in Genetics. 12(10): 425–427, 1996.*

Wells. J.A. Additivity of mutational effects in proteins. Biochemistry 29 (37): 8509–8517, 1990.*

Ngo et al. Computational complexity, protein structure prediction, and the Levinthal paradox. The Protein Folding Problem and Tertiary Structure Prediction, pp. 492–495, 1994.*

Yeung et al. Cloning of a novel epidermal growth factor repeat containing gene EGFL6: expressed in tumor and fetal tissues.*

McKnight et al., EGF–TM7: a novel subfamily of seven–transmembrane–region leukocyte cell–surface molecules, Immunology Today; 17(6): 283–287 (Jun. 1996).

Genebank Accession No.: R99817, yq69bll.rl Soares fetal liver spleen 1NFLS *Homo sapiens* cDNA clone IMAGE: 201021 5' similar to SP:FBN1 HUMAN 35555 FIBRILLIN 1, mRNA sequence, deposited by Hillier et al., dated Sep. 14, 1995.

Genebank Accession No.: AA025649, ze85d03.rl Soares fetal heart NbHH19W *Homo sapiens* cDNA clone IMAGE:365765 5', mRNA sequence, deposited by Hillier et al., dated Aug. 14, 1996.

Genebank Accession No.: AA 436507, zv08c07.rl Soares NhHMPu$_{S1}$ *Homo sapiens* cDNA clone IMAGE: 753036 5', mRNA sequence, deposited by Hillier et al., dated May 30, 1997.

Cunningham & Wells, High–Resolution Eptiope Mapping of hGH–Receptor Interactions by Alanine–Scanning Mutagenesis, Science 244: 1081–1085 (Jun. 2, 1989).

Selander et al. H. NMR Assignment and Secondary Structure of the $Ca^{2+}$–Free Form of the Amino–Terminal Epidermal Growth Factor like Domain in Coagulation Factor X, Biochemistry 29: 8111–8118 (1990).

Graves et al., Insight into E–selection/ligand Interaction from the Crystal Structure and Mutagenesis of the lec/EGF Domains, Nature 367: 532–538 (Feb. 10, 1994).

Davis, The Many Faces of Epidermal Growth Factor Repeats, The New Biologist 2(5): 410–419 (May 1990).

Connelly & Hegele, Hepatic Lipase Deficiency, Clin. Reviews in Clin. Lab. Sciences 35(6): 547–572 (1998).

Guadiz et al., Thrombin Cleavage–Independent Deposition of Fibrinogen in Extracellular Matrices, Blood 90(7): 2644–2653 (Oct. 1, 1997).

(List continued on next page.)

*Primary Examiner*—Elizabeth Kemmerer
*Assistant Examiner*—Bridget E. Bunner
(74) *Attorney, Agent, or Firm*—Renee S. Polizotto

(57) ABSTRACT

The present invention provides novel polynucleotides and proteins encoded by such polynucleotides, along with therapeutic, diagnostic and research utilities for these polynucleotides and proteins. In particular, the polypeptides of the invention are useful for detecting cancers.

3 Claims, 5 Drawing Sheets

OTHER PUBLICATIONS

Figure 5:
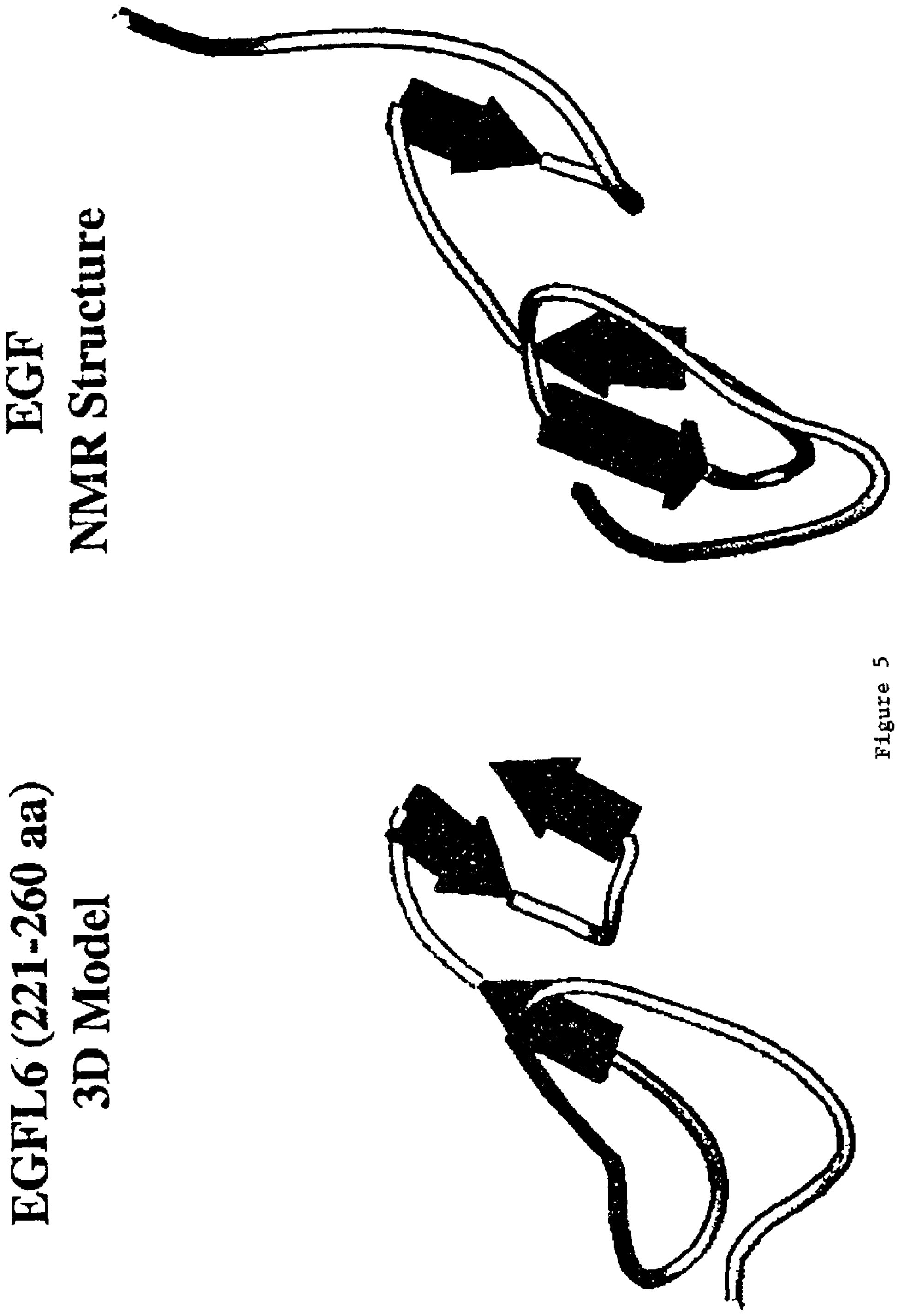

Boukerche et al., Thrombospondin Modulates Melanoma—Platelet Interactions and Melanoma Tumour Cell Growth in vivo, British Journal of Cancer 72: 108–116 (1995).

West et al., Correlation of Vascular Endothelial Growth Factor Expression with Fibroblast Growth Factor–8 Expression and Clinico–Pathologic Parameters in Human Prostate Cancer, British Journal of Cancer 85(4): 576–583 (2001).

Riedel et al., Immunocytochemical Localization of Basic Fibroblast Growth Factor in Squamous Cell Carcinomas of the Head and Neck, Anticancer Research 27: 1873–1878 (2001).

Chan et al., Prostate–Specific Antigen as a Marker for Prostatic Cancer: a Monoclonal and a Polyclonal Immunoassay Compared, Clinical Chemistry 33(10): 1916–1920 (1987).

Hayes et al., Circulating Her–2/erbB–2/c–neu (HER–2) Extracellular Domain as a Prognostic Factor in Patients with Metastatic Breast Cancer: Cancer and Leukemia Group B Study 8662, Clinical Cancer Research vol. 7: 2703–2711 (Sep. 2001).

Lissoni et al., The Biological Significance of Soluble Interleukin–2 Receptors in Solid Tumors, Eur J. Cancer 26(1): 33–36 (1990).

* cited by examiner

```
Notch(C)     IDEC-SNP   CQNGGTC---D-VGSY-C-CPPGFT   GK---CE-N

10244(C)     -NECTM---  CQH---C  VNT-GSY-CKC-SG--   G--L-C   D
80                                       CRCFPGYT   GKT  CSQ D
95           VNECGMKPRP CQHR  C  VNTHGSYKCFCLS      GHMLMP   D
133          VNSRTCAMIN CQYS  C  EDTEEGPQCLCPSS     GLRLAPN
175          IDECASGKVI CPYNRRC  VNTFGSYYCKCHIGFE   LQYISGR
220          INECTMDSHT CSHHANC  FNTQGSF CKCKQGYK   GNGRLCS

CD97(C)      V-EC-SG-Q--C-SS--C  -NTVGSY-CRCRPGW-P-PG-PN---   D

EGF(C)      NSDSECPLSHDGYCLHDGVCMYIEALDKYACNCVVGYI---GER--CQYRDLKWWELR
```

Figure 1

GGCTGGAGAA GAAACAGCAA GGGAGTCTGT GAAGCTACAT GCGAACCTGG
ATGTAAGTTT GGTGAGTGCG TGGGACCAAA CAAATGCAGA TGCTTTCCAG
GATACACCGG GAAAACCTGC AGTCAAGATG TGAATGAGTG TGGAATGAAA
CCCCGGCCAT GCCAACACAG ATGTGTGAAT ACACACGGAA GCTACAAGTG
CTTTTGCCTC AGTGGCCACA TGCTCATGCC AGATGCTACG TGTGTGAACT
CNAGGACATG TGCCATGATA AACTGTCAGT ATAGCTGTGA AGACACAGAA
SEQ ID NO: 1

GGCTGGAGAA GAAACAGCAA GGGAGTCTGT GAAGCTACAT GCGAACCTGG
ATGTAAGTTT GGTGAGTGCG TGGGACCAAA CAAATGCAGA TGCTTTCCAG
GATACACCGG GAAAACCTGC AGTCAAGATG TGAATGAGTG TGGAATGAAA
CCCCGGCCAT GCCAACACAG ATGTGTGAAT ACACACGGAA GCTACAAGTG
CTTTTGCCTC AGTGGCCACA TGCTCATGCC AGATGCTACG TGTGTGAACT
CNAGGACATG TGCCATGATA AACTGTCAGT ATAGCTGTGA AGACACAGAA
GAAGGGCCAC AGTGCCTGTG TCCATCCTCA GGACTCCGCC TGGCCCCAAA
TGGAAGAGAC TGTCTAGATA TTGATGAATG TGCCTCTGGT AAAGTCATCT
GTCCCTACAA TCGAAGATGT GTGAACACAT TTGGAAGCTA CTACTGCAAA
TGTCACATTG GTTTCGAACT GCAATATATC AGTGGACGAT ATGACTGTAT
AGATATAAAT GAATGTACTA TGGATAGCCA TACGTGCAGC CACCATGCCA
ATTGCTTCAA TACCCAAGGG TCCTTCAAGT GTAAATGCAA GCAGGGATAT
AAAGGCAATG GACTTCGGTG TTCTGCTATC CCTGAAAATT CTGTGAAGGA
AGTCCTCAGA GCACCTGGTA CCATCAAAGA CAGAATCAAG AAGTTGCTTG
CTCACAAAAA CAGCATGAAA AAGAAGGCAA AAATTAAAAA TGTTACCCCA
GAACCCACCA GGACTCCTAC CCCTAAGGTG AACTTGCAGC CCTTCAACTA
TGAAGAGATA GTTTCCAGAG GCGGGAACTC TCATGGAGGT AAAAAAGGGA
ATGAAGAGAA AATGAAAGAG GGGCTTGAGG ATGAGAAAAG AGAAGAGAAA
GCCCTGAAGA ATGACATAGA GGAGCGAAGC CTGCGAGGAG ATGTGTTTTT
CCCTAAGGTG AATGAAGCAG GTGAATTCGG CCTGATTCTG GTCCAAAGGA
AAGCGCTAAC TTCCAAACTG GAACATAAAG ATTTAAATAT CTCGGTTGAC
TGCAGCTTCA ATCATGGGAT CTGTGACTGG AAACAGGATA GAGAAGATGA
TTTTGACTGG AATCCTGCTG ATCGAGATAA TGCTATTGGC TTCTATATGG
CAGTTCCGGC CTTGGCAGGT CACATGAAAG ACATTGGCCG ATTGAAACTT
CTCCTACCTG ACCTGCAACC CCAAAGCAAC TTCTGTTTGC TCTTTGATTA
CCGGCTGGCC GGAGACAAAG TCGGGAAACT TCGAGTGTTT GTGAAAAACA
GTAACAATGC CCTGGCATGG GAGAAGACCA CGAGTGAGGA TGAAAAGTGG
AAGACAGGGA AAATTCAGTT GTATCAAGGA ACTGATGCTA CCAAAAGCAT
CATTTTTGAA GCAGAACGTG GCAAGGGCAA AACCGGCGAA ATCGCAGTGG
ATGGCGTCTT GCTTGTTTCA GGCTTATGTC CAGATAGCCT TTTATCTGTG
GANNNCTGAA TGGTACTATC TTTATATTTG ACTTTGTATG TCAGTTCCCT
GGTTTTTTTG ATATTGCATC ATAGGACCTC TGGCATTTTA AAATTACTAG
CTGAAAAATT G
SEQ ID NO: 2

FIGURE 2

GWRRNSKGVCEATCEPGCKFGECVGPNKCRCFPGYTGKTCSQDVNECGMKPRPCQHR
CVNTHGSYKCFCLSGHMLMPDATCVNSRTCAMINCQYSCEDTE
SEQ ID NO:3

GWRRNSKGVCEATCEPGCKFGECVGPNKCRCFPGYTGKTCSQDVNECGMKPRPCQHR
CVNTHGSYKCFCLSGHMLMPDATCVNSRTCAMINCQYSCEDTEEGPQCLCPSSGLRLAP
NGRDCLDIDECASGKVICPYNRRCVNTFGSYYCKCHIGFELQYISGRYDCIDINECTMDS
HTCSHHANCFNTQGSFKCKCKQGYKGNGLRCSAIPENSVKEVLRAPGTIKDRIKKLLAH
KNSMKKKAKIKNVTPEPTRTPTPKVNLQPFNYEEIVSRGGNSHGGKKGNEEKMKEGLE
DEKREEKALKNDIEERSLRGDVFFPKVNEAGEFGLILVQRKALTSKLEHKDLNISVDCSF
NHGICDWKQDREDDFDWNPADRDNAIGFYMAVPALAGHMKDIGRLKLLLPDLQPQSN
FCLLFDYRLAGDKVGKLRVFVKNSNNALAWEKTTSEDEKWKTGKIQLYQGTDATKSIIF
EAERGKGKTGEIAVDGVLLVSGLCPDSLLSVDDXMVLSLYLTLYVSSLVFLILHHRTSGI
LKLLAEKL
SEQ ID NO:4

FIGURE 3

ACTAGTGATTCCATCCTAATACGACTCACTATAGGGCTCGAGCGGCCGCCCGGGCAGGTCTGCAGGGACAGCACCCGGTA
ACTGCGAGTGGAGCGGAGGACCCGAGCGGCTGAGGAGAGAGGAGGCGGCGGCTTAGCTGCTACGGGGTCCGGCCGGCGCC
CTCCCGAGGGGGGCTCAGGAGGAGGAAGGAGGACCCGTGCGAGAATGCCTCTGCCCTGGAGCCTTGCGCTCCCGCTGCTG
CTCCCCTGGGTGGCAGGTGGTTTCGGGAACGCGGCCAGTGCAAGGCATCACGGGTTGTTAGCATCGGCACGTCAGCCTGG
GGTCTGTCACTATGGAACTAAACTGGCCTGCTGCTACGGCTGGAGAAGAAACAGCAAGGGAGTCTGTGAAGCTACATGCG
AACCTGGATGTAAGTTTGGTGAGTGCGTGGGACCAAACAAATGCAGATGCTTTCCAGGATACACCGGGAAAACCTGCAGT
CAAGATGTGAATGAGTGTGGAATGAAACCCCGGCCATGCCAACACAGATGTGTGAATACACACGGAAGCTACAAGTGCTT
TTGCCTCAGTGGCCACATGCTCATGCCAGATGCTACGTGTGTGAACTCTAGGACATGTGCCATGATAAACTGTCAGTATA
GCTGTGAAGACACAGAAGAAGGGCCACAGTGCCTGTGTCCATCCTCAGGACTCCGCCTGGCCCCAAATGGAAGAGACTGT
CTAGATATTGATGAATGTGCCTCTGGTAAAGTCATCTGTCCCTACAATCGAAGATGTGTGAACACATTTGGAAGCTACTA
CTGCAAATGTCACATTGGTTTCGAACTGCAATATATCAGTGGACGATATGACTGTATAGATATAAATGAATGTACTATGG
ATAGCCATACGTGCAGCCACCATGCCAATTGCTTCAATACCCAAGGGTCCTTCAAGTGTAAATGCAAGCAGGGATATAAA
GGCAATGGACTTCGGTGTTCTGCTATCCCTGAAAATTCTGTGAAGGAAGTCCTCAGAGCACCTGGTACCATCAAAGACAG
AATCAAGAAGTTGCTTGCTCACAAAAACAGCATGAAAAAGAAGGCAAAAATTAAAAATGTTACCCCAGAACCCACCAGGA
CTCCTACCCCTAAGGTGAACTTGCAGCCCTTCAACTATGAAGAGATAGTTTCCAGAGGCGGGAACTCTCATGGAGGTAAA
AAAGGGAATGAAGAGAAAATGAAAGAGGGGCTTGAGGATGAGAAAAGAGAAGAGAAAGCCCTGAAGAATGACWTAGAGGA
GCGAAGCCTGCGAGGAGATGTGTTTTTCCCTAAGGTGAATGAAGCAGGTGAATTCGGCCTGATTCTGGTCCAAACGAAAG
CGCTAACTTCCAAACTGGAACATAAAGATTTAAATATCTCGGTTGACTGCAGCTTCAATCATGGGATCTGTGACTGGAAA
CAGGATAGAGAAGATGATTTTGACTGGAATCCTGCTGATCGAGATAATGCTATTGGCTTCTATATGGCAGTTCCGGCCTT
GGCAGGTCACAAGAAAGACATTGGCCGATTGAAACTTCTCCTACCTGACCTGCAACCCCAAAGCAACTTCTGTTTGCTCT
TTGATTACCGGCTGGCCGGAGACAAAGTCGGGAAACTTCGAGTGTTTGTGAAAAACAGTAACAATGCCCTGGCATGGGAG
AAGACCACGAGTGAGGATGAAAAGTGGAAGACAGGGAAAATTCAGTTGTATCAAGGAACTGATGCTACCAAAAGCATCAT
TTTTGAAGCAGAACGTGGCAAGGGCAAAACCGGCGAAATCGCAGTGGATGGCGTCTTGCTTGTTTCAGGCTTATGTCCAG
ATAGCCTTTTATCTGTGGATGACTGAATGTTACTATCTTTATATTTGACTTTGTATGTCAGTTCCCTGGTTTTTTTGATA
TTGSATCATAGGACCTCTGGCATTTTAAAATTACTAAGCTGAAAAATTGTAATGTACCAACAGAAATTATTATTGTAAGA
TGCCTTTMTTGTATAAGATATGCCAATATTTGCTTTAAATATCATATCACTGTATCTTCTCAGTCATTTCTGAATCTTTC
CACATTATATTATAAAATATGGAAATGTCAGGTTTATCTCCCCTCCTCAGTATATCTGATTTGTATAAGTAAGTTGATGA
GCTTCTCTCTGCAACATTTCTAGAAAATAGAHAAAAAAGCACAGAGAAATGTTTAACTGTTTGACTCTTATGATAGTTTT
TGGAAACTATGACATCAAAGATAGACTTTTGCCTAAGTGGCTTAGCTGGGTCTTTCATAGCCAAACTTGTATATTTAAAT
TCTTTGTAATAATAATATCCAAATCATCAAAAAAAAAAAAAAAAA
SEQ ID NO:5

MPLPWSLALPLLLPWVAGGFGNAASARHHGLLASARQPGVCHYGTKLACCYGWRRNSKGVCEATCEPGCKFGECVGPNKC
RCFPGYTGKTCSQDVNECGMKPRPCQHRCVNTHGSYKCFCLSGHMLMPDATCVNSRTCAMINCQYSCEDTEEGPQCLCPS
SGLRLAPNGRDCLDIDECASGKVICPYNRRCVNTFGSYYCKCHIGFELQYISGRYDCIDINECTMDSHTCSHHANCFNTQ
GSFKCKCKQGYKGNGLRCSAIPENSVKEVLRAPGTIKDRIKKLLAHKNSMKKKAKIKNVTPEPTRTPTPKVNLQPFNYEE
IVSRGGNSHGGKKGNEEKMKEGLEDEKREEKALKNDXEERSLRGDVFFPKVNEAGEFGLILVQRKALTSKLEHKDLNISV
DCSFNHGICDWKQDREDDFDWNPADRDNAIGFYMAVPALAGHKKDIGRLKLLLPDLQPQSNFCLLFDYRLAGDKVGKLRV
FVKNSNNALAWEKTTSEDEKWKTGKIQLYQGTDATKSIIFEAERGKGKTGEIAVDGVLLVSGLCPDSLLSVDD
SEQ ID NO: 6

FIGURE 4

SEQUENCE LISTING

```
<160> NUMBER OF SEQ ID NOS: 32

<210> SEQ ID NO 1
<211> LENGTH: 300
<212> TYPE: DNA
<213> ORGANISM: Homo sapiens
<220> FEATURE:
<221> NAME/KEY: CDS
<222> LOCATION: (1)...(300)
<220> FEATURE:
<221> NAME/KEY: misc_feature
<222> LOCATION: (252)
<223> OTHER INFORMATION: n = A or T or C or G

<400> SEQUENCE: 1

ggc tgg aga aga aac agc aag gga gtc tgt gaa gct aca tgc gaa cct       48
Gly Trp Arg Arg Asn Ser Lys Gly Val Cys Glu Ala Thr Cys Glu Pro
 1               5                  10                  15

gga tgt aag ttt ggt gag tgc gtg gga cca aac aaa tgc aga tgc ttt       96
Gly Cys Lys Phe Gly Glu Cys Val Gly Pro Asn Lys Cys Arg Cys Phe
            20                  25                  30

cca gga tac acc ggg aaa acc tgc agt caa gat gtg aat gag tgt gga      144
Pro Gly Tyr Thr Gly Lys Thr Cys Ser Gln Asp Val Asn Glu Cys Gly
        35                  40                  45

atg aaa ccc cgg cca tgc caa cac aga tgt gtg aat aca cac gga agc      192
Met Lys Pro Arg Pro Cys Gln His Arg Cys Val Asn Thr His Gly Ser
    50                  55                  60

tac aag tgc ttt tgc ctc agt ggc cac atg ctc atg cca gat gct acg      240
Tyr Lys Cys Phe Cys Leu Ser Gly His Met Leu Met Pro Asp Ala Thr
 65                  70                  75                  80

tgt gtg aac tcn agg aca tgt gcc atg ata aac tgt cag tat agc tgt      288
Cys Val Asn Xaa Arg Thr Cys Ala Met Ile Asn Cys Gln Tyr Ser Cys
                85                  90                  95

gaa gac aca gaa                                                      300
Glu Asp Thr Glu
            100


<210> SEQ ID NO 2
<211> LENGTH: 1611
<212> TYPE: DNA
<213> ORGANISM: Homo sapiens
<220> FEATURE:
<221> NAME/KEY: CDS
<222> LOCATION: (1)...(1506)
<220> FEATURE:
<221> NAME/KEY: misc_feature
<222> LOCATION: (252)
<223> OTHER INFORMATION: n = A or T or C or G
<220> FEATURE:
<221> NAME/KEY: misc_feature
<222> LOCATION: (1503)
<223> OTHER INFORMATION: n = A or T or C or G
<220> FEATURE:
<221> NAME/KEY: misc_feature
<222> LOCATION: (1504)
<223> OTHER INFORMATION: n = A or T or C or G
<220> FEATURE:
<221> NAME/KEY: misc_feature
```

-continued

```
<222> LOCATION: (1505)
<223> OTHER INFORMATION: n = A or T or C or G

<400> SEQUENCE: 2

ggc tgg aga aga aac agc aag gga gtc tgt gaa gct aca tgc gaa cct      48
Gly Trp Arg Arg Asn Ser Lys Gly Val Cys Glu Ala Thr Cys Glu Pro
 1               5                  10                  15

gga tgt aag ttt ggt gag tgc gtg gga cca aac aaa tgc aga tgc ttt      96
Gly Cys Lys Phe Gly Glu Cys Val Gly Pro Asn Lys Cys Arg Cys Phe
            20                  25                  30

cca gga tac acc ggg aaa acc tgc agt caa gat gtg aat gag tgt gga     144
Pro Gly Tyr Thr Gly Lys Thr Cys Ser Gln Asp Val Asn Glu Cys Gly
        35                  40                  45

atg aaa ccc cgg cca tgc caa cac aga tgt gtg aat aca cac gga agc     192
Met Lys Pro Arg Pro Cys Gln His Arg Cys Val Asn Thr His Gly Ser
    50                  55                  60

tac aag tgc ttt tgc ctc agt ggc cac atg ctc atg cca gat gct acg     240
Tyr Lys Cys Phe Cys Leu Ser Gly His Met Leu Met Pro Asp Ala Thr
 65                  70                  75                  80

tgt gtg aac tcn agg aca tgt gcc atg ata aac tgt cag tat agc tgt     288
Cys Val Asn Xaa Arg Thr Cys Ala Met Ile Asn Cys Gln Tyr Ser Cys
                 85                  90                  95

gaa gac aca gaa gaa ggg cca cag tgc ctg tgt cca tcc tca gga ctc     336
Glu Asp Thr Glu Glu Gly Pro Gln Cys Leu Cys Pro Ser Ser Gly Leu
            100                 105                 110

cgc ctg gcc cca aat gga aga gac tgt cta gat att gat gaa tgt gcc     384
Arg Leu Ala Pro Asn Gly Arg Asp Cys Leu Asp Ile Asp Glu Cys Ala
        115                 120                 125

tct ggt aaa gtc atc tgt ccc tac aat cga aga tgt gtg aac aca ttt     432
Ser Gly Lys Val Ile Cys Pro Tyr Asn Arg Arg Cys Val Asn Thr Phe
    130                 135                 140

gga agc tac tac tgc aaa tgt cac att ggt ttc gaa ctg caa tat atc     480
Gly Ser Tyr Tyr Cys Lys Cys His Ile Gly Phe Glu Leu Gln Tyr Ile
145                 150                 155                 160

agt gga cga tat gac tgt ata gat ata aat gaa tgt act atg gat agc     528
Ser Gly Arg Tyr Asp Cys Ile Asp Ile Asn Glu Cys Thr Met Asp Ser
                165                 170                 175

cat acg tgc agc cac cat gcc aat tgc ttc aat acc caa ggg tcc ttc     576
His Thr Cys Ser His His Ala Asn Cys Phe Asn Thr Gln Gly Ser Phe
            180                 185                 190

aag tgt aaa tgc aag cag gga tat aaa ggc aat gga ctt cgg tgt tct     624
Lys Cys Lys Cys Lys Gln Gly Tyr Lys Gly Asn Gly Leu Arg Cys Ser
        195                 200                 205

gct atc cct gaa aat tct gtg aag gaa gtc ctc aga gca cct ggt acc     672
Ala Ile Pro Glu Asn Ser Val Lys Glu Val Leu Arg Ala Pro Gly Thr
    210                 215                 220

atc aaa gac aga atc aag aag ttg ctt gct cac aaa aac agc atg aaa     720
Ile Lys Asp Arg Ile Lys Lys Leu Leu Ala His Lys Asn Ser Met Lys
225                 230                 235                 240

aag aag gca aaa att aaa aat gtt acc cca gaa ccc acc agg act cct     768
Lys Lys Ala Lys Ile Lys Asn Val Thr Pro Glu Pro Thr Arg Thr Pro
                245                 250                 255

acc cct aag gtg aac ttg cag ccc ttc aac tat gaa gag ata gtt tcc     816
Thr Pro Lys Val Asn Leu Gln Pro Phe Asn Tyr Glu Glu Ile Val Ser
            260                 265                 270

aga ggc ggg aac tct cat gga ggt aaa aaa ggg aat gaa gag aaa atg     864
Arg Gly Gly Asn Ser His Gly Gly Lys Lys Gly Asn Glu Glu Lys Met
        275                 280                 285

aaa gag ggg ctt gag gat gag aaa aga gaa gag aaa gcc ctg aag aat     912
Lys Glu Gly Leu Glu Asp Glu Lys Arg Glu Glu Lys Ala Leu Lys Asn
```

```
    290                 295                 300

gac ata gag gag cga agc ctg cga gga gat gtg ttt ttc cct aag gtg      960
Asp Ile Glu Glu Arg Ser Leu Arg Gly Asp Val Phe Phe Pro Lys Val
305                 310                 315                 320

aat gaa gca ggt gaa ttc ggc ctg att ctg gtc caa agg aaa gcg cta     1008
Asn Glu Ala Gly Glu Phe Gly Leu Ile Leu Val Gln Arg Lys Ala Leu
                325                 330                 335

act tcc aaa ctg gaa cat aaa gat tta aat atc tcg gtt gac tgc agc     1056
Thr Ser Lys Leu Glu His Lys Asp Leu Asn Ile Ser Val Asp Cys Ser
            340                 345                 350

ttc aat cat ggg atc tgt gac tgg aaa cag gat aga gaa gat gat ttt     1104
Phe Asn His Gly Ile Cys Asp Trp Lys Gln Asp Arg Glu Asp Asp Phe
        355                 360                 365

gac tgg aat cct gct gat cga gat aat gct att ggc ttc tat atg gca     1152
Asp Trp Asn Pro Ala Asp Arg Asp Asn Ala Ile Gly Phe Tyr Met Ala
    370                 375                 380

gtt ccg gcc ttg gca ggt cac atg aaa gac att ggc cga ttg aaa ctt     1200
Val Pro Ala Leu Ala Gly His Met Lys Asp Ile Gly Arg Leu Lys Leu
385                 390                 395                 400

ctc cta cct gac ctg caa ccc caa agc aac ttc tgt ttg ctc ttt gat     1248
Leu Leu Pro Asp Leu Gln Pro Gln Ser Asn Phe Cys Leu Leu Phe Asp
                405                 410                 415

tac cgg ctg gcc gga gac aaa gtc ggg aaa ctt cga gtg ttt gtg aaa     1296
Tyr Arg Leu Ala Gly Asp Lys Val Gly Lys Leu Arg Val Phe Val Lys
            420                 425                 430

aac agt aac aat gcc ctg gca tgg gag aag acc acg agt gag gat gaa     1344
Asn Ser Asn Asn Ala Leu Ala Trp Glu Lys Thr Thr Ser Glu Asp Glu
        435                 440                 445

aag tgg aag aca ggg aaa att cag ttg tat caa gga act gat gct acc     1392
Lys Trp Lys Thr Gly Lys Ile Gln Leu Tyr Gln Gly Thr Asp Ala Thr
    450                 455                 460

aaa agc atc att ttt gaa gca gaa cgt ggc aag ggc aaa acc ggc gaa     1440
Lys Ser Ile Ile Phe Glu Ala Glu Arg Gly Lys Gly Lys Thr Gly Glu
465                 470                 475                 480

atc gca gtg gat ggc gtc ttg ctt gtt tca ggc tta tgt cca gat agc     1488
Ile Ala Val Asp Gly Val Leu Leu Val Ser Gly Leu Cys Pro Asp Ser
                485                 490                 495

ctt tta tct gtg gan nnc tgaatggtac tatctttata tttgactttg            1536
Leu Leu Ser Val Xaa Xaa
            500

tatgtcagtt ccctggtttt tttgatattg catcatagga cctctggcat tttaaaatta   1596

ctagctgaaa aattg                                                    1611


<210> SEQ ID NO 3
<211> LENGTH: 100
<212> TYPE: PRT
<213> ORGANISM: Homo sapiens

<400> SEQUENCE: 3

Gly Trp Arg Arg Asn Ser Lys Gly Val Cys Glu Ala Thr Cys Glu Pro
 1               5                  10                  15

Gly Cys Lys Phe Gly Glu Cys Val Gly Pro Asn Lys Cys Arg Cys Phe
            20                  25                  30

Pro Gly Tyr Thr Gly Lys Thr Cys Ser Gln Asp Val Asn Glu Cys Gly
        35                  40                  45

Met Lys Pro Arg Pro Cys Gln His Arg Cys Val Asn Thr His Gly Ser
    50                  55                  60

Tyr Lys Cys Phe Cys Leu Ser Gly His Met Leu Met Pro Asp Ala Thr
```

-continued

```
 65                  70                  75                  80

Cys Val Asn Ser Arg Thr Cys Ala Met Ile Asn Cys Gln Tyr Ser Cys
                85                  90                  95

Glu Asp Thr Glu
            100


<210> SEQ ID NO 4
<211> LENGTH: 537
<212> TYPE: PRT
<213> ORGANISM: Homo sapiens
<220> FEATURE:
<221> NAME/KEY: misc_feature
<222> LOCATION: (503)
<223> OTHER INFORMATION: Xaa = Any Amino Acid

<400> SEQUENCE: 4

Gly Trp Arg Arg Asn Ser Lys Gly Val Cys Glu Ala Thr Cys Glu Pro
  1               5                  10                  15

Gly Cys Lys Phe Gly Glu Cys Val Gly Pro Asn Lys Cys Arg Cys Phe
            20                  25                  30

Pro Gly Tyr Thr Gly Lys Thr Cys Ser Gln Asp Val Asn Glu Cys Gly
        35                  40                  45

Met Lys Pro Arg Pro Cys Gln His Arg Cys Val Asn Thr His Gly Ser
     50                  55                  60

Tyr Lys Cys Phe Cys Leu Ser Gly His Met Leu Met Pro Asp Ala Thr
 65                  70                  75                  80

Cys Val Asn Ser Arg Thr Cys Ala Met Ile Asn Cys Gln Tyr Ser Cys
                85                  90                  95

Glu Asp Thr Glu Glu Gly Pro Gln Cys Leu Cys Pro Ser Ser Gly Leu
            100                 105                 110

Arg Leu Ala Pro Asn Gly Arg Asp Cys Leu Asp Ile Asp Glu Cys Ala
        115                 120                 125

Ser Gly Lys Val Ile Cys Pro Tyr Asn Arg Arg Cys Val Asn Thr Phe
    130                 135                 140

Gly Ser Tyr Tyr Cys Lys Cys His Ile Gly Phe Glu Leu Gln Tyr Ile
145                 150                 155                 160

Ser Gly Arg Tyr Asp Cys Ile Asp Ile Asn Glu Cys Thr Met Asp Ser
                165                 170                 175

His Thr Cys Ser His His Ala Asn Cys Phe Asn Thr Gln Gly Ser Phe
            180                 185                 190

Lys Cys Lys Cys Lys Gln Gly Tyr Lys Gly Asn Gly Leu Arg Cys Ser
        195                 200                 205

Ala Ile Pro Glu Asn Ser Val Lys Glu Val Leu Arg Ala Pro Gly Thr
    210                 215                 220

Ile Lys Asp Arg Ile Lys Lys Leu Leu Ala His Lys Asn Ser Met Lys
225                 230                 235                 240

Lys Lys Ala Lys Ile Lys Asn Val Thr Pro Glu Pro Thr Arg Thr Pro
                245                 250                 255

Thr Pro Lys Val Asn Leu Gln Pro Phe Asn Tyr Glu Glu Ile Val Ser
            260                 265                 270

Arg Gly Gly Asn Ser His Gly Gly Lys Lys Gly Asn Glu Glu Lys Met
        275                 280                 285

Lys Glu Gly Leu Glu Asp Glu Lys Arg Glu Glu Lys Ala Leu Lys Asn
    290                 295                 300

Asp Ile Glu Glu Arg Ser Leu Arg Gly Asp Val Phe Phe Pro Lys Val
305                 310                 315                 320
```

-continued

```
Asn Glu Ala Gly Glu Phe Gly Leu Ile Leu Val Gln Arg Lys Ala Leu
                325                 330                 335

Thr Ser Lys Leu Glu His Lys Asp Leu Asn Ile Ser Val Asp Cys Ser
            340                 345                 350

Phe Asn His Gly Ile Cys Asp Trp Lys Gln Asp Arg Glu Asp Asp Phe
        355                 360                 365

Asp Trp Asn Pro Ala Asp Arg Asp Asn Ala Ile Gly Phe Tyr Met Ala
    370                 375                 380

Val Pro Ala Leu Ala Gly His Met Lys Asp Ile Gly Arg Leu Lys Leu
385                 390                 395                 400

Leu Leu Pro Asp Leu Gln Pro Gln Ser Asn Phe Cys Leu Leu Phe Asp
                405                 410                 415

Tyr Arg Leu Ala Gly Asp Lys Val Gly Lys Leu Arg Val Phe Val Lys
            420                 425                 430

Asn Ser Asn Asn Ala Leu Ala Trp Glu Lys Thr Thr Ser Glu Asp Glu
        435                 440                 445

Lys Trp Lys Thr Gly Lys Ile Gln Leu Tyr Gln Gly Thr Asp Ala Thr
    450                 455                 460

Lys Ser Ile Ile Phe Glu Ala Glu Arg Gly Lys Gly Lys Thr Gly Glu
465                 470                 475                 480

Ile Ala Val Asp Gly Val Leu Leu Val Ser Gly Leu Cys Pro Asp Ser
                485                 490                 495

Leu Leu Ser Val Asp Asp Xaa Met Val Leu Ser Leu Tyr Leu Thr Leu
            500                 505                 510

Tyr Val Ser Ser Leu Val Phe Leu Ile Leu His His Arg Thr Ser Gly
        515                 520                 525

Ile Leu Lys Leu Leu Ala Glu Lys Leu
    530                 535


<210> SEQ ID NO 5
<211> LENGTH: 2365
<212> TYPE: DNA
<213> ORGANISM: Homo sapiens
<220> FEATURE:
<221> NAME/KEY: CDS
<222> LOCATION: (205)...(1866)
<220> FEATURE:
<221> NAME/KEY: misc_feature
<222> LOCATION: (357)
<223> OTHER INFORMATION: Xaa = Any Amino Acid

<400> SEQUENCE: 5

actagtgatt ccatcctaat acgactcact atagggctcg agcggccgcc cgggcaggtc      60

tgcagggaca gcacccggta actgcgagtg gagcggagga cccgagcggc tgaggagaga     120

ggaggcggcg gcttagctgc tacggggtcc ggccggcgcc ctcccgaggg gggctcagga     180

ggaggaagga ggacccgtgc gaga atg cct ctg ccc tgg agc ctt gcg ctc        231
                           Met Pro Leu Pro Trp Ser Leu Ala Leu
                             1               5

ccg ctg ctg ctc ccc tgg gtg gca ggt ggt ttc ggg aac gcg gcc agt       279
Pro Leu Leu Leu Pro Trp Val Ala Gly Gly Phe Gly Asn Ala Ala Ser
 10                  15                  20                  25

gca agg cat cac ggg ttg tta gca tcg gca cgt cag cct ggg gtc tgt       327
Ala Arg His His Gly Leu Leu Ala Ser Ala Arg Gln Pro Gly Val Cys
                 30                  35                  40

cac tat gga act aaa ctg gcc tgc tgc tac ggc tgg aga aga aac agc       375
His Tyr Gly Thr Lys Leu Ala Cys Cys Tyr Gly Trp Arg Arg Asn Ser
             45                  50                  55
```

-continued

```
aag gga gtc tgt gaa gct aca tgc gaa cct gga tgt aag ttt ggt gag      423
Lys Gly Val Cys Glu Ala Thr Cys Glu Pro Gly Cys Lys Phe Gly Glu
        60                  65                  70

tgc gtg gga cca aac aaa tgc aga tgc ttt cca gga tac acc ggg aaa      471
Cys Val Gly Pro Asn Lys Cys Arg Cys Phe Pro Gly Tyr Thr Gly Lys
    75                  80                  85

acc tgc agt caa gat gtg aat gag tgt gga atg aaa ccc cgg cca tgc      519
Thr Cys Ser Gln Asp Val Asn Glu Cys Gly Met Lys Pro Arg Pro Cys
 90                  95                 100                 105

caa cac aga tgt gtg aat aca cac gga agc tac aag tgc ttt tgc ctc      567
Gln His Arg Cys Val Asn Thr His Gly Ser Tyr Lys Cys Phe Cys Leu
                110                 115                 120

agt ggc cac atg ctc atg cca gat gct acg tgt gtg aac tct agg aca      615
Ser Gly His Met Leu Met Pro Asp Ala Thr Cys Val Asn Ser Arg Thr
            125                 130                 135

tgt gcc atg ata aac tgt cag tat agc tgt gaa gac aca gaa gaa ggg      663
Cys Ala Met Ile Asn Cys Gln Tyr Ser Cys Glu Asp Thr Glu Glu Gly
        140                 145                 150

cca cag tgc ctg tgt cca tcc tca gga ctc cgc ctg gcc cca aat gga      711
Pro Gln Cys Leu Cys Pro Ser Ser Gly Leu Arg Leu Ala Pro Asn Gly
    155                 160                 165

aga gac tgt cta gat att gat gaa tgt gcc tct ggt aaa gtc atc tgt      759
Arg Asp Cys Leu Asp Ile Asp Glu Cys Ala Ser Gly Lys Val Ile Cys
170                 175                 180                 185

ccc tac aat cga aga tgt gtg aac aca ttt gga agc tac tac tgc aaa      807
Pro Tyr Asn Arg Arg Cys Val Asn Thr Phe Gly Ser Tyr Tyr Cys Lys
                190                 195                 200

tgt cac att ggt ttc gaa ctg caa tat atc agt gga cga tat gac tgt      855
Cys His Ile Gly Phe Glu Leu Gln Tyr Ile Ser Gly Arg Tyr Asp Cys
            205                 210                 215

ata gat ata aat gaa tgt act atg gat agc cat acg tgc agc cac cat      903
Ile Asp Ile Asn Glu Cys Thr Met Asp Ser His Thr Cys Ser His His
        220                 225                 230

gcc aat tgc ttc aat acc caa ggg tcc ttc aag tgt aaa tgc aag cag      951
Ala Asn Cys Phe Asn Thr Gln Gly Ser Phe Lys Cys Lys Cys Lys Gln
    235                 240                 245

gga tat aaa ggc aat gga ctt cgg tgt tct gct atc cct gaa aat tct      999
Gly Tyr Lys Gly Asn Gly Leu Arg Cys Ser Ala Ile Pro Glu Asn Ser
250                 255                 260                 265

gtg aag gaa gtc ctc aga gca cct ggt acc atc aaa gac aga atc aag     1047
Val Lys Glu Val Leu Arg Ala Pro Gly Thr Ile Lys Asp Arg Ile Lys
                270                 275                 280

aag ttg ctt gct cac aaa aac agc atg aaa aag aag gca aaa att aaa     1095
Lys Leu Leu Ala His Lys Asn Ser Met Lys Lys Lys Ala Lys Ile Lys
            285                 290                 295

aat gtt acc cca gaa ccc acc agg act cct acc cct aag gtg aac ttg     1143
Asn Val Thr Pro Glu Pro Thr Arg Thr Pro Thr Pro Lys Val Asn Leu
        300                 305                 310

cag ccc ttc aac tat gaa gag ata gtt tcc aga ggc ggg aac tct cat     1191
Gln Pro Phe Asn Tyr Glu Glu Ile Val Ser Arg Gly Gly Asn Ser His
    315                 320                 325

gga ggt aaa aaa ggg aat gaa gag aaa atg aaa gag ggg ctt gag gat     1239
Gly Gly Lys Lys Gly Asn Glu Glu Lys Met Lys Glu Gly Leu Glu Asp
330                 335                 340                 345

gag aaa aga gaa gag aaa gcc ctg aag aat gac wta gag gag cga agc     1287
Glu Lys Arg Glu Glu Lys Ala Leu Lys Asn Asp Xaa Glu Glu Arg Ser
                350                 355                 360

ctg cga gga gat gtg ttt ttc cct aag gtg aat gaa gca ggt gaa ttc     1335
Leu Arg Gly Asp Val Phe Phe Pro Lys Val Asn Glu Ala Gly Glu Phe
```

-continued

```
            365                 370                 375

ggc ctg att ctg gtc caa agg aaa gcg cta act tcc aaa ctg gaa cat     1383
Gly Leu Ile Leu Val Gln Arg Lys Ala Leu Thr Ser Lys Leu Glu His
        380                 385                 390

aaa gat tta aat atc tcg gtt gac tgc agc ttc aat cat ggg atc tgt     1431
Lys Asp Leu Asn Ile Ser Val Asp Cys Ser Phe Asn His Gly Ile Cys
    395                 400                 405

gac tgg aaa cag gat aga gaa gat gat ttt gac tgg aat cct gct gat     1479
Asp Trp Lys Gln Asp Arg Glu Asp Asp Phe Asp Trp Asn Pro Ala Asp
410                 415                 420                 425

cga gat aat gct att ggc ttc tat atg gca gtt ccg gcc ttg gca ggt     1527
Arg Asp Asn Ala Ile Gly Phe Tyr Met Ala Val Pro Ala Leu Ala Gly
                430                 435                 440

cac aag aaa gac att ggc cga ttg aaa ctt ctc cta cct gac ctg caa     1575
His Lys Lys Asp Ile Gly Arg Leu Lys Leu Leu Leu Pro Asp Leu Gln
            445                 450                 455

ccc caa agc aac ttc tgt ttg ctc ttt gat tac cgg ctg gcc gga gac     1623
Pro Gln Ser Asn Phe Cys Leu Leu Phe Asp Tyr Arg Leu Ala Gly Asp
        460                 465                 470

aaa gtc ggg aaa ctt cga gtg ttt gtg aaa aac agt aac aat gcc ctg     1671
Lys Val Gly Lys Leu Arg Val Phe Val Lys Asn Ser Asn Asn Ala Leu
    475                 480                 485

gca tgg gag aag acc acg agt gag gat gaa aag tgg aag aca ggg aaa     1719
Ala Trp Glu Lys Thr Thr Ser Glu Asp Glu Lys Trp Lys Thr Gly Lys
490                 495                 500                 505

att cag ttg tat caa gga act gat gct acc aaa agc atc att ttt gaa     1767
Ile Gln Leu Tyr Gln Gly Thr Asp Ala Thr Lys Ser Ile Ile Phe Glu
                510                 515                 520

gca gaa cgt ggc aag ggc aaa acc ggc gaa atc gca gtg gat ggc gtc     1815
Ala Glu Arg Gly Lys Gly Lys Thr Gly Glu Ile Ala Val Asp Gly Val
            525                 530                 535

ttg ctt gtt tca ggc tta tgt cca gat agc ctt tta tct gtg gat gac     1863
Leu Leu Val Ser Gly Leu Cys Pro Asp Ser Leu Leu Ser Val Asp Asp
        540                 545                 550

tga atgttactat ctttatattt gactttgtat gtcagttccc tggttttttt          1916

gatattgsat cataggacct ctggcatttt aaaattacta agctgaaaaa ttgtaatgta   1976

ccaacagaaa ttattattgt aagatgcctt tmttgtataa gatatgccaa tatttgcttt   2036

aaatatcata tcactgtatc ttctcagtca tttctgaatc tttccacatt atattataaa   2096

atatggaaat gtcaggttta tctcccctcc tcagtatatc tgatttgtat aagtaagttg   2156

atgagcttct ctctgcaaca tttctagaaa atagahaaaa aagcacagag aaatgtttaa   2216

ctgtttgact cttatgatag tttttggaaa ctatgacatc aaagatagac ttttgcctaa   2276

gtggcttagc tgggtctttc atagccaaac ttgtatattt aaattctttg taataataat   2336

atccaaatca tcaaaaaaaa aaaaaaaaa                                      2365
```

<210> SEQ ID NO 6
<211> LENGTH: 553
<212> TYPE: PRT
<213> ORGANISM: Homo sapiens
<220> FEATURE:
<221> NAME/KEY: misc_feature
<222> LOCATION: (357)
<223> OTHER INFORMATION: Xaa = Any Amino Acid

<400> SEQUENCE: 6

```
Met Pro Leu Pro Trp Ser Leu Ala Leu Pro Leu Leu Leu Pro Trp Val
 1               5                  10                  15
```

-continued

```
Ala Gly Gly Phe Gly Asn Ala Ala Ser Ala Arg His His Gly Leu Leu
            20                  25                  30

Ala Ser Ala Arg Gln Pro Gly Val Cys His Tyr Gly Thr Lys Leu Ala
        35                  40                  45

Cys Cys Tyr Gly Trp Arg Arg Asn Ser Lys Gly Val Cys Glu Ala Thr
    50                  55                  60

Cys Glu Pro Gly Cys Lys Phe Gly Glu Cys Val Gly Pro Asn Lys Cys
65                  70                  75                  80

Arg Cys Phe Pro Gly Tyr Thr Gly Lys Thr Cys Ser Gln Asp Val Asn
                85                  90                  95

Glu Cys Gly Met Lys Pro Arg Pro Cys Gln His Arg Cys Val Asn Thr
            100                 105                 110

His Gly Ser Tyr Lys Cys Phe Cys Leu Ser Gly His Met Leu Met Pro
        115                 120                 125

Asp Ala Thr Cys Val Asn Ser Arg Thr Cys Ala Met Ile Asn Cys Gln
    130                 135                 140

Tyr Ser Cys Glu Asp Thr Glu Glu Gly Pro Gln Cys Leu Cys Pro Ser
145                 150                 155                 160

Ser Gly Leu Arg Leu Ala Pro Asn Gly Arg Asp Cys Leu Asp Ile Asp
                165                 170                 175

Glu Cys Ala Ser Gly Lys Val Ile Cys Pro Tyr Asn Arg Arg Cys Val
            180                 185                 190

Asn Thr Phe Gly Ser Tyr Tyr Cys Lys Cys His Ile Gly Phe Glu Leu
        195                 200                 205

Gln Tyr Ile Ser Gly Arg Tyr Asp Cys Ile Asp Ile Asn Glu Cys Thr
    210                 215                 220

Met Asp Ser His Thr Cys Ser His His Ala Asn Cys Phe Asn Thr Gln
225                 230                 235                 240

Gly Ser Phe Lys Cys Lys Cys Lys Gln Gly Tyr Lys Gly Asn Gly Leu
                245                 250                 255

Arg Cys Ser Ala Ile Pro Glu Asn Ser Val Lys Glu Val Leu Arg Ala
            260                 265                 270

Pro Gly Thr Ile Lys Asp Arg Ile Lys Lys Leu Leu Ala His Lys Asn
        275                 280                 285

Ser Met Lys Lys Lys Ala Lys Ile Lys Asn Val Thr Pro Glu Pro Thr
    290                 295                 300

Arg Thr Pro Thr Pro Lys Val Asn Leu Gln Pro Phe Asn Tyr Glu Glu
305                 310                 315                 320

Ile Val Ser Arg Gly Gly Asn Ser His Gly Gly Lys Lys Gly Asn Glu
                325                 330                 335

Glu Lys Met Lys Glu Gly Leu Glu Asp Glu Lys Arg Glu Glu Lys Ala
            340                 345                 350

Leu Lys Asn Asp Xaa Glu Glu Arg Ser Leu Arg Gly Asp Val Phe Phe
        355                 360                 365

Pro Lys Val Asn Glu Ala Gly Glu Phe Gly Leu Ile Leu Val Gln Arg
    370                 375                 380

Lys Ala Leu Thr Ser Lys Leu Glu His Lys Asp Leu Asn Ile Ser Val
385                 390                 395                 400

Asp Cys Ser Phe Asn His Gly Ile Cys Asp Trp Lys Gln Asp Arg Glu
                405                 410                 415

Asp Asp Phe Asp Trp Asn Pro Ala Asp Arg Asp Asn Ala Ile Gly Phe
            420                 425                 430

Tyr Met Ala Val Pro Ala Leu Ala Gly His Lys Lys Asp Ile Gly Arg
```

-continued

```
        435                 440                 445

Leu Lys Leu Leu Leu Pro Asp Leu Gln Pro Gln Ser Asn Phe Cys Leu
    450                 455                 460

Leu Phe Asp Tyr Arg Leu Ala Gly Asp Lys Val Gly Lys Leu Arg Val
465                 470                 475                 480

Phe Val Lys Asn Ser Asn Asn Ala Leu Ala Trp Glu Lys Thr Thr Ser
                485                 490                 495

Glu Asp Glu Lys Trp Lys Thr Gly Lys Ile Gln Leu Tyr Gln Gly Thr
            500                 505                 510

Asp Ala Thr Lys Ser Ile Ile Phe Glu Ala Glu Arg Gly Lys Gly Lys
        515                 520                 525

Thr Gly Glu Ile Ala Val Asp Gly Val Leu Leu Val Ser Gly Leu Cys
    530                 535                 540

Pro Asp Ser Leu Leu Ser Val Asp Asp
545                 550
```

<210> SEQ ID NO 7
<211> LENGTH: 42
<212> TYPE: PRT
<213> ORGANISM: Drosophila Melanogaster
<220> FEATURE:
<221> NAME/KEY: misc_feature
<222> LOCATION: (5)
<223> OTHER INFORMATION: Xaa = Any Amino Acid
<220> FEATURE:
<221> NAME/KEY: misc_feature
<222> LOCATION: (16)
<223> OTHER INFORMATION: Xaa = Any Amino Acid
<220> FEATURE:
<221> NAME/KEY: misc_feature
<222> LOCATION: (17)
<223> OTHER INFORMATION: Xaa = Any Amino Acid
<220> FEATURE:
<221> NAME/KEY: misc_feature
<222> LOCATION: (18)
<223> OTHER INFORMATION: Xaa = Any Amino Acid
<220> FEATURE:
<221> NAME/KEY: misc_feature
<222> LOCATION: (20)
<223> OTHER INFORMATION: Xaa = Any Amino Acid
<220> FEATURE:
<221> NAME/KEY: misc_feature
<222> LOCATION: (25)
<223> OTHER INFORMATION: Xaa = Any Amino Acid
<220> FEATURE:
<221> NAME/KEY: misc_feature
<222> LOCATION: (27)
<223> OTHER INFORMATION: Xaa = Any Amino Acid
<220> FEATURE:
<221> NAME/KEY: misc_feature
<222> LOCATION: (36)
<223> OTHER INFORMATION: Xaa = Any Amino Acid
<220> FEATURE:
<221> NAME/KEY: misc_feature
<222> LOCATION: (37)
<223> OTHER INFORMATION: Xaa = Any Amino Acid
<220> FEATURE:
<221> NAME/KEY: misc_feature
<222> LOCATION: (38)
<223> OTHER INFORMATION: Xaa = Any Amino Acid
<220> FEATURE:
<221> NAME/KEY: misc_feature
<222> LOCATION: (41)
<223> OTHER INFORMATION: Xaa = Any Amino Acid

<400> SEQUENCE: 7

```
Ile Asp Glu Cys Xaa Ser Asn Pro Cys Gln Asn Gly Gly Thr Cys Xaa
 1               5                  10                  15

Xaa Xaa Asp Xaa Val Gly Ser Tyr Xaa Cys Xaa Cys Pro Pro Gly Phe
```

-continued

```
            20                  25                  30

Thr Gly Lys Xaa Xaa Xaa Cys Glu Xaa Asn
        35                  40


<210> SEQ ID NO 8
<211> LENGTH: 39
<212> TYPE: PRT
<213> ORGANISM: Homo sapiens
<220> FEATURE:
<221> NAME/KEY: misc_feature
<222> LOCATION: (1)
<223> OTHER INFORMATION: Xaa = Any Amino Acid
<220> FEATURE:
<221> NAME/KEY: misc_feature
<222> LOCATION: (7)
<223> OTHER INFORMATION: Xaa = Any Amino Acid
<220> FEATURE:
<221> NAME/KEY: misc_feature
<222> LOCATION: (8)
<223> OTHER INFORMATION: Xaa = Any Amino Acid
<220> FEATURE:
<221> NAME/KEY: misc_feature
<222> LOCATION: (9)
<223> OTHER INFORMATION: Xaa = Any Amino Acid
<220> FEATURE:
<221> NAME/KEY: misc_feature
<222> LOCATION: (13)
<223> OTHER INFORMATION: Xaa = Any Amino Acid
<220> FEATURE:
<221> NAME/KEY: misc_feature
<222> LOCATION: (14)
<223> OTHER INFORMATION: Xaa = Any Amino Acid
<220> FEATURE:
<221> NAME/KEY: misc_feature
<222> LOCATION: (15)
<223> OTHER INFORMATION: Xaa = Any Amino Acid
<220> FEATURE:
<221> NAME/KEY: misc_feature
<222> LOCATION: (20)
<223> OTHER INFORMATION: Xaa = Any Amino Acid
<220> FEATURE:
<221> NAME/KEY: misc_feature
<222> LOCATION: (24)
<223> OTHER INFORMATION: Xaa = Any Amino Acid
<220> FEATURE:
<221> NAME/KEY: misc_feature
<222> LOCATION: (28)
<223> OTHER INFORMATION: Xaa = Any Amino Acid
<220> FEATURE:
<221> NAME/KEY: misc_feature
<222> LOCATION: (31)
<223> OTHER INFORMATION: Xaa = Any Amino Acid
<220> FEATURE:
<221> NAME/KEY: misc_feature
<222> LOCATION: (32)
<223> OTHER INFORMATION: Xaa = Any Amino Acid
<220> FEATURE:
<221> NAME/KEY: misc_feature
<222> LOCATION: (34)
<223> OTHER INFORMATION: Xaa = Any Amino Acid
<220> FEATURE:
<221> NAME/KEY: misc_feature
<222> LOCATION: (35)
<223> OTHER INFORMATION: Xaa = Any Amino Acid
<220> FEATURE:
<221> NAME/KEY: misc_feature
<222> LOCATION: (37)
<223> OTHER INFORMATION: Xaa = Any Amino Acid

<400> SEQUENCE: 8

Xaa Asn Glu Cys Thr Met Xaa Xaa Xaa Cys Gln His Xaa Xaa Xaa Cys
 1               5                  10                  15

Val Asn Thr Xaa Gly Ser Tyr Xaa Cys Lys Cys Xaa Ser Gly Xaa Xaa
            20                  25                  30
```

-continued

```
Gly Xaa Xaa Leu Xaa Cys Asp
        35


<210> SEQ ID NO 9
<211> LENGTH: 164
<212> TYPE: PRT
<213> ORGANISM: Homo sapiens

<400> SEQUENCE: 9

Cys Arg Cys Phe Pro Gly Tyr Thr Gly Lys Thr Cys Ser Gln Val Asn
 1               5                  10                  15

Glu Cys Gly Met Lys Pro Arg Pro Cys Gln His Arg Cys Val Asn Thr
            20                  25                  30

His Gly Ser Tyr Lys Cys Phe Cys Leu Ser Gly His Met Leu Met Pro
        35                  40                  45

Asp Val Asn Ser Arg Thr Cys Ala Met Ile Asn Cys Gln Tyr Ser Cys
    50                  55                  60

Glu Asp Thr Glu Glu Gly Pro Gln Cys Leu Cys Pro Ser Ser Gly Leu
65                  70                  75                  80

Arg Leu Ala Pro Asn Ile Asp Glu Cys Ala Ser Gly Lys Val Ile Cys
                85                  90                  95

Pro Tyr Asn Arg Arg Cys Val Asn Thr Phe Gly Ser Tyr Tyr Cys Lys
            100                 105                 110

Cys His Ile Gly Phe Glu Leu Gln Tyr Ile Ser Gly Arg Ile Asn Glu
        115                 120                 125

Cys Thr Met Asp Ser His Thr Cys Ser His His Ala Asn Cys Phe Asn
    130                 135                 140

Thr Gln Gly Ser Phe Cys Lys Cys Lys Gln Gly Tyr Lys Gly Asn Gly
145                 150                 155                 160

Leu Arg Cys Ser


<210> SEQ ID NO 10
<211> LENGTH: 45
<212> TYPE: PRT
<213> ORGANISM: Homo sapiens
<220> FEATURE:
<221> NAME/KEY: misc_feature
<222> LOCATION: (2)
<223> OTHER INFORMATION: Xaa = Any Amino Acid
<220> FEATURE:
<221> NAME/KEY: misc_feature
<222> LOCATION: (5)
<223> OTHER INFORMATION: Xaa = Any Amino Acid
<220> FEATURE:
<221> NAME/KEY: misc_feature
<222> LOCATION: (8)
<223> OTHER INFORMATION: Xaa = Any Amino Acid
<220> FEATURE:
<221> NAME/KEY: misc_feature
<222> LOCATION: (10)
<223> OTHER INFORMATION: Xaa = Any Amino Acid
<220> FEATURE:
<221> NAME/KEY: misc_feature
<222> LOCATION: (11)
<223> OTHER INFORMATION: Xaa = Any Amino Acid
<220> FEATURE:
<221> NAME/KEY: misc_feature
<222> LOCATION: (13)
<223> OTHER INFORMATION: Xaa = Any Amino Acid
<220> FEATURE:
<221> NAME/KEY: misc_feature
<222> LOCATION: (16)
<223> OTHER INFORMATION: Xaa = Any Amino Acid
<220> FEATURE:
<221> NAME/KEY: misc_feature
<222> LOCATION: (17)
```

-continued

<223> OTHER INFORMATION: Xaa = Any Amino Acid
<220> FEATURE:
<221> NAME/KEY: misc_feature
<222> LOCATION: (19)
<223> OTHER INFORMATION: Xaa = Any Amino Acid
<220> FEATURE:
<221> NAME/KEY: misc_feature
<222> LOCATION: (26)
<223> OTHER INFORMATION: Xaa = Any Amino Acid
<220> FEATURE:
<221> NAME/KEY: misc_feature
<222> LOCATION: (34)
<223> OTHER INFORMATION: Xaa = Any Amino Acid
<220> FEATURE:
<221> NAME/KEY: misc_feature
<222> LOCATION: (36)
<223> OTHER INFORMATION: Xaa = Any Amino Acid
<220> FEATURE:
<221> NAME/KEY: misc_feature
<222> LOCATION: (39)
<223> OTHER INFORMATION: Xaa = Any Amino Acid
<220> FEATURE:
<221> NAME/KEY: misc_feature
<222> LOCATION: (42)
<223> OTHER INFORMATION: Xaa = Any Amino Acid
<220> FEATURE:
<221> NAME/KEY: misc_feature
<222> LOCATION: (43)
<223> OTHER INFORMATION: Xaa = Any Amino Acid
<220> FEATURE:
<221> NAME/KEY: misc_feature
<222> LOCATION: (44)
<223> OTHER INFORMATION: Xaa = Any Amino Acid

<400> SEQUENCE: 10

```
Val Xaa Glu Cys Xaa Ser Gly Xaa Gln Xaa Xaa Cys Xaa Ser Ser Xaa
 1               5                  10                  15

Xaa Cys Xaa Asn Thr Val Gly Ser Tyr Xaa Cys Arg Cys Arg Pro Gly
            20                  25                  30

Trp Xaa Pro Xaa Pro Gly Xaa Pro Asn Xaa Xaa Xaa Asp
        35                  40                  45
```

<210> SEQ ID NO 11
<211> LENGTH: 58
<212> TYPE: PRT
<213> ORGANISM: Mammalian
<220> FEATURE:
<221> NAME/KEY: misc_feature
<222> LOCATION: (39)
<223> OTHER INFORMATION: Xaa = Any Amino Acid
<220> FEATURE:
<221> NAME/KEY: misc_feature
<222> LOCATION: (40)
<223> OTHER INFORMATION: Xaa = Any Amino Acid
<220> FEATURE:
<221> NAME/KEY: misc_feature
<222> LOCATION: (41)
<223> OTHER INFORMATION: Xaa = Any Amino Acid
<220> FEATURE:
<221> NAME/KEY: misc_feature
<222> LOCATION: (45)
<223> OTHER INFORMATION: Xaa = Any Amino Acid
<220> FEATURE:
<221> NAME/KEY: misc_feature
<222> LOCATION: (46)
<223> OTHER INFORMATION: Xaa = Any Amino Acid

<400> SEQUENCE: 11

```
Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30
```

-continued

```
Cys Val Val Gly Tyr Ile Xaa Xaa Xaa Gly Glu Arg Xaa Xaa Cys Gln
        35                  40                  45

Tyr Arg Asp Leu Lys Trp Trp Glu Leu Arg
    50                  55


<210> SEQ ID NO 12
<211> LENGTH: 21
<212> TYPE: DNA
<213> ORGANISM: Artificial Sequence
<220> FEATURE:
<223> OTHER INFORMATION: Gene-specific PCR primer 10244-52

<400> SEQUENCE: 12

ctcatcctca agcccctctt t                                               21


<210> SEQ ID NO 13
<211> LENGTH: 21
<212> TYPE: DNA
<213> ORGANISM: Artificial Sequence
<220> FEATURE:
<223> OTHER INFORMATION: Gene-specific PCR primer 10244-51

<400> SEQUENCE: 13

ccatgagagt tcccgcctct g                                               21


<210> SEQ ID NO 14
<211> LENGTH: 21
<212> TYPE: DNA
<213> ORGANISM: Artificial Sequence
<220> FEATURE:
<223> OTHER INFORMATION: Vector primer T7

<400> SEQUENCE: 14

gtaatacgac tcactatagg g                                               21


<210> SEQ ID NO 15
<211> LENGTH: 22
<212> TYPE: DNA
<213> ORGANISM: Artificial Sequence
<220> FEATURE:
<223> OTHER INFORMATION: Vector primer SP6

<400> SEQUENCE: 15

atttaggtga cactatagaa gg                                              22


<210> SEQ ID NO 16
<211> LENGTH: 21
<212> TYPE: DNA
<213> ORGANISM: Artificial Sequence
<220> FEATURE:
<223> OTHER INFORMATION: Gene-specific PCR primer 10244-A

<400> SEQUENCE: 16

cccaggctga cgtgccgatg c                                               21


<210> SEQ ID NO 17
<211> LENGTH: 21
<212> TYPE: DNA
<213> ORGANISM: Artificial Sequence
<220> FEATURE:
<223> OTHER INFORMATION: Gene-specific PCR primer 10244-B

<400> SEQUENCE: 17

gcagcaggcc agtttagttc c                                               21
```

-continued

<210> SEQ ID NO 18
<211> LENGTH: 502
<212> TYPE: PRT
<213> ORGANISM: Homo sapiens
<220> FEATURE:
<221> NAME/KEY: misc_feature
<222> LOCATION: (501)
<223> OTHER INFORMATION: Xaa = Any Amino Acid
<220> FEATURE:
<221> NAME/KEY: misc_feature
<222> LOCATION: (502)
<223> OTHER INFORMATION: Xaa = Any Amino Acid

<400> SEQUENCE: 18

```
Gly Trp Arg Arg Asn Ser Lys Gly Val Cys Glu Ala Thr Cys Glu Pro
 1               5                  10                  15

Gly Cys Lys Phe Gly Glu Cys Val Gly Pro Asn Lys Cys Arg Cys Phe
            20                  25                  30

Pro Gly Tyr Thr Gly Lys Thr Cys Ser Gln Asp Val Asn Glu Cys Gly
        35                  40                  45

Met Lys Pro Arg Pro Cys Gln His Arg Cys Val Asn Thr His Gly Ser
    50                  55                  60

Tyr Lys Cys Phe Cys Leu Ser Gly His Met Leu Met Pro Asp Ala Thr
65                  70                  75                  80

Cys Val Asn Ser Arg Thr Cys Ala Met Ile Asn Cys Gln Tyr Ser Cys
                85                  90                  95

Glu Asp Thr Glu Glu Gly Pro Gln Cys Leu Cys Pro Ser Ser Gly Leu
            100                 105                 110

Arg Leu Ala Pro Asn Gly Arg Asp Cys Leu Asp Ile Asp Glu Cys Ala
        115                 120                 125

Ser Gly Lys Val Ile Cys Pro Tyr Asn Arg Arg Cys Val Asn Thr Phe
    130                 135                 140

Gly Ser Tyr Tyr Cys Lys Cys His Ile Gly Phe Glu Leu Gln Tyr Ile
145                 150                 155                 160

Ser Gly Arg Tyr Asp Cys Ile Asp Ile Asn Glu Cys Thr Met Asp Ser
                165                 170                 175

His Thr Cys Ser His His Ala Asn Cys Phe Asn Thr Gln Gly Ser Phe
            180                 185                 190

Lys Cys Lys Cys Lys Gln Gly Tyr Lys Gly Asn Gly Leu Arg Cys Ser
        195                 200                 205

Ala Ile Pro Glu Asn Ser Val Lys Glu Val Leu Arg Ala Pro Gly Thr
    210                 215                 220

Ile Lys Asp Arg Ile Lys Lys Leu Leu Ala His Lys Asn Ser Met Lys
225                 230                 235                 240

Lys Lys Ala Lys Ile Lys Asn Val Thr Pro Glu Pro Thr Arg Thr Pro
                245                 250                 255

Thr Pro Lys Val Asn Leu Gln Pro Phe Asn Tyr Glu Glu Ile Val Ser
            260                 265                 270

Arg Gly Gly Asn Ser His Gly Gly Lys Lys Gly Asn Glu Glu Lys Met
        275                 280                 285

Lys Glu Gly Leu Glu Asp Glu Lys Arg Glu Glu Lys Ala Leu Lys Asn
    290                 295                 300

Asp Ile Glu Glu Arg Ser Leu Arg Gly Asp Val Phe Phe Pro Lys Val
305                 310                 315                 320

Asn Glu Ala Gly Glu Phe Gly Leu Ile Leu Val Gln Arg Lys Ala Leu
                325                 330                 335

Thr Ser Lys Leu Glu His Lys Asp Leu Asn Ile Ser Val Asp Cys Ser
```

-continued

```
            340                 345                 350

Phe Asn His Gly Ile Cys Asp Trp Lys Gln Asp Arg Glu Asp Asp Phe
        355                 360                 365

Asp Trp Asn Pro Ala Asp Arg Asp Asn Ala Ile Gly Phe Tyr Met Ala
    370                 375                 380

Val Pro Ala Leu Ala Gly His Met Lys Asp Ile Gly Arg Leu Lys Leu
385                 390                 395                 400

Leu Leu Pro Asp Leu Gln Pro Gln Ser Asn Phe Cys Leu Leu Phe Asp
                405                 410                 415

Tyr Arg Leu Ala Gly Asp Lys Val Gly Lys Leu Arg Val Phe Val Lys
            420                 425                 430

Asn Ser Asn Asn Ala Leu Ala Trp Glu Lys Thr Thr Ser Glu Asp Glu
        435                 440                 445

Lys Trp Lys Thr Gly Lys Ile Gln Leu Tyr Gln Gly Thr Asp Ala Thr
    450                 455                 460

Lys Ser Ile Ile Phe Glu Ala Glu Arg Gly Lys Gly Lys Thr Gly Glu
465                 470                 475                 480

Ile Ala Val Asp Gly Val Leu Leu Val Ser Gly Leu Cys Pro Asp Ser
                485                 490                 495

Leu Leu Ser Val Xaa Xaa
            500


<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 19

gtcatttctg aatctttcca c                                               21


<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 20

gaaatgttgc agagagaagc tc                                              22


<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 21

ccagaaccca ccaggactcc                                                 20


<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 22

gggaactgac atacaaagtc                                                 20
```

-continued

<210> SEQ ID NO 23
<211> LENGTH: 2365
<212> TYPE: DNA
<213> ORGANISM: Homo sapiens
<220> FEATURE:
<221> NAME/KEY: CDS
<222> LOCATION: (205)..(1863)

<400> SEQUENCE: 23
actagtgatt ccatcctaat acgactcact atagggctcg agcggccgcc cgggcaggtc 60
tgcagggaca gcacccggta actgcgagtg gagcggagga cccgagcggc tgaggagaga 120
ggaggcggcg gcttagctgc tacggggtcc ggccggcgcc ctcccgaggg gggctcagga 180
ggaggaagga ggacccgtgc gaga atg cct ctg ccc tgg agc ctt gcg ctc 231
Met Pro Leu Pro Trp Ser Leu Ala Leu
1 5 ccg ctg ctg ctc tcc tgg gtg gca ggt ggt ttc ggg aac gcg gcc agt 279
Pro Leu Leu Leu Ser Trp Val Ala Gly Gly Phe Gly Asn Ala Ala Ser
10 15 20 25 gca agg cat cac ggg ttg tta gca tcg gca cgt cag cct ggg gtc tgt 327
Ala Arg His His Gly Leu Leu Ala Ser Ala Arg Gln Pro Gly Val Cys
30 35 40 cac tat gga act aaa ctg gcc tgc tgc tac ggc tgg aga aga aac agc 375
His Tyr Gly Thr Lys Leu Ala Cys Cys Tyr Gly Trp Arg Arg Asn Ser
45 50 55 aag gga gtc tgt gaa gct aca tgc gaa cct gga tgt aag ttt ggt gag 423
Lys Gly Val Cys Glu Ala Thr Cys Glu Pro Gly Cys Lys Phe Gly Glu
60 65 70 tgc gtg gga cca aac aaa tgc aga tgc ttt cca gga tac acc ggg aaa 471
Cys Val Gly Pro Asn Lys Cys Arg Cys Phe Pro Gly Tyr Thr Gly Lys
75 80 85 acc tgc agt caa gat gtg aat gag tgt gga atg aaa ccc cgg cca tgc 519
Thr Cys Ser Gln Asp Val Asn Glu Cys Gly Met Lys Pro Arg Pro Cys
90 95 100 105 caa cac aga tgt gtg aat aca cac gga agc tac aag tgc ttt tgc ctc 567
Gln His Arg Cys Val Asn Thr His Gly Ser Tyr Lys Cys Phe Cys Leu
110 115 120 agt ggc cac atg ctc atg cca gat gct acg tgt gtg aac tct agg aca 615
Ser Gly His Met Leu Met Pro Asp Ala Thr Cys Val Asn Ser Arg Thr
125 130 135 tgt gcc atg ata aac tgt cag tat agc tgt gaa gac aca gaa gaa ggg 663
Cys Ala Met Ile Asn Cys Gln Tyr Ser Cys Glu Asp Thr Glu Glu Gly
140 145 150 cca cag tgc ctg tgt cca tcc tca gga ctc cgc ctg gcc cca aat gga 711
Pro Gln Cys Leu Cys Pro Ser Ser Gly Leu Arg Leu Ala Pro Asn Gly
155 160 165 aga gac tgt cta gat att gat gaa tgt gcc tct ggt aaa gtc atc tgt 759
Arg Asp Cys Leu Asp Ile Asp Glu Cys Ala Ser Gly Lys Val Ile Cys
170 175 180 185 ccc tac aat cga aga tgt gtg aac aca ttt gga agc tac tac tgc aaa 807
Pro Tyr Asn Arg Arg Cys Val Asn Thr Phe Gly Ser Tyr Tyr Cys Lys
190 195 200 tgt cac att ggt ttc gaa ctg caa tat atc agt gga cga tat gac tgt 855
Cys His Ile Gly Phe Glu Leu Gln Tyr Ile Ser Gly Arg Tyr Asp Cys
205 210 215 ata gat ata aat gaa tgt act atg gat agc cat acg tgc agc cac cat 903
Ile Asp Ile Asn Glu Cys Thr Met Asp Ser His Thr Cys Ser His His
220 225 230 gcc aat tgc ttc aat acc caa ggg tcc ttc aag tgt aaa tgc aag cag 951

-continued

```
Ala Asn Cys Phe Asn Thr Gln Gly Ser Phe Lys Cys Lys Cys Lys Gln
    235                 240                 245

gga tat aaa ggc aat gga ctt cgg tgt tct gct atc cct gaa aat tct      999
Gly Tyr Lys Gly Asn Gly Leu Arg Cys Ser Ala Ile Pro Glu Asn Ser
250                 255                 260                 265

gtg aag gaa gtc ctc aga gca cct ggt acc atc aaa gac aga atc aag     1047
Val Lys Glu Val Leu Arg Ala Pro Gly Thr Ile Lys Asp Arg Ile Lys
                270                 275                 280

aag ttg ctt gct cac aaa aac agc atg aaa aag aag gca aaa att aaa     1095
Lys Leu Leu Ala His Lys Asn Ser Met Lys Lys Lys Ala Lys Ile Lys
            285                 290                 295

aat gtt acc cca gaa ccc acc agg act cct acc cct aag gtg aac ttg     1143
Asn Val Thr Pro Glu Pro Thr Arg Thr Pro Thr Pro Lys Val Asn Leu
        300                 305                 310

cag ccc ttc aac tat gaa gag ata gtt tcc aga ggc ggg aac tct cat     1191
Gln Pro Phe Asn Tyr Glu Glu Ile Val Ser Arg Gly Gly Asn Ser His
    315                 320                 325

gga ggt aaa aaa ggg aat gaa gag aaa atg aaa gag ggg ctt gag gat     1239
Gly Gly Lys Lys Gly Asn Glu Glu Lys Met Lys Glu Gly Leu Glu Asp
330                 335                 340                 345

gag aaa aga gaa gag aaa gcc ctg aag aat gac ata gag gag cga agc     1287
Glu Lys Arg Glu Glu Lys Ala Leu Lys Asn Asp Ile Glu Glu Arg Ser
                350                 355                 360

ctg cga gga gat gtg ttt ttc cct aag gtg aat gaa gca ggt gaa ttc     1335
Leu Arg Gly Asp Val Phe Phe Pro Lys Val Asn Glu Ala Gly Glu Phe
            365                 370                 375

ggc ctg att ctg gtc caa agg aaa gcg cta act tcc aaa ctg gaa cat     1383
Gly Leu Ile Leu Val Gln Arg Lys Ala Leu Thr Ser Lys Leu Glu His
        380                 385                 390

aaa gat tta aat atc tcg gtt gac tgc agc ttc aat cat ggg atc tgt     1431
Lys Asp Leu Asn Ile Ser Val Asp Cys Ser Phe Asn His Gly Ile Cys
    395                 400                 405

gac tgg aaa cag gat aga gaa gat gat ttt gac tgg aat cct gct gat     1479
Asp Trp Lys Gln Asp Arg Glu Asp Asp Phe Asp Trp Asn Pro Ala Asp
410                 415                 420                 425

cga gat aat gct att ggc ttc tat atg gca gtt ccg gcc ttg gca ggt     1527
Arg Asp Asn Ala Ile Gly Phe Tyr Met Ala Val Pro Ala Leu Ala Gly
                430                 435                 440

cac aag aaa gac att ggc cga ttg aaa ctt ctc cta cct gac ctg caa     1575
His Lys Lys Asp Ile Gly Arg Leu Lys Leu Leu Leu Pro Asp Leu Gln
            445                 450                 455

ccc caa agc aac ttc tgt ttg ctc ttt gat tac cgg ctg gcc gga gac     1623
Pro Gln Ser Asn Phe Cys Leu Leu Phe Asp Tyr Arg Leu Ala Gly Asp
        460                 465                 470

aaa gtc ggg aaa ctt cga gtg ttt gtg aaa aac agt aac aat gcc ctg     1671
Lys Val Gly Lys Leu Arg Val Phe Val Lys Asn Ser Asn Asn Ala Leu
    475                 480                 485

gca tgg gag aag acc acg agt gag gat gaa aag tgg aag aca ggg aaa     1719
Ala Trp Glu Lys Thr Thr Ser Glu Asp Glu Lys Trp Lys Thr Gly Lys
490                 495                 500                 505

att cag ttg tat caa gga act gat gct acc aaa agc atc att ttt gaa     1767
Ile Gln Leu Tyr Gln Gly Thr Asp Ala Thr Lys Ser Ile Ile Phe Glu
                510                 515                 520

gca gaa cgt ggc aag ggc aaa acc ggc gaa atc gca gtg gat ggc gtc     1815
Ala Glu Arg Gly Lys Gly Lys Thr Gly Glu Ile Ala Val Asp Gly Val
            525                 530                 535

ttg ctt gtt tca ggc tta tgt cca gat agc ctt tta tct gtg gat gac     1863
Leu Leu Val Ser Gly Leu Cys Pro Asp Ser Leu Leu Ser Val Asp Asp
        540                 545                 550
```

-continued

```
tgaatgttac tatctttata tttgactttg tatgtcagtt ccctggtttt tttgatattg   1923

satcatagga cctctggcat tttaaaatta ctaagctgaa aaattgtaat gtaccaacag   1983

aaattattat tgtaagatgc ctttmttgta taagatatgc caatatttgc tttaaatatc   2043

atatcactgt atcttctcag tcatttctga atctttccac attatattat aaaatatgga   2103

aatgtcaggt ttatctcccc tcctcagtat atctgatttg tataagtaag ttgatgagct   2163

tctctctgca acatttctag aaaatagaha aaaaagcaca gagaaatgtt taactgtttg   2223

actcttatga tagtttttgg aaactatgac atcaaagata gacttttgcc taagtggctt   2283

agctgggtct ttcatagcca aacttgtata tttaaattct ttgtaataat aatatccaaa   2343

tcatcaaaaa aaaaaaaaaa aa                                            2365
```

<210> SEQ ID NO 24
<211> LENGTH: 553
<212> TYPE: PRT
<213> ORGANISM: Homo sapiens
<220> FEATURE:
<221> NAME/KEY: VARIANT
<222> LOCATION: (1)...(553)

<400> SEQUENCE: 24

```
Met Pro Leu Pro Trp Ser Leu Ala Leu Pro Leu Leu Leu Ser Trp Val
  1               5                  10                  15

Ala Gly Gly Phe Gly Asn Ala Ala Ser Ala Arg His His Gly Leu Leu
             20                  25                  30

Ala Ser Ala Arg Gln Pro Gly Val Cys His Tyr Gly Thr Lys Leu Ala
         35                  40                  45

Cys Cys Tyr Gly Trp Arg Arg Asn Ser Lys Gly Val Cys Glu Ala Thr
     50                  55                  60

Cys Glu Pro Gly Cys Lys Phe Gly Glu Cys Val Gly Pro Asn Lys Cys
 65                  70                  75                  80

Arg Cys Phe Pro Gly Tyr Thr Gly Lys Thr Cys Ser Gln Asp Val Asn
                 85                  90                  95

Glu Cys Gly Met Lys Pro Arg Pro Cys Gln His Arg Cys Val Asn Thr
            100                 105                 110

His Gly Ser Tyr Lys Cys Phe Cys Leu Ser Gly His Met Leu Met Pro
        115                 120                 125

Asp Ala Thr Cys Val Asn Ser Arg Thr Cys Ala Met Ile Asn Cys Gln
    130                 135                 140

Tyr Ser Cys Glu Asp Thr Glu Glu Gly Pro Gln Cys Leu Cys Pro Ser
145                 150                 155                 160

Ser Gly Leu Arg Leu Ala Pro Asn Gly Arg Asp Cys Leu Asp Ile Asp
                165                 170                 175

Glu Cys Ala Ser Gly Lys Val Ile Cys Pro Tyr Asn Arg Arg Cys Val
            180                 185                 190

Asn Thr Phe Gly Ser Tyr Tyr Cys Lys Cys His Ile Gly Phe Glu Leu
        195                 200                 205

Gln Tyr Ile Ser Gly Arg Tyr Asp Cys Ile Asp Ile Asn Glu Cys Thr
    210                 215                 220

Met Asp Ser His Thr Cys Ser His His Ala Asn Cys Phe Asn Thr Gln
225                 230                 235                 240

Gly Ser Phe Lys Cys Lys Cys Lys Gln Gly Tyr Lys Gly Asn Gly Leu
                245                 250                 255

Arg Cys Ser Ala Ile Pro Glu Asn Ser Val Lys Glu Val Leu Arg Ala
            260                 265                 270
```

-continued

```
Pro Gly Thr Ile Lys Asp Arg Ile Lys Lys Leu Leu Ala His Lys Asn
        275                 280                 285

Ser Met Lys Lys Lys Ala Lys Ile Lys Asn Val Thr Pro Glu Pro Thr
    290                 295                 300

Arg Thr Pro Thr Pro Lys Val Asn Leu Gln Pro Phe Asn Tyr Glu Glu
305                 310                 315                 320

Ile Val Ser Arg Gly Gly Asn Ser His Gly Gly Lys Lys Gly Asn Glu
                325                 330                 335

Glu Lys Met Lys Glu Gly Leu Glu Asp Glu Lys Arg Glu Glu Lys Ala
            340                 345                 350

Leu Lys Asn Asp Ile Glu Glu Arg Ser Leu Arg Gly Asp Val Phe Phe
        355                 360                 365

Pro Lys Val Asn Glu Ala Gly Glu Phe Gly Leu Ile Leu Val Gln Arg
    370                 375                 380

Lys Ala Leu Thr Ser Lys Leu Glu His Lys Asp Leu Asn Ile Ser Val
385                 390                 395                 400

Asp Cys Ser Phe Asn His Gly Ile Cys Asp Trp Lys Gln Asp Arg Glu
                405                 410                 415

Asp Asp Phe Asp Trp Asn Pro Ala Asp Arg Asp Asn Ala Ile Gly Phe
            420                 425                 430

Tyr Met Ala Val Pro Ala Leu Ala Gly His Lys Lys Asp Ile Gly Arg
        435                 440                 445

Leu Lys Leu Leu Leu Pro Asp Leu Gln Pro Gln Ser Asn Phe Cys Leu
    450                 455                 460

Leu Phe Asp Tyr Arg Leu Ala Gly Asp Lys Val Gly Lys Leu Arg Val
465                 470                 475                 480

Phe Val Lys Asn Ser Asn Asn Ala Leu Ala Trp Glu Lys Thr Thr Ser
                485                 490                 495

Glu Asp Glu Lys Trp Lys Thr Gly Lys Ile Gln Leu Tyr Gln Gly Thr
            500                 505                 510

Asp Ala Thr Lys Ser Ile Ile Phe Glu Ala Glu Arg Gly Lys Gly Lys
        515                 520                 525

Thr Gly Glu Ile Ala Val Asp Gly Val Leu Leu Val Ser Gly Leu Cys
    530                 535                 540

Pro Asp Ser Leu Leu Ser Val Asp Asp
545                 550
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 25
ccctggcatg ggagaagacc ac 22

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 26
gtgatatgat atttaaagca aatattggca 30

-continued

<210> SEQ ID NO 27
<211> LENGTH: 2360
<212> TYPE: DNA
<213> ORGANISM: Homo sapiens
<220> FEATURE:
<221> NAME/KEY: CDS
<222> LOCATION: (190)..(1869)
<223> OTHER INFORMATION:
<220> FEATURE:
<221> NAME/KEY: misc_feature
<222> LOCATION: (26)..(26)
<223> OTHER INFORMATION: n = A or T or G or C

<400> SEQUENCE: 27

```
cctctatatg catgctcgag cgcggncgca gtgtgatgga tatctgcaga attcggctta     60

ctcactatag ggctcgagcg gccgcccggg caggtgagga gagaggaggc ggcggcttag    120

ctgctacggg gtccgggccg gcgccctccc gagggggggct caggaggagg aaggaggacc    180

cgtgcgaga atg cct ctg ccc tgg agc ctt gcg ctc ccg ctg ctg ctc tcc    231
          Met Pro Leu Pro Trp Ser Leu Ala Leu Pro Leu Leu Leu Ser
          1               5                   10

tgg gtg gca ggt ggt ttc ggg aac gcg gcc agt gca agg ggt tct cat      279
Trp Val Ala Gly Gly Phe Gly Asn Ala Ala Ser Ala Arg Gly Ser His
15                  20                  25                  30

cat cat cat cat cac ggg ttg tta gca tcg gca cgt cag cct ggg gtc      327
His His His His His Gly Leu Leu Ala Ser Ala Arg Gln Pro Gly Val
                35                  40                  45

tgt cac tat gga act aaa ctg gcc tgc tgc tac ggc tgg aga aga aac      375
Cys His Tyr Gly Thr Lys Leu Ala Cys Cys Tyr Gly Trp Arg Arg Asn
            50                  55                  60

agc aag gga gtc tgt gaa gct aca tgc gaa cct gga tgt aag ttt ggt      423
Ser Lys Gly Val Cys Glu Ala Thr Cys Glu Pro Gly Cys Lys Phe Gly
        65                  70                  75

gag tgc gtg gga cca aac aaa tgc aga tgc ttt cca gga tac acc ggg      471
Glu Cys Val Gly Pro Asn Lys Cys Arg Cys Phe Pro Gly Tyr Thr Gly
    80                  85                  90

aaa acc tgc agt caa gat gtg aat gag tgt gga atg aaa ccc cgg cca      519
Lys Thr Cys Ser Gln Asp Val Asn Glu Cys Gly Met Lys Pro Arg Pro
95                  100                 105                 110

tgc caa cac aga tgt gtg aat aca cac gga agc tac aag tgc ttt tgc      567
Cys Gln His Arg Cys Val Asn Thr His Gly Ser Tyr Lys Cys Phe Cys
                115                 120                 125

ctc agt ggc cac atg ctc atg cca gat gct acg tgt gtg aac tct agg      615
Leu Ser Gly His Met Leu Met Pro Asp Ala Thr Cys Val Asn Ser Arg
            130                 135                 140

aca tgt gcc atg ata aac tgt cag tac agc tgt gaa gac aca gaa gaa      663
Thr Cys Ala Met Ile Asn Cys Gln Tyr Ser Cys Glu Asp Thr Glu Glu
        145                 150                 155

ggg cca cag tgc ctg tgt cca tcc tca gga ctc cgc ctg gcc cca aat      711
Gly Pro Gln Cys Leu Cys Pro Ser Ser Gly Leu Arg Leu Ala Pro Asn
    160                 165                 170

gga aga gac tgt cta gat att gat gaa tgt gcc tct ggt aaa gtc atc      759
Gly Arg Asp Cys Leu Asp Ile Asp Glu Cys Ala Ser Gly Lys Val Ile
175                 180                 185                 190

tgt ccc tac aat cga aga tgt gtg aac aca ttt gga agc tac tac tgc      807
Cys Pro Tyr Asn Arg Arg Cys Val Asn Thr Phe Gly Ser Tyr Tyr Cys
                195                 200                 205

aaa tgt cac att ggt ttc gaa ctg caa tat atc agt gga cga tat gac      855
Lys Cys His Ile Gly Phe Glu Leu Gln Tyr Ile Ser Gly Arg Tyr Asp
            210                 215                 220

tgt ata gat ata aat gaa tgt act atg gat agc cat acg tgc agc cac      903
```

-continued

```
Cys Ile Asp Ile Asn Glu Cys Thr Met Asp Ser His Thr Cys Ser His
        225                 230                 235

cat gcc aat tgc ttc aat acc caa ggg tcc ttc aag tgt aaa tgc aag      951
His Ala Asn Cys Phe Asn Thr Gln Gly Ser Phe Lys Cys Lys Cys Lys
    240                 245                 250

cag gga tat aaa ggc aat gga ctt cgg tgt tct gct atc cct gaa aat      999
Gln Gly Tyr Lys Gly Asn Gly Leu Arg Cys Ser Ala Ile Pro Glu Asn
255                 260                 265                 270

tct gtg aag gaa gtc ctc aga gca cct ggt acc atc aaa gac aga atc     1047
Ser Val Lys Glu Val Leu Arg Ala Pro Gly Thr Ile Lys Asp Arg Ile
                275                 280                 285

aag aag ttg ctt gct cac aaa aac agt atg aaa aag aag gca aaa att     1095
Lys Lys Leu Leu Ala His Lys Asn Ser Met Lys Lys Lys Ala Lys Ile
            290                 295                 300

aaa aat gtt acc cca gaa ccc acc agg act cct acc cct aag gtg aac     1143
Lys Asn Val Thr Pro Glu Pro Thr Arg Thr Pro Thr Pro Lys Val Asn
        305                 310                 315

ttg cag ccc ttc aac tat gaa gag ata gtt tcc aga ggc ggg aac tct     1191
Leu Gln Pro Phe Asn Tyr Glu Glu Ile Val Ser Arg Gly Gly Asn Ser
    320                 325                 330

cat gga ggt aaa aaa ggg aat gaa gag aaa atg aaa gag ggg ctt gag     1239
His Gly Gly Lys Lys Gly Asn Glu Glu Lys Met Lys Glu Gly Leu Glu
335                 340                 345                 350

gat gag aaa aga gaa gag aaa gcc ctg aag aat gac ata gag gag cga     1287
Asp Glu Lys Arg Glu Glu Lys Ala Leu Lys Asn Asp Ile Glu Glu Arg
                355                 360                 365

agc ctg cga gga gat gtg ttt ttc cct aag gtg aat gaa gca ggt gaa     1335
Ser Leu Arg Gly Asp Val Phe Phe Pro Lys Val Asn Glu Ala Gly Glu
            370                 375                 380

ttc ggc ctg att ctg gtc caa agg aaa gcg cta act tcc aaa ctg gaa     1383
Phe Gly Leu Ile Leu Val Gln Arg Lys Ala Leu Thr Ser Lys Leu Glu
        385                 390                 395

cat aaa gat tta aat atc tcg gtt gac tgc agc ttc aat cat ggg atc     1431
His Lys Asp Leu Asn Ile Ser Val Asp Cys Ser Phe Asn His Gly Ile
    400                 405                 410

tgt gac tgg aaa cag gat aga gaa gat gat ttt gac tgg aat cct gct     1479
Cys Asp Trp Lys Gln Asp Arg Glu Asp Asp Phe Asp Trp Asn Pro Ala
415                 420                 425                 430

gat cga gat aat gct att ggc ttc tat atg gca gtt ccg gcc ttg gca     1527
Asp Arg Asp Asn Ala Ile Gly Phe Tyr Met Ala Val Pro Ala Leu Ala
                435                 440                 445

ggt cac aag aaa gac att ggc cga ttg aaa ctt ctc cta cct gac ctg     1575
Gly His Lys Lys Asp Ile Gly Arg Leu Lys Leu Leu Leu Pro Asp Leu
            450                 455                 460

caa ccc caa agc aac ttc tgt ttg ctc ttt gat tac cgg ctg gcc gga     1623
Gln Pro Gln Ser Asn Phe Cys Leu Leu Phe Asp Tyr Arg Leu Ala Gly
        465                 470                 475

gac aaa gtc ggg aaa ctt cga gtg ttt gtg aaa aac agt aac aat gcc     1671
Asp Lys Val Gly Lys Leu Arg Val Phe Val Lys Asn Ser Asn Asn Ala
    480                 485                 490

ctg gca tgg gag aag acc acg agt gag gat gaa aag tgg aag aca ggg     1719
Leu Ala Trp Glu Lys Thr Thr Ser Glu Asp Glu Lys Trp Lys Thr Gly
495                 500                 505                 510

aaa att cag ttg tat caa gga act gat gct acc aaa agc atc att ttt     1767
Lys Ile Gln Leu Tyr Gln Gly Thr Asp Ala Thr Lys Ser Ile Ile Phe
                515                 520                 525

gaa gca gaa cgt ggc aag ggc aaa acc ggc gaa atc gca gtg gat ggc     1815
Glu Ala Glu Arg Gly Lys Gly Lys Thr Gly Glu Ile Ala Val Asp Gly
            530                 535                 540
```

-continued

```
gtc ttg ctt gtt tca ggc tta tgt cca gat agc ctt tta tct gtg gat      1863
Val Leu Leu Val Ser Gly Leu Cys Pro Asp Ser Leu Leu Ser Val Asp
        545                 550                 555

gac tga atgttactat ctttatattt gactttgtat gtcagttccc tggttttttt      1919
Asp

gatattgcat cataggacct ctggcatttt agaattacta gctgaaaaat tgtaatgtac   1979

caacagaaat attattgtaa gatgcctttc ttgtataaga tatgccaata tttgctttaa   2039

atatcatatc actgtatctt ctcagtcatt tctgaatctt tccacattat attataaaat   2099

atggaaatgt cagtttatct cccctcctca gtatatctga tttgtataag taagttgatg   2159

agcttctctc tacaacattt ctagaaaata gaaaaaaaag cacagagaaa tgtttaactg   2219

tttgactctt atgatacttc ttggaaacta tgacatcaaa gatagacttt tgcctaagtg   2279

gcttagctgg gtctttcata gccaaacttg tatatttaaa ttctttgtaa taataatatc   2339

caaatcatca aaaaaaaaaa a                                              2360


<210> SEQ ID NO 28
<211> LENGTH: 559
<212> TYPE: PRT
<213> ORGANISM: Homo sapiens

<400> SEQUENCE: 28

Met Pro Leu Pro Trp Ser Leu Ala Leu Pro Leu Leu Leu Ser Trp Val
1               5                   10                  15

Ala Gly Gly Phe Gly Asn Ala Ala Ser Ala Arg Gly Ser His His His
            20                  25                  30

His His His Gly Leu Leu Ala Ser Ala Arg Gln Pro Gly Val Cys His
        35                  40                  45

Tyr Gly Thr Lys Leu Ala Cys Cys Tyr Gly Trp Arg Arg Asn Ser Lys
    50                  55                  60

Gly Val Cys Glu Ala Thr Cys Glu Pro Gly Cys Lys Phe Gly Glu Cys
65                  70                  75                  80

Val Gly Pro Asn Lys Cys Arg Cys Phe Pro Gly Tyr Thr Gly Lys Thr
                85                  90                  95

Cys Ser Gln Asp Val Asn Glu Cys Gly Met Lys Pro Arg Pro Cys Gln
            100                 105                 110

His Arg Cys Val Asn Thr His Gly Ser Tyr Lys Cys Phe Cys Leu Ser
        115                 120                 125

Gly His Met Leu Met Pro Asp Ala Thr Cys Val Asn Ser Arg Thr Cys
    130                 135                 140

Ala Met Ile Asn Cys Gln Tyr Ser Cys Glu Asp Thr Glu Glu Gly Pro
145                 150                 155                 160

Gln Cys Leu Cys Pro Ser Ser Gly Leu Arg Leu Ala Pro Asn Gly Arg
                165                 170                 175

Asp Cys Leu Asp Ile Asp Glu Cys Ala Ser Gly Lys Val Ile Cys Pro
            180                 185                 190

Tyr Asn Arg Arg Cys Val Asn Thr Phe Gly Ser Tyr Tyr Cys Lys Cys
        195                 200                 205

His Ile Gly Phe Glu Leu Gln Tyr Ile Ser Gly Arg Tyr Asp Cys Ile
    210                 215                 220

Asp Ile Asn Glu Cys Thr Met Asp Ser His Thr Cys Ser His His Ala
225                 230                 235                 240

Asn Cys Phe Asn Thr Gln Gly Ser Phe Lys Cys Lys Cys Lys Gln Gly
                245                 250                 255
```

-continued

```
Tyr Lys Gly Asn Gly Leu Arg Cys Ser Ala Ile Pro Glu Asn Ser Val
            260                 265                 270

Lys Glu Val Leu Arg Ala Pro Gly Thr Ile Lys Asp Arg Ile Lys Lys
        275                 280                 285

Leu Leu Ala His Lys Asn Ser Met Lys Lys Lys Ala Lys Ile Lys Asn
    290                 295                 300

Val Thr Pro Glu Pro Thr Arg Thr Pro Thr Pro Lys Val Asn Leu Gln
305                 310                 315                 320

Pro Phe Asn Tyr Glu Glu Ile Val Ser Arg Gly Gly Asn Ser His Gly
                325                 330                 335

Gly Lys Lys Gly Asn Glu Glu Lys Met Lys Glu Gly Leu Glu Asp Glu
            340                 345                 350

Lys Arg Glu Glu Lys Ala Leu Lys Asn Asp Ile Glu Glu Arg Ser Leu
        355                 360                 365

Arg Gly Asp Val Phe Phe Pro Lys Val Asn Glu Ala Gly Glu Phe Gly
    370                 375                 380

Leu Ile Leu Val Gln Arg Lys Ala Leu Thr Ser Lys Leu Glu His Lys
385                 390                 395                 400

Asp Leu Asn Ile Ser Val Asp Cys Ser Phe Asn His Gly Ile Cys Asp
                405                 410                 415

Trp Lys Gln Asp Arg Glu Asp Asp Phe Asp Trp Asn Pro Ala Asp Arg
            420                 425                 430

Asp Asn Ala Ile Gly Phe Tyr Met Ala Val Pro Ala Leu Ala Gly His
        435                 440                 445

Lys Lys Asp Ile Gly Arg Leu Lys Leu Leu Leu Pro Asp Leu Gln Pro
    450                 455                 460

Gln Ser Asn Phe Cys Leu Leu Phe Asp Tyr Arg Leu Ala Gly Asp Lys
465                 470                 475                 480

Val Gly Lys Leu Arg Val Phe Val Lys Asn Ser Asn Asn Ala Leu Ala
                485                 490                 495

Trp Glu Lys Thr Thr Ser Glu Asp Glu Lys Trp Lys Thr Gly Lys Ile
            500                 505                 510

Gln Leu Tyr Gln Gly Thr Asp Ala Thr Lys Ser Ile Ile Phe Glu Ala
        515                 520                 525

Glu Arg Gly Lys Gly Lys Thr Gly Glu Ile Ala Val Asp Gly Val Leu
    530                 535                 540

Leu Val Ser Gly Leu Cys Pro Asp Ser Leu Leu Ser Val Asp Asp
545                 550                 555


<210> SEQ ID NO 29
<211> LENGTH: 2345
<212> TYPE: DNA
<213> ORGANISM: Homo sapiens
<220> FEATURE:
<221> NAME/KEY: CDS
<222> LOCATION: (190)..(1854)
<220> FEATURE:
<221> NAME/KEY: misc_feature
<222> LOCATION: (26)...(26)
<223> OTHER INFORMATION: n = a,t,c or g

<400> SEQUENCE: 29

cctctatatg catgctcgag cgcggncgca gtgtgatgga tatctgcaga attcggctta     60

ctcactatag ggctcgagcg gccgcccggg caggtgagga gagaggaggc ggcggcttag    120

ctgctacggg gtccgggccg gcgccctccc gagggggggct caggaggagg aaggaggacc    180

cgtgcgaga atg cct ctg ccc tgg agc ctt gcg ctc ccg ctg ctg ctc tcc    231
```

-continued

```
        Met Pro Leu Pro Trp Ser Leu Ala Leu Pro Leu Leu Leu Ser
        1               5                   10

tgg gtg gca ggt ggt ttc ggg aac gcg gcc agt gca agg cat cat cac      279
Trp Val Ala Gly Gly Phe Gly Asn Ala Ala Ser Ala Arg His His His
15                  20                  25                  30

ggg ttg tta gca tcg gca cgt cag cct ggg gtc tgt cac tat gga act      327
Gly Leu Leu Ala Ser Ala Arg Gln Pro Gly Val Cys His Tyr Gly Thr
                35                  40                  45

aaa ctg gcc tgc tgc tac ggc tgg aga aga aac agc aag gga gtc tgt      375
Lys Leu Ala Cys Cys Tyr Gly Trp Arg Arg Asn Ser Lys Gly Val Cys
            50                  55                  60

gaa gct aca tgc gaa cct gga tgt aag ttt ggt gag tgc gtg gga cca      423
Glu Ala Thr Cys Glu Pro Gly Cys Lys Phe Gly Glu Cys Val Gly Pro
        65                  70                  75

aac aaa tgc aga tgc ttt cca gga tac acc ggg aaa acc tgc agt caa      471
Asn Lys Cys Arg Cys Phe Pro Gly Tyr Thr Gly Lys Thr Cys Ser Gln
    80                  85                  90

gat gtg aat gag tgt gga atg aaa ccc cgg cca tgc caa cac aga tgt      519
Asp Val Asn Glu Cys Gly Met Lys Pro Arg Pro Cys Gln His Arg Cys
95                  100                 105                 110

gtg aat aca cac gga agc tac aag tgc ttt tgc ctc agt ggc cac atg      567
Val Asn Thr His Gly Ser Tyr Lys Cys Phe Cys Leu Ser Gly His Met
                115                 120                 125

ctc atg cca gat gct acg tgt gtg aac tct agg aca tgt gcc atg ata      615
Leu Met Pro Asp Ala Thr Cys Val Asn Ser Arg Thr Cys Ala Met Ile
            130                 135                 140

aac tgt cag tac agc tgt gaa gac aca gaa gaa ggg cca cag tgc ctg      663
Asn Cys Gln Tyr Ser Cys Glu Asp Thr Glu Glu Gly Pro Gln Cys Leu
        145                 150                 155

tgt cca tcc tca gga ctc cgc ctg gcc cca aat gga aga gac tgt cta      711
Cys Pro Ser Ser Gly Leu Arg Leu Ala Pro Asn Gly Arg Asp Cys Leu
    160                 165                 170

gat att gat gaa tgt gcc tct ggt aaa gtc atc tgt ccc tac aat cga      759
Asp Ile Asp Glu Cys Ala Ser Gly Lys Val Ile Cys Pro Tyr Asn Arg
175                 180                 185                 190

aga tgt gtg aac aca ttt gga agc tac tac tgc aaa tgt cac att ggt      807
Arg Cys Val Asn Thr Phe Gly Ser Tyr Tyr Cys Lys Cys His Ile Gly
                195                 200                 205

ttc gaa ctg caa tat atc agt gga cga tat gac tgt ata gat ata aat      855
Phe Glu Leu Gln Tyr Ile Ser Gly Arg Tyr Asp Cys Ile Asp Ile Asn
            210                 215                 220

gaa tgt act atg gat agc cat acg tgc agc cac cat gcc aat tgc ttc      903
Glu Cys Thr Met Asp Ser His Thr Cys Ser His His Ala Asn Cys Phe
        225                 230                 235

aat acc caa ggg tcc ttc aag tgt aaa tgc aag cag gga tat aaa ggc      951
Asn Thr Gln Gly Ser Phe Lys Cys Lys Cys Lys Gln Gly Tyr Lys Gly
    240                 245                 250

aat gga ctt cgg tgt tct gct atc cct gaa aat tct gtg aag gaa gtc      999
Asn Gly Leu Arg Cys Ser Ala Ile Pro Glu Asn Ser Val Lys Glu Val
255                 260                 265                 270

ctc aga gca cct ggt acc atc aaa gac aga atc aag aag ttg ctt gct     1047
Leu Arg Ala Pro Gly Thr Ile Lys Asp Arg Ile Lys Lys Leu Leu Ala
                275                 280                 285

cac aaa aac agt atg aaa aag aag gca aaa att aaa aat gtt acc cca     1095
His Lys Asn Ser Met Lys Lys Lys Ala Lys Ile Lys Asn Val Thr Pro
            290                 295                 300

gaa ccc acc agg act cct acc cct aag gtg aac ttg cag ccc ttc aac     1143
Glu Pro Thr Arg Thr Pro Thr Pro Lys Val Asn Leu Gln Pro Phe Asn
        305                 310                 315
```

-continued

```
tat gaa gag ata gtt tcc aga ggc ggg aac tct cat gga ggt aaa aaa      1191
Tyr Glu Glu Ile Val Ser Arg Gly Gly Asn Ser His Gly Gly Lys Lys
    320                 325                 330

ggg aat gaa gag aaa atg aaa gag ggg ctt gag gat gag aaa aga gaa      1239
Gly Asn Glu Glu Lys Met Lys Glu Gly Leu Glu Asp Glu Lys Arg Glu
335                 340                 345                 350

gag aaa gcc ctg aag aat gac ata gag gag cga agc ctg cga gga gat      1287
Glu Lys Ala Leu Lys Asn Asp Ile Glu Glu Arg Ser Leu Arg Gly Asp
                355                 360                 365

gtg ttt ttc cct aag gtg aat gaa gca ggt gaa ttc ggc ctg att ctg      1335
Val Phe Phe Pro Lys Val Asn Glu Ala Gly Glu Phe Gly Leu Ile Leu
            370                 375                 380

gtc caa agg aaa gcg cta act tcc aaa ctg gaa cat aaa gat tta aat      1383
Val Gln Arg Lys Ala Leu Thr Ser Lys Leu Glu His Lys Asp Leu Asn
        385                 390                 395

atc tcg gtt gac tgc agc ttc aat cat ggg atc tgt gac tgg aaa cag      1431
Ile Ser Val Asp Cys Ser Phe Asn His Gly Ile Cys Asp Trp Lys Gln
    400                 405                 410

gat aga gaa gat gat ttt gac tgg aat cct gct gat cga gat aat gct      1479
Asp Arg Glu Asp Asp Phe Asp Trp Asn Pro Ala Asp Arg Asp Asn Ala
415                 420                 425                 430

att ggc ttc tat atg gca gtt ccg gcc ttg gca ggt cac aag aaa gac      1527
Ile Gly Phe Tyr Met Ala Val Pro Ala Leu Ala Gly His Lys Lys Asp
                435                 440                 445

att ggc cga ttg aaa ctt ctc cta cct gac ctg caa ccc caa agc aac      1575
Ile Gly Arg Leu Lys Leu Leu Leu Pro Asp Leu Gln Pro Gln Ser Asn
            450                 455                 460

ttc tgt ttg ctc ttt gat tac cgg ctg gcc gga gac aaa gtc ggg aaa      1623
Phe Cys Leu Leu Phe Asp Tyr Arg Leu Ala Gly Asp Lys Val Gly Lys
        465                 470                 475

ctt cga gtg ttt gtg aaa aac agt aac aat gcc ctg gca tgg gag aag      1671
Leu Arg Val Phe Val Lys Asn Ser Asn Asn Ala Leu Ala Trp Glu Lys
    480                 485                 490

acc acg agt gag gat gaa aag tgg aag aca ggg aaa att cag ttg tat      1719
Thr Thr Ser Glu Asp Glu Lys Trp Lys Thr Gly Lys Ile Gln Leu Tyr
495                 500                 505                 510

caa gga act gat gct acc aaa agc atc att ttt gaa gca gaa cgt ggc      1767
Gln Gly Thr Asp Ala Thr Lys Ser Ile Ile Phe Glu Ala Glu Arg Gly
                515                 520                 525

aag ggc aaa acc ggc gaa atc gca gtg gat ggc gtc ttg ctt gtt tca      1815
Lys Gly Lys Thr Gly Glu Ile Ala Val Asp Gly Val Leu Leu Val Ser
            530                 535                 540

ggc tta tgt cca gat agc ctt tta tct gtg gat gac tga atgttactat      1864
Gly Leu Cys Pro Asp Ser Leu Leu Ser Val Asp Asp
        545                 550

ctttatattt gactttgtat gtcagttccc tggttttttt gatattgcat cataggacct   1924

ctggcatttt agaattacta gctgaaaaat tgtaatgtac caacagaaat attattgtaa   1984

gatgcctttc ttgtataaga tatgccaata tttgctttaa atatcatatc actgtatctt   2044

ctcagtcatt tctgaatctt tccacattat attataaaat atggaaatgt cagtttatct   2104

cccctcctca gtatatctga tttgtataag taagttgatg agcttctctc tacaacattt   2164

ctagaaaata gaaaaaaaag cacagagaaa tgtttaactg tttgactctt atgatacttc   2224

ttggaaacta tgacatcaaa gatagacttt tgcctaagtg gcttagctgg gtctttcata   2284

gccaaacttg tatatttaaa ttctttgtaa taataatatc caaatcatca aaaaaaaaaa   2344

a                                                                   2345
```

-continued

<210> SEQ ID NO 30
<211> LENGTH: 554
<212> TYPE: PRT
<213> ORGANISM: Homo sapiens

<400> SEQUENCE: 30

```
Met Pro Leu Pro Trp Ser Leu Ala Leu Pro Leu Leu Leu Ser Trp Val
1               5                   10                  15

Ala Gly Gly Phe Gly Asn Ala Ala Ser Ala Arg His His His Gly Leu
            20                  25                  30

Leu Ala Ser Ala Arg Gln Pro Gly Val Cys His Tyr Gly Thr Lys Leu
        35                  40                  45

Ala Cys Cys Tyr Gly Trp Arg Arg Asn Ser Lys Gly Val Cys Glu Ala
    50                  55                  60

Thr Cys Glu Pro Gly Cys Lys Phe Gly Glu Cys Val Gly Pro Asn Lys
65                  70                  75                  80

Cys Arg Cys Phe Pro Gly Tyr Thr Gly Lys Thr Cys Ser Gln Asp Val
                85                  90                  95

Asn Glu Cys Gly Met Lys Pro Arg Pro Cys Gln His Arg Cys Val Asn
            100                 105                 110

Thr His Gly Ser Tyr Lys Cys Phe Cys Leu Ser Gly His Met Leu Met
        115                 120                 125

Pro Asp Ala Thr Cys Val Asn Ser Arg Thr Cys Ala Met Ile Asn Cys
    130                 135                 140

Gln Tyr Ser Cys Glu Asp Thr Glu Glu Gly Pro Gln Cys Leu Cys Pro
145                 150                 155                 160

Ser Ser Gly Leu Arg Leu Ala Pro Asn Gly Arg Asp Cys Leu Asp Ile
                165                 170                 175

Asp Glu Cys Ala Ser Gly Lys Val Ile Cys Pro Tyr Asn Arg Arg Cys
            180                 185                 190

Val Asn Thr Phe Gly Ser Tyr Tyr Cys Lys Cys His Ile Gly Phe Glu
        195                 200                 205

Leu Gln Tyr Ile Ser Gly Arg Tyr Asp Cys Ile Asp Ile Asn Glu Cys
    210                 215                 220

Thr Met Asp Ser His Thr Cys Ser His His Ala Asn Cys Phe Asn Thr
225                 230                 235                 240

Gln Gly Ser Phe Lys Cys Lys Cys Lys Gln Gly Tyr Lys Gly Asn Gly
                245                 250                 255

Leu Arg Cys Ser Ala Ile Pro Glu Asn Ser Val Lys Glu Val Leu Arg
            260                 265                 270

Ala Pro Gly Thr Ile Lys Asp Arg Ile Lys Lys Leu Leu Ala His Lys
        275                 280                 285

Asn Ser Met Lys Lys Lys Ala Lys Ile Lys Asn Val Thr Pro Glu Pro
    290                 295                 300

Thr Arg Thr Pro Thr Pro Lys Val Asn Leu Gln Pro Phe Asn Tyr Glu
305                 310                 315                 320

Glu Ile Val Ser Arg Gly Gly Asn Ser His Gly Gly Lys Lys Gly Asn
                325                 330                 335

Glu Glu Lys Met Lys Glu Gly Leu Glu Asp Glu Lys Arg Glu Glu Lys
            340                 345                 350

Ala Leu Lys Asn Asp Ile Glu Glu Arg Ser Leu Arg Gly Asp Val Phe
        355                 360                 365

Phe Pro Lys Val Asn Glu Ala Gly Glu Phe Gly Leu Ile Leu Val Gln
    370                 375                 380
```

-continued

```
Arg Lys Ala Leu Thr Ser Lys Leu Glu His Lys Asp Leu Asn Ile Ser
385                 390                 395                 400

Val Asp Cys Ser Phe Asn His Gly Ile Cys Asp Trp Lys Gln Asp Arg
                405                 410                 415

Glu Asp Asp Phe Asp Trp Asn Pro Ala Asp Arg Asp Asn Ala Ile Gly
            420                 425                 430

Phe Tyr Met Ala Val Pro Ala Leu Ala Gly His Lys Lys Asp Ile Gly
        435                 440                 445

Arg Leu Lys Leu Leu Leu Pro Asp Leu Gln Pro Gln Ser Asn Phe Cys
    450                 455                 460

Leu Leu Phe Asp Tyr Arg Leu Ala Gly Asp Lys Val Gly Lys Leu Arg
465                 470                 475                 480

Val Phe Val Lys Asn Ser Asn Asn Ala Leu Ala Trp Glu Lys Thr Thr
                485                 490                 495

Ser Glu Asp Glu Lys Trp Lys Thr Gly Lys Ile Gln Leu Tyr Gln Gly
            500                 505                 510

Thr Asp Ala Thr Lys Ser Ile Ile Phe Glu Ala Glu Arg Gly Lys Gly
        515                 520                 525

Lys Thr Gly Glu Ile Ala Val Asp Gly Val Leu Leu Val Ser Gly Leu
    530                 535                 540

Cys Pro Asp Ser Leu Leu Ser Val Asp Asp
545                 550


<210> SEQ ID NO 31
<211> LENGTH: 2413
<212> TYPE: DNA
<213> ORGANISM: Homo sapiens
<220> FEATURE:
<221> NAME/KEY: CDS
<222> LOCATION: (258)..(1922)

<400> SEQUENCE: 31

aagctggtac gcctgcaggt accggtccgg aattcccggg tcgacgattt cgtcccagcc      60

cctccccagg ccgcgagcgc ccctgccgcg gtgcctggcc tcccctccca gactgcaggg     120

acagcacccg gtaactgcga gtggagcgga ggacccgagc ggctgaggag agaggaggcg     180

gcggcttagc tgctacgggg tccggccggc gccctcccga gggggctca ggaggaggaa     240

ggaggacccg tgcgaga atg cct ctg ccc tgg agc ctt gcg ctc ccg ctg       290
                   Met Pro Leu Pro Trp Ser Leu Ala Leu Pro Leu
                    1               5                   10

ctg ctc tcc tgg gtg gca ggt ggt ttc ggg aac gcg gcc agt gca agg      338
Leu Leu Ser Trp Val Ala Gly Gly Phe Gly Asn Ala Ala Ser Ala Arg
            15                  20                  25

cat cac ggg ttg tta gca tcg gca cgt cag cct ggg gtc tgt cac tat      386
His His Gly Leu Leu Ala Ser Ala Arg Gln Pro Gly Val Cys His Tyr
        30                  35                  40

gga act aaa ctg gcc tgc tgc tac ggc tgg aga aga aac agc aag gga      434
Gly Thr Lys Leu Ala Cys Cys Tyr Gly Trp Arg Arg Asn Ser Lys Gly
     45                  50                  55

gtc tgt gaa gct aca tgc gaa cct gga tgt aag ttt ggt gag tgc gtg      482
Val Cys Glu Ala Thr Cys Glu Pro Gly Cys Lys Phe Gly Glu Cys Val
 60                  65                  70                  75

gga cca aac aaa tgc aga tgc ttt cca gga tac acc ggg aaa acc tgc      530
Gly Pro Asn Lys Cys Arg Cys Phe Pro Gly Tyr Thr Gly Lys Thr Cys
                80                  85                  90

agt caa gat gtg aat gag tgt gga atg aaa ccc cgg cca tgc caa cac      578
Ser Gln Asp Val Asn Glu Cys Gly Met Lys Pro Arg Pro Cys Gln His
            95                 100                 105
```

-continued

```
aga tgt gtg aat aca cac gga agc tac aag tgc ttt tgc ctc agt ggc      626
Arg Cys Val Asn Thr His Gly Ser Tyr Lys Cys Phe Cys Leu Ser Gly
        110                 115                 120

cac atg ctc atg cca gat gct acg tgt gtg aac tct agg aca tgt gcc      674
His Met Leu Met Pro Asp Ala Thr Cys Val Asn Ser Arg Thr Cys Ala
    125                 130                 135

atg ata aac tgt cag tac agc tgt gaa gac aca gaa gaa ggg cca cag      722
Met Ile Asn Cys Gln Tyr Ser Cys Glu Asp Thr Glu Glu Gly Pro Gln
140                 145                 150                 155

tgc ctg tgt cca tcc tca gga ctc cgc ctg gcc cca aat gga aga gac      770
Cys Leu Cys Pro Ser Ser Gly Leu Arg Leu Ala Pro Asn Gly Arg Asp
                160                 165                 170

tgt cta gat att gat gaa tgt gcc tct ggt aaa gtc atc tgt ccc tac      818
Cys Leu Asp Ile Asp Glu Cys Ala Ser Gly Lys Val Ile Cys Pro Tyr
            175                 180                 185

aat cga aga tgt gtg aac aca ttt gga agc tac tac tgc aaa tgt cac      866
Asn Arg Arg Cys Val Asn Thr Phe Gly Ser Tyr Tyr Cys Lys Cys His
        190                 195                 200

att ggt ttc gaa ctg caa tat atc agt gga cga tat gac tgt ata gat      914
Ile Gly Phe Glu Leu Gln Tyr Ile Ser Gly Arg Tyr Asp Cys Ile Asp
    205                 210                 215

ata aat gaa tgt act atg gat agc cat acg tgc agc cac cat gcc aat      962
Ile Asn Glu Cys Thr Met Asp Ser His Thr Cys Ser His His Ala Asn
220                 225                 230                 235

tgc ttc aat acc caa ggg tcc ttc aag tgt aaa tgc aag cag gga tat     1010
Cys Phe Asn Thr Gln Gly Ser Phe Lys Cys Lys Cys Lys Gln Gly Tyr
                240                 245                 250

aaa ggc aat gga ctt cgg tgt tct gct atc cct gaa aat tct gtg aag     1058
Lys Gly Asn Gly Leu Arg Cys Ser Ala Ile Pro Glu Asn Ser Val Lys
            255                 260                 265

gaa gtc ctc aga gca cct ggt acc atc aaa gac aga atc aag aag ttg     1106
Glu Val Leu Arg Ala Pro Gly Thr Ile Lys Asp Arg Ile Lys Lys Leu
        270                 275                 280

ctt gct cac aaa aac agc atg aaa aag aag gca aaa att aaa aat gtt     1154
Leu Ala His Lys Asn Ser Met Lys Lys Lys Ala Lys Ile Lys Asn Val
    285                 290                 295

acc cca gaa ccc acc agg act cct acc cct aag gtg aac ttg cag ccc     1202
Thr Pro Glu Pro Thr Arg Thr Pro Thr Pro Lys Val Asn Leu Gln Pro
300                 305                 310                 315

ttc aac tat gaa gag ata gtt tcc aga ggc ggg aac tct cat gga ggt     1250
Phe Asn Tyr Glu Glu Ile Val Ser Arg Gly Gly Asn Ser His Gly Gly
                320                 325                 330

aaa aaa ggg aat gaa gag aaa atg aaa gag ggg ctt gag gat gag aaa     1298
Lys Lys Gly Asn Glu Glu Lys Met Lys Glu Gly Leu Glu Asp Glu Lys
            335                 340                 345

aga gaa gag aaa gcc ctg aag aat gac ata gag gag cga agc ctg cga     1346
Arg Glu Glu Lys Ala Leu Lys Asn Asp Ile Glu Glu Arg Ser Leu Arg
        350                 355                 360

gga gat gtg ttt ttc cct aag gtg aat gaa gca ggt gaa ttc ggc ctg     1394
Gly Asp Val Phe Phe Pro Lys Val Asn Glu Ala Gly Glu Phe Gly Leu
    365                 370                 375

att ctg gtc caa agg aaa gcg cta act tcc aaa ctg gaa cat aaa gca     1442
Ile Leu Val Gln Arg Lys Ala Leu Thr Ser Lys Leu Glu His Lys Ala
380                 385                 390                 395

gat tta aat atc tcg gtt gac tgc agc ttc aat cat ggg atc tgt gac     1490
Asp Leu Asn Ile Ser Val Asp Cys Ser Phe Asn His Gly Ile Cys Asp
                400                 405                 410

tgg aaa cag gat aga gaa gat gat ttt gac tgg aat cct gct gat cga     1538
Trp Lys Gln Asp Arg Glu Asp Asp Phe Asp Trp Asn Pro Ala Asp Arg
```

-continued

```
            415                 420                 425

gat aat gct att ggc ttc tat atg gca gtt ccg gcc ttg gca ggt cac     1586
Asp Asn Ala Ile Gly Phe Tyr Met Ala Val Pro Ala Leu Ala Gly His
        430                 435                 440

aag aaa gac att ggc cga ttg aaa ctt ctc cta cct gac ctg caa ccc     1634
Lys Lys Asp Ile Gly Arg Leu Lys Leu Leu Leu Pro Asp Leu Gln Pro
    445                 450                 455

caa agc aac ttc tgt ttg ctc ttt gat tac cgg ctg gcc gga gac aaa     1682
Gln Ser Asn Phe Cys Leu Leu Phe Asp Tyr Arg Leu Ala Gly Asp Lys
460                 465                 470                 475

gtc ggg aaa ctt cga gtg ttt gtg aaa aac agt aac aat gcc ctg gca     1730
Val Gly Lys Leu Arg Val Phe Val Lys Asn Ser Asn Asn Ala Leu Ala
              480                 485                 490

tgg gag aag acc acg agt gag gat gaa aag tgg aag aca ggg aaa att     1778
Trp Glu Lys Thr Thr Ser Glu Asp Glu Lys Trp Lys Thr Gly Lys Ile
            495                 500                 505

cag ttg tat caa gga act gat gct acc aaa agc atc att ttt gaa gca     1826
Gln Leu Tyr Gln Gly Thr Asp Ala Thr Lys Ser Ile Ile Phe Glu Ala
        510                 515                 520

gaa cgt ggc aag ggc aaa acc ggc gaa atc gca gtg gat ggc gtc ttg     1874
Glu Arg Gly Lys Gly Lys Thr Gly Glu Ile Ala Val Asp Gly Val Leu
    525                 530                 535

ctt gtt tca ggc tta tgt cca gat agc ctt tta tct gtg gat gac tga     1922
Leu Val Ser Gly Leu Cys Pro Asp Ser Leu Leu Ser Val Asp Asp
540                 545                 550

atgttactat ctttatattt gactttgtat gtcagttccc tggttttttt gatattgcat   1982

cataggacct ctggcatttt agaattacta gctgaaaaat tgtaatgtac caacagaaat   2042

attattgtaa gatgcctttc ttgtataaga tatgccaata tttgctttaa atatcatatc   2102

actgtatctt ctcagtcatt tctgaatctt tccacattat attataaaat atggaaatgt   2162

cagtttatct cccctcctca gtatatctga tttgtataag taagttgatg agcttctctc   2222

tacaacattt ctagaaaata gaaaaaaaag cacagagaaa tgtttaactg tttgactctt   2282

atgatacttc ttggaaacta tgacatcaaa gatagacttt tgcctaagtg gcttagctgg   2342

gtctttcata gccaaacttg tatatttaaa ttctttgtaa taataatatc caaatcatca   2402

aaaaaaaaaa a                                                        2413


<210> SEQ ID NO 32
<211> LENGTH: 554
<212> TYPE: PRT
<213> ORGANISM: Homo sapiens

<400> SEQUENCE: 32

Met Pro Leu Pro Trp Ser Leu Ala Leu Pro Leu Leu Leu Ser Trp Val
  1               5                  10                  15

Ala Gly Gly Phe Gly Asn Ala Ala Ser Ala Arg His His Gly Leu Leu
            20                  25                  30

Ala Ser Ala Arg Gln Pro Gly Val Cys His Tyr Gly Thr Lys Leu Ala
        35                  40                  45

Cys Cys Tyr Gly Trp Arg Arg Asn Ser Lys Gly Val Cys Glu Ala Thr
     50                  55                  60

Cys Glu Pro Gly Cys Lys Phe Gly Glu Cys Val Gly Pro Asn Lys Cys
 65                  70                  75                  80

Arg Cys Phe Pro Gly Tyr Thr Gly Lys Thr Cys Ser Gln Asp Val Asn
                 85                  90                  95

Glu Cys Gly Met Lys Pro Arg Pro Cys Gln His Arg Cys Val Asn Thr
```

-continued

```
            100                 105                 110

His Gly Ser Tyr Lys Cys Phe Cys Leu Ser Gly His Met Leu Met Pro
        115                 120                 125

Asp Ala Thr Cys Val Asn Ser Arg Thr Cys Ala Met Ile Asn Cys Gln
    130                 135                 140

Tyr Ser Cys Glu Asp Thr Glu Glu Gly Pro Gln Cys Leu Cys Pro Ser
145                 150                 155                 160

Ser Gly Leu Arg Leu Ala Pro Asn Gly Arg Asp Cys Leu Asp Ile Asp
                165                 170                 175

Glu Cys Ala Ser Gly Lys Val Ile Cys Pro Tyr Asn Arg Arg Cys Val
            180                 185                 190

Asn Thr Phe Gly Ser Tyr Tyr Cys Lys Cys His Ile Gly Phe Glu Leu
        195                 200                 205

Gln Tyr Ile Ser Gly Arg Tyr Asp Cys Ile Asp Ile Asn Glu Cys Thr
    210                 215                 220

Met Asp Ser His Thr Cys Ser His His Ala Asn Cys Phe Asn Thr Gln
225                 230                 235                 240

Gly Ser Phe Lys Cys Lys Cys Lys Gln Gly Tyr Lys Gly Asn Gly Leu
                245                 250                 255

Arg Cys Ser Ala Ile Pro Glu Asn Ser Val Lys Glu Val Leu Arg Ala
            260                 265                 270

Pro Gly Thr Ile Lys Asp Arg Ile Lys Lys Leu Leu Ala His Lys Asn
        275                 280                 285

Ser Met Lys Lys Lys Ala Lys Ile Lys Asn Val Thr Pro Glu Pro Thr
    290                 295                 300

Arg Thr Pro Thr Pro Lys Val Asn Leu Gln Pro Phe Asn Tyr Glu Glu
305                 310                 315                 320

Ile Val Ser Arg Gly Gly Asn Ser His Gly Gly Lys Lys Gly Asn Glu
                325                 330                 335

Glu Lys Met Lys Glu Gly Leu Glu Asp Glu Lys Arg Glu Glu Lys Ala
            340                 345                 350

Leu Lys Asn Asp Ile Glu Glu Arg Ser Leu Arg Gly Asp Val Phe Phe
        355                 360                 365

Pro Lys Val Asn Glu Ala Gly Glu Phe Gly Leu Ile Leu Val Gln Arg
    370                 375                 380

Lys Ala Leu Thr Ser Lys Leu Glu His Lys Ala Asp Leu Asn Ile Ser
385                 390                 395                 400

Val Asp Cys Ser Phe Asn His Gly Ile Cys Asp Trp Lys Gln Asp Arg
                405                 410                 415

Glu Asp Asp Phe Asp Trp Asn Pro Ala Asp Arg Asp Asn Ala Ile Gly
            420                 425                 430

Phe Tyr Met Ala Val Pro Ala Leu Ala Gly His Lys Lys Asp Ile Gly
        435                 440                 445

Arg Leu Lys Leu Leu Leu Pro Asp Leu Gln Pro Gln Ser Asn Phe Cys
    450                 455                 460

Leu Leu Phe Asp Tyr Arg Leu Ala Gly Asp Lys Val Gly Lys Leu Arg
465                 470                 475                 480

Val Phe Val Lys Asn Ser Asn Asn Ala Leu Ala Trp Glu Lys Thr Thr
                485                 490                 495

Ser Glu Asp Glu Lys Trp Lys Thr Gly Lys Ile Gln Leu Tyr Gln Gly
            500                 505                 510

Thr Asp Ala Thr Lys Ser Ile Ile Phe Glu Ala Glu Arg Gly Lys Gly
        515                 520                 525
```

-continued

```
Lys Thr Gly Glu Ile Ala Val Asp Gly Val Leu Leu Val Ser Gly Leu
    530                 535                 540

Cys Pro Asp Ser Leu Leu Ser Val Asp Asp
545                 550
```

METHOD OF DETECTING A CANCEROUS CELL EXPRESSING AN EGF MOTIF POLYNUCLEOTIDE

1. RELATED APPLICATIONS

This patent application is a continuation of U.S. patent application Ser. No. 09/981,649 filed Oct. 15, 2001, which is a continuation-in-pan of U.S. patent application Ser. No. 09/687,860 tiled Oct. 13, 2000 which is a continuation-in-part of U.S. patent application Ser. No. 09/363,316 filed Jul. 28, 1999, now U.S. Parent No. 6,392,019, which is a continuation-in-part of U.S. patent application Ser. No. 09/249,697 filed Feb. 12, 1999, now U.S. Parent No. 6,392,018, which is a continuation-in-part of U.S. patent application Ser. No. 08/968,800 filed Nov. 22, 1997, now abandoned. All of these applications are herein incorporated by reference in their entirety.

2. FIELD OF THE INVENTION

The present invention provides novel polynucleotides and proteins encoded by such polynucleotides, along with therapeutic, diagnostic and research utilities for these polynucleotides and proteins.

3. BACKGROUND

Technology aimed at the discovery of protein factors (including e.g., cytokines, such as lymphokines, interferons, colony stimulating factors and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

Meningiomas are brain tumors formed from cells of the meninges, which are membranes that cover the brain and spinal cord. Meningiomas are relatively common and account for roughly half of all primary tumors of the brain and spinal cord. They are generally benign and slow growing, but may cause serious neurological problems due to invasion of or pressure on surrounding brain tissue. Treatment options include surgical removal and radiation therapy.

Astrocytomas are brain tumors formed from astrocytes, a type of brain glial cell that provides physical and nutritional support to the neurons of the brain. Astrocytomas are also a common tumor of brain tissue origin and may vary in aggressiveness, from the very aggressive glioblastoma multiforme, to the moderately aggressive anaplastic astrocytoma, to the least aggressive astrocytoma. They spread by infiltrating surrounding brain tissue but usually do not metastasize to other parts of the body. Treatment options include surgical removal, radiation therapy and chemotherapy, but complete surgical removal is typically difficult if not impossible due to the extensive infiltration of normal tissue.

Breast cancer is one of the most common of all malignancies. In the United States, the cumulative lifetime probability of developing breast cancer is 12% and of dying from breast cancer is 3.5%. Staging and prognosis are usually based on invasion of lymph nodes; each additional positive lymph node is associated with a worse prognosis. In late stages of the disease, the breast cancer has metastasized to distant organs. More than 80% of breast cancers are of the invasive ductal type. The next most common variety, infiltrating lobular, constitutes almost 10% of all breast cancers. Medullary carcinoma represents about 5% of all breast cancers and is less likely to metastasize to regional lymph modes. The remaining 5% of breast cancers are generally less malignant. Treatment usually consists of surgical removal followed by radiation therapy and/or chemotherapy.

Cancer of the prostate is the most common malignancy in men in the U.S. and is the second most common cause of cancer death in men older than age 55 (after carcinomas of the lung and colon). Some carcinomas of the prostate are slow growing and may persist for long periods without significant symptoms, whereas others behave aggressively. Over 95% of prostatic cancers are adenocarcinomas that arise in the prostatic acini. The remaining prostatic cancers are divided among squamous cell and transitional cell carcinomas that arise in the ducts, carcinoma of the utricle, carcinosarcomas that arise in the mesenchymal elements of the gland, and occasional metastatic tumors. Treatment typically involves surgery, radiation therapy, and/or anti-androgen therapy.

Colon cancers are also a very common malignancy and typically are adenocarcinomas, or sometimes carcinoid tumors. Treatment is primarily surgical resection of the colon, although chemotherapy has been found to be beneficial in some cases.

Melanoma is a skin cancer which originates from melanocytes present in the epidermis and dermis. This cancer affects approximately 32,000 individuals per year in the United States. The incidence of melanoma has dramatically increased over the past 40 years. There are four types of melanoma. Three types, superficial spreading melanoma, lentigo maligna melanoma and acral lentigious melanoma have a period of superficial growth and the tumor does not penetrate deeply. These superficial tumors can be treated by surgical excision. The fourth type of melanoma, nodular melanoma, has a radial growth phase and is usually a deep invasive lesion which is capable of metastasis to any organ. These tumors can be treated with regional nodal dissection which may be complemented with chemotherapy, immunotherapy, chemoimmunotherapy and/or radiation therapy.

The types of sarcomas include osteosarcomas, fibrosarcomas, chondrosarcomas and Ewing's tumor. Osteosacromas originate from osteoprogenitor cells. These tumors have a wide range of histopathology with at least 12 subtypes and may metastasize generally to the lung. These tumors are treated with amputation, wide resection, chemotherapy or radiation.

Lymphomas are neoplastic transformations of cells residing within lymphoid tissues. Non-Hodgkin's lymphoma is derived primarily from B cells and is the most common neoplasm of patients between the ages of 20 and 40 years of age. There about 40,000 new cases of non-Hodgkin's lymphoma each year in the United States and incidence is increasing with the incidence of AIDS. There is only a 30–40% rate of curability of non-Hodgkin's Lymphoma. Conversely, it is unresolved which type of lymphoid cell from which Hodgkin's disease derives. Hodgkin's disease is a lymphoma which presents as a localized tumor that may spread to the contiguous lymphoid structures and eventually to other organs. Hodgkin's disease is most prevalent in males between the ages of 15–20 years and then after the age of 50 years. There is a greater than 75% rate of curability of Hodgkin's disease. Both non-Hodgkin's lymphoma and Hodgkin's disease are treated with radiotherapy, chemotherapy and salvage chemotherapy. In addition, non-Hodgkin's lymphoma may be treated with bone marrow transplants.

Treatment options for cancer are of unpredictable and sometimes limited value, and there continues to exist a need for novel therapies and diagnostic methods for cancer conditions.

4. SUMMARY OF THE INVENTION

The compositions of the present invention include novel isolated polypeptides, in particular, novel EGF-repeat-containing polypeptides, isolated polynucleotides encoding such polypeptides, including recombinant DNA molecules, cloned genes or degenerate variants thereof, especially naturally occurring variants such as allelic variants, and antibodies that specifically recognize one or more epitopes present on such polypeptides. The novel EGF-motif-containing polypeptide is denoted herein as EGFL6. In prior applications this same polypeptide has been referred to as ERHy1.

The compositions of the present invention additionally include vectors, including expression vectors, containing the polynucleotides of the invention, cells genetically engineered to contain such polynucleotides and cells genetically engineered to express such polynucleotides.

The isolated polynucleotides of the invention include, but are not limited to, a polynucleotide encoding a polypeptide comprising the amino acid sequence of SEQ ID NOS: 3, 6 or 24; a polynucleotide encoding a polypeptide comprising amino acid residues 1–502 of SEQ ID: 4 (The first amino acid residue in the sequence is designated as 1); a polynucleotide encoding a polypeptide comprising amino acid residues 1–21 of SEQ ID NOS: 6 or 24; a polynucleotide encoding a polypeptide comprising amino acid residues 80–93 of SEQ ID NO:6 or 24; a polynucleotide encoding a polypeptide comprising amino acid residues 95–128 of SEQ ID NO:6 or 24; a polynucleotide encoding a polypeptide comprising amino acid residues 133–168 of SEQ ID NO:6 or 24; a polynucleotide encoding a polypeptide comprising amino acid residues 175–214 of SEQ ID NO:6 or 24; a polynucleotide encoding a polypeptide comprising amino acid residues 220–259 of SEQ ID NO:6 or 24; a polynucleotide encoding a polypeptide comprising amino acid residues 446–465 of SEQ ID NO:6 or 24; or a polynucleotide encoding a polypeptide comprising amino acid residues 363–365 of SEQ ID NO:6 or 24.

The isolated polynucleotides of the invention further include, but are not limited to, a polynucleotide comprising the nucleotide sequence of SEQ ID NOS: 1, 2, 5 or 23; a polynucleotide comprising nucleotides 205–267 of the nucleotide sequence of SEQ ID NOS: 5 or 23 (The first nucleic acid residue of the sequence is designated as 1); a polynucleotide comprising nucleotides 442–483 of the nucleotide sequence of SEQ ID NOS: 5 or 23; a polynucleotide comprising nucleotides 487–588 of the nucleotide sequence of SEQ ID NOS: 5 or 23; a polynucleotide comprising nucleotides 601–708 of the nucleotide sequence of SEQ ID NOS: 5 or 23; a polynucleotide comprising nucleotides 727–846 of the nucleotide sequence of SEQ ID NOS: 5 or 23; a polynucleotide comprising nucleotides 862–981 of the nucleotide sequence of SEQ ID NOS: 5 or 23; a polynucleotide comprising nucleotides 1540–1599 of the nucleotide sequence of SEQ ID NOS: 5 or 23; a polynucleotide comprising nucleotides 1729–1731 of the nucleotide sequence of SEQ ID NOS: 5 or 23; or a polynucleotide comprising nucleotides 1291–1299 of the nucleotide sequence of SEQ ID NO:5 or 23.

The polynucleotides of the present invention still further include, but are not limited to, a polynucleotide comprising the nucleotide sequence of a cDNA insert of clone pEGFR-HY1 deposited with the American Type Culture Collection (ATCC; 10801 University Blvd., Manassas, Va., 20110-2209, U.S.A.); a polynucleotide comprising a nucleotide sequence of the cDNA insert of clone pEGFR-HY2 deposited with the ATCC; a polynucleotide comprising a nucleotide sequence of the cDNA insert of clone pEGFR-HY3 deposited with the ATCC; a polynucleotide comprising a nucleotide sequence encoding a polypeptide comprising the amino acid sequence encoded by the cDNA insert of clone pEGFR-HY1; a polynucleotide comprising a nucleotide sequence encoding a polypeptide comprising the amino acid sequence encoded by the cDNA insert of clone pEGFR-HY2; a polynucleotide comprising the nucleotide sequence encoding a polypeptide comprising the amino acid sequence encoded by the cDNA insert of clone pEGFR-HY3; a polynucleotide comprising the fill length protein coding sequence of SEQ ID NOS: 6 or 24 which polynucleotide comprises the cDNA insert of clone pEGFR-HY2, nucleic acids 323–357 of SEQ ID NOS: 5 or 23 and the cDNA insert of clone pEGFR-HY1; a polynucleotide comprising the nucleotide sequence of the mature protein coding sequence of SEQ ID NOS: 6 or 24 comprising the cDNA insert of clone pEGFR-HY2, nucleic acids 323–357 of SEQ ID NOS: 5 or 23 and the cDNA insert of clone pEGFR-HY1; a polynucleotide comprising the fill length protein coding sequence of SEQ ID NOS: 6 or 24 which polynucleotide is assembled from the cDNA insert of clone pEGFR-HY2, the cDNA insert of pEGFR-HY3 and the cDNA insert of clone pEGFR-HY1; or a polynucleotide comprising the nucleotide sequence of the mature protein coding sequence of SEQ ID NOS: 6 or 24 which polynucleotide is assembled from the cDNA insert of clone pEGFR-HY2, the cDNA insert of clone pEGFR-HY3 and the cDNA insert of clone pEGFR-HY1. The polynucleotides of the present invention also include, but are not limited to, a polynucleotide that hybridizes to the complement of the nucleotide sequence of SEQ ID NOS: 1, 2, 5 or 23 under stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO: 3, 6, or 24, or amino acids 1–502 of SEQ ID NO: 4. Contemplated allelic variants include those comprising the nucleotide sequences set forth in SEQ ID NO: 27, 29 or 31, the mature protein coding portions thereof, or fragments thereof encompassing the portions that differ in nucleotide sequence compared to SEQ ID NO: 23. Such fragments are particularly useful as probes to identify alleles and include fragments encompassing nucleotides 271 to 288 of SEQ ID NO: 27, nucleotides 271 to 279 of SEQ ID NO: 29, or nucleotides 1440–1442 of SEQ ID NO: 31.

The polynucleotides of the invention additionally include the complement of any of the polynucleotides recited above.

The isolated polypeptides of the invention include, but are not limited to, a polypeptide comprising the amino acid sequence of SEQ ID NOS: 3, 6 or 24; a polypeptide comprising amino acid residues 1–502 of SEQ ID NO: 4; a polypeptide comprising amino acid residues 1–21 of SEQ ID NOS: 6 or 24; a polypeptide comprising amino acid residues 80–93 of SEQ ID NOS: 6 or 24; a polypeptide comprising amino acid residues 95–128 of SEQ ID NOS: 6 or 24; a polypeptide comprising amino acid residues 133–168 of SEQ ID NOS: 6 or 24; a polypeptide comprising amino acid residues 175–214 of SEQ ID NO:6; a polypeptide comprising amino acid residues 220–259 of SEQ ID NOS: 6 or 24; a polypeptide comprising amino acid residues 446–465 of SEQ ID NOS: 6 or 24; or a polypeptide comprising amino acid residues 363–365 of SEQ ID NOS: 6 or 24. The polypeptide of SEQ ID NOS: 6 or 24 has been designated EGFL6.

The polypeptides of the present invention further include, but are not limited to, a polypeptide comprising the amino acid sequence encoded by the cDNA insert of clone pEGFR-HY1 deposited with the ATCC; a polypeptide comprising the amino acid encoded by the cDNA insert of clone pEGFR-HY2 deposited with the ATCC; a polypeptide comprising the amino acid encoded by the cDNA insert of clone pEGFR-HY3 deposited with the ATCC; a full length protein of SEQ ID NO:6 or 24 comprising the amino acid sequence encoded by the cDNA insert of clone pEGFR-HY2, nucleic acids 323–357 of SEQ ID NOS: 5 or 23 and the cDNA insert of clone pEGFR-HY1, or; a mature protein coding sequence of SEQ ID NOS: 6 or 24 comprising the amino acid sequence encoded by the cDNA insert of clone pEGFR-HY2, nucleic acids 323–357 of SEQ ID NOS: 5 or 23 and the cDNA insert of clone pEGFR-HY1. The polypeptides of the present invention also include, but are not limited to, a full length protein of SEQ ID NO:6 or 24 encoded by the open reading frame (ORF) assembled from the cDNA insert of clone pEGFR-HY2, the cDNA insert of clone pEGFR-HY3 and the cDNA insert of clone pEGFR-HY1; or a mature protein coding sequence of SEQ ID NOS: 6 or 24 encoded by the ORF assembled from the cDNA insert of clone pEGFR-HY2, the cDNA insert of clone pEGFR-HY3 and the cDNA insert of clone pEGFR-HY1. Polypeptides of the invention include isoforms encoded by the allelic variants of SEQ ID NOS: 27, 29 or 31, mature protein portions thereof, or fragments of at least about 5 amino acids encompassing the portions that differ in amino acid sequence compared to SEQ ID NO: 24. Polypeptides comprising such fragments may be useful in generating antibodies specific for the isoforms, and include fragments encompassing amino acid 28 to 33 of SEQ ID NO: 28, amino acid 28 to 30 of SEQ ID NO: 30, or amino acid 395 of SEQ ID NO: 32.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide.

Methods are also provided for preventing, treating or ameliorating a medical condition which comprises administering to a mammalian subject a therapeutically effective amount of a composition comprising a protein of the present invention and a pharmaceutically acceptable carrier.

In particular, the polypeptides and polynucleotides of the invention can be utilized, for example, as part of methods for stimulation of epithelial tissue growth, e.g., skin regeneration. The polypeptides and polynucleotides of the invention may, therefore, be utilized, for example, as part of methods for tissue repair and regeneration, corneal transplant healing, burn treatment, skin graft production and administration, and wound healing, e.g., treatment of surgical incisions, and ulcers, such as stomach or diabetic ulcers. In addition, the polynucleotides and polypeptides of the invention can further be utilized, for example, as part of methods for the prevention and/or treatment of disorders involving cell fate and differentiation, such as leukemias, brain tumors (including meningiomas, glioblastoma multiforme, anaplastic astrocytomas, cerebellar astrocytomas, other high-grade or low-grade astrocytomas, brain stem gliomas, oligodendrogliomas, mixed gliomas, other gliomas, cerebral neuroblastomas, craniopharyngiomas, diencephalic gliomas, germinomas, medulloblastomas, ependymomas, choroid plexus tumors, pineal parenchymal tumors, gangliogliomas, neuroepithelial tumors, neuronal or mixed neuronal glial tumors), lung tumors (including small cell carcinomas, epidermoid carcinomas, adenocarcinomas, large cell carcinomas, carcinoid tumors, bronchial gland tumors, mesotheliomas, sarcomas or mixed tumors), prostate cancers (including adenocarcinomas, squamous cell carcinoma, transitional cell carcinoma, carcinoma of the prostatic utricle, or carcinosarcomas), breast cancers (including adenocarcinomas or carcinoid tumors), or gastric, intestinal, or colon cancers (including adenocarcinomas, invasive ductal carcinoma, infiltrating or invasive lobular carcinoma, medullary carcinoma, ductal carcinoma in situ, lobular carcinoma in situ, colloid carcinoma or Paget's disease of the nipple), skin cancer (including melanoma, squamous cell carcinoma, tumor progression of human skin keratinocytes, basal cell carcinoma, hemangiopericytoma and Karposi's sarcoma), lymphoma (including Hogkin's disease and non-Hodgkin's lymphoma), sarcomas (including osteosarcoma, chondrosarcoma and fibrosarcoma) as well as for the treatment of nervous system disorders.

The methods of the present invention further relate to methods for detecting the presence of the polynucleotides or polypeptides of the invention in a sample. Such methods can, for example, be utilized as part of prognostic and diagnostic evaluation of disorders as recited above and for the identification of subjects exhibiting a predisposition to such conditions. Furthermore, the invention provides methods for evaluating the efficacy of drugs, and monitoring the progress of patients, involved in clinical trials for the treatment of disorders as recited above.

The EGFL6 genes of the present invention is expressed in certain cancer cells, particularly meningiomas, lung tumors, and has been localized to chromosome X, aberrations in which have been implicated in meningiomas and lung tumors. EGFL6 mRNA has also been shown to be differentially expressed in tonsil, placenta, breast carcinomas, prostate carcinomas, lung carcinomas, brain tumors, skin tumors, sarcomas, lymphomas and colon carcinomas while having only low expression in normal breast and normal lung and no detectable expression in normal prostate, brain, skin, skeletal and smooth muscle, lymph nodes or colon. EGF motif-containing molecules have been previously linked to the progression of various cancers. In addition, EGFL6 mRNA expression was detected at all grades and stages of cancer tested indicating EGFL6 expression is detectable at low grades. Highly specific and significant expression of EGFL6 in tumor cells indicates that this protein represents a potential marker of malignancy and a potential candidate for small molecule therapeutic development for the treatment of certain tumors. Expression of EGFL6 has been shown to promote cellular proliferation. Thus, compounds that inhibit the activity of EGFL6 polypeptides, including variants thereof (having preferably at least about 80%, 81%, 82%, 83%, 84%, 85%, 86%, 87%, 88%, 89%, 90%, 91%, 92%, 93% 94, 95%, 96%, 97%, 98% or 99% sequence identity to SEQ ID NO: 24), are expected to reduce undesirable cellular proliferation, particularly cancer cell generation, proliferation or metastasis. Such compounds include antibodies or fragments thereof, antisense polynucleotides, or small molecule modulators of EGFL6 receptor-binding or other activity.

Moreover, the addition of EGFL6 to cell culture or the expression of EGFL6 by cells in culture may enhance proliferation of the cells being cultured, particularly where cells are undifferentiated (e.g. precursor or progenitor cells) or dedifferentiated cells.

Thus, the prognostic and diagnostic methods contemplated according to this aspect of the invention include methods of detecting or quantitating EGFL6 polypeptides in tissue s (e.g., biopsied tissue from brain, lung, breast, prostate, colon, intestine, stomach, or other tissues) or body fluid s (e.g., cerebrospinal fluid, pleural fluid, sputum, ascites, blood, urine, feces, prostatic fluid or other fluids), particularly for diagnosis, prognosis or monitoring of cancer. For these methods of detecting the level of EGFL6 polynucleotide or polypeptide in tissues and bodily fluid, the level of EGFL6 detected is correlated with a standard indicative of the diagnosis of cancer.

The invention provides for methods of detecting cancerous cell expressing the EGFL6 polynucleotide, including but not limited to prostate cancer cells, breast cancer cells, colon cance cells, brain cancer such as meningoma and astrocytoma, skin cancer cells such as melanoma, lymphoma cells and sarcoma cells, comprising the step of contacting the a biological sample with a labeled polynucleotide complementary to an EGFL6 polynucleotide or a fragment thereof for a period sufficient to form a complex; and detecting the complex so that if a complex is detected, the cancerous cell is detected. These methods include detecting the EGFL6 polynucleotide comprising SEQ ID NO: 23, a polynucleotide fragment of SEQ ID NO: 23, a nucleotide sequence encoding the mature protein coding portion of SEQ ID NO: 24 or a nucleotide sequence having at least 90% identity to SEQ ID NO: 23. These methods also include detecting a cancerous cell comprising expressing the EGFL6 polypeptide in a biological sample comprising contacting the sample with an antibody or fragment thereof that specifically binds to the EGFL6 polypeptide or a fragment thereof for a period sufficient to form a complex and detecting the complex, so that if a complex is detected, the cancerous cell is detected. The EGFL6 polypeptides include a polypeptide comprising the amino acid sequence of SEQ ID NO: 24, a polypeptide fragment of SEQ ID NO: 24, such as a polypeptide fragment comprises amino acids 412 to 424 of SEQ ID NO: 24, polypeptide fragment comprising the mature protein sequence of SEQ ID NO: 24 or a polypeptide with 90% sequence identify to SEQ ID NO: 24. Biological samples include tissue samples and cell samples including those extracted by biopsy or surgery, and biological fluids including but not limited to serum, blood, urine, lymphatic fluid and cerebrospinal fluid. The polypeptide complementary to SEQ ID NO: 24 may be labeled with a radio isotope, affinity label, enzymatic label or a fluorescent label.

The invention also provides methods for the identification of compounds that modulate the expression of the polynucleotides and/or polypeptides of the invention. Such methods can be utilized, for example, for the identification of compounds that can ameliorate symptoms of disorders as recited above. Such methods can include, but are not limited to, assays for identifying compounds and other substances that interact with (e.g., bind to) the polypeptides of the invention. For example, assays may include the step of measuring EGFL6-induced cell proliferation in the presence of and absence of a test compound. Candidate inhibitors identified by these methods are also contemplated.

The methods of the invention also include methods for the treatment of disorders as recited above which may involve the administration of such compounds to individuals exhibiting symptoms or tendencies related to disorders as recited above. In addition, the invention encompasses methods for treating diseases or disorders as recited above by administering compounds and other substances that modulate the overall activity of the target gene products. Compounds and other substances can effect such modulation either on the level of target gene expression or target protein activity.

The linkage of EGFL6 with cancer indicates that inhibitors of its activity (that either inhibit expression of the gene product or inhibit activity of the gene product itself) may be useful in treating cancer conditions. Such inhibitors include antisense polynucleotides, antibodies, and other modulators identified through, e g., screening of libraries or combinatorial libraries of inorganic or organic compounds (such as bacterial, fungal, mammalian, insect or plant products, peptides, peptidomimetics and organomimetics). Such modulators may be administered parenterally, including into the cerebro-spinal fluid, or locally via an implant or device.

The present invention demonstrates that expression of an EGFL6 polypeptide increases tumor cell tumorgenicity in vitro as indicated by colony formation in soft agar (See Example 13). Tumorgenic cells have a transformed phenotype and possess the properties necessary to form tumors. Tumorgenic cells include malignant cells. In tumor progression, the transformed cells proceed through a multistep process from a transformed phenotype to a neoplastic phenotype and eventually to a metastatic phenotype. The growth characteristics of transformed cells in vitro include immortality, anchorage independence, loss of contact inhibition, reduced density dependence, low serum requirement, growth factor independence, high plating efficiency and shorter population doubling time. The genetic properties of transformed and tumorgenic cells include a high spontaneous mutation rate, anuploidy and heteroploidy. The properties of a neoplastic cell include tumorgenicity, angiogenicity, invasiveness and enhanced protease secretion. Tumorgenicity can be assessed by assays well known in the art which measure any of the properties listed above.

The methods of the invention include methods of reducing tumor size in a patient suffering from cancer, including but not limited to prostate cancer, breast cancer, colon cancer, brain cancer such as meningoma and astrocytoma, and skin cancer such as melanoma, lymphoma and sarcoma, comprising administering to the patient an inhibitor of EGFL6 activity wherein the inhibitor binds the EGFL6 polypeptide, such as the polypeptide comprising the amino acid sequence of SEQ ID NO: 24, the mature protein sequnence of SEQ ID NO: 24 or a EGFL6 receptor polypeptide. Inhibitors of EGFL6 activity include antibodies and fragments thereof, peptides, and small molecules. The inhibitor may also be an antisense polynucleotide which binds to the polynucleotide, or a fragment or variant thereof, which encodes the mature protein coding portion of SEQ ID NO: 24.

The present invention also provides for methods of inhibiting tumorgenicity in a cell expressing an EGFL6 polypeptide comprising the step of contacting said cells with an antibody or fragment thereof that specifically binds the polypeptide of SEQ ID NO: 24 or a fragment thereof, or contacting said cell with an antisense polynucleotide that specifically binds a polynucleotide, or a fragment or variant thereof encoding the mature protein coding portion of the polypeptide of SEQ ID NO: 24. These methods include contacting cells which are present in a subject suffering from cancer, including but not limited to prostate cancer, breast cancer, colon cancer, brain cancer such as meningoma and astrocytoma, and skin cancer such as melanoma, lymphoma and sarcoma.

The invention provides for methods of inhibiting proliferation of cancer cells, comprising the step of contacting the cells with an antibody or fragment thereof that specifically binds the polypeptide of SEQ ID NO: 24 or a fragment thereof, or contacting said cell with an antisense polynucleotide that specifically binds a polynucleotide, or a fragment or variant thereof which encodes the mature protein coding portion of the polypeptide of SEQ ID NO: 24. These methods include contacting cells which are present in a subject suffering from cancer, including but not limited to prostate cancer, breast cancer, colon cancer, brain cancer such as meningoma and astrocytoma, and skin cancer such as melanoma, lymphoma and sarcoma.

The invention provides for pharmaceutical compositions comprising an amount of an antibody or fragment thereof that specifically binds to a polypeptide of SEQ ID NO: 24 in a pharmaceutically acceptable carrier, wherein the amount of antibody or fragment thereof effectively inhibits EGFL6 polypeptide activity, such as those activities described herein, reduces tumor size, inhibits cancer cell proliferation or inhibits tumorgenicity. The invention also provides for pharmaceutical compositions comprising an amount of an antisense polynucleotide that specifically binds to a polynucleotide encoding the mature protein coding portion of SEQ ID NO: 24 in a pharmaceutically acceptable carrier, wherein the amount of antisense polynucleotide effectively inhibits EGFL6 polypeptide activity, such as those activities described herein, reduces tumor size, inhibits cancer cell proliferation or inhibits tumorgenicity.

5. BRIEF DESCRIPTION OF THE DRAWINGS

FIG. 1 shows the sequence alignment of an EGF repeat containing portion of SEQ ID Nos. 3–4 (displayed sequence is SEQ ID NO: 9) with the consensus EGF-repeat motifs of drosophila Notch (SEQ ID NO: 7), CD97 (SEQ ID NO: 10), and the consensus EGF-R repeat (SEQ ID NO: 11). A—Alanine; R—Arginine; N—Asparagine; D—Aspartic Acid; C—Cysteine; E—Glutamic Acid; Q—Glutamine; G—Glycine; H—Histidine; I—Isoleucine; L—Leucine; K—Lysine; M—Methionine; F—Phenylalanine; P—Proline; S—Serine; T—Threonine; W—Tryptophan; Y—Tyrosine; V—Valine; X—any of the twenty amino acids. Gaps are presented as spaces and nonconserved residues as dashes. Regions of SEQ ID No. 4 are labeled 10244 (SEQ ID NO: 8). Amino acid positions for location of the beginning of each protein stretch are provided. Notch, CD97, and EGF-R are labeled accordingly. Consensus sequences are labeled (C). The conserved cysteines and glycines are underlined.

FIG. 2 shows the nucleic acid sequences that were obtained from the $b^2$HFLS20W cDNA library using standard PCR, sequencing by hybridization signature analysis, and single pass gel sequencing technology. These sequences are designated as SEQ ID Nos. 1–2. A—adenosine; C—cytosine; G—guanosine; T—thymidine; and N—any of the four bases.

FIG. 3 shows SEQ ID NOS:3–4. The amino acid sequence of SEQ ID NO: 3 corresponds to the polynucleotide sequence of SEQ ID NO: 1. (The amino acid sequence of SEQ ID NO: 18 corresponds to the polynucleotide sequence of SEQ ID NO: 2.) Amino acid residues 1–502 of SEQ ID NO:4 correspond to the polynucleotide sequence of SEQ ID NO:2 and to amino acid positions 52–553 of of SEQ ID NO 6 or 24 (see FIG. 5). A—Alanine; R—Arginine; N—Asparagine; D—Aspartic Acid; C—Cysteine; E—Glutamic Acid; Q—Glutamine; G—Glycine; H—Histidine; I—Isoleucine; L—Leucine; K—Lysine; M—Methionine; F—Phenylalanine; P—Proline; S—Serine; T—Threonine; W—Tryptophan; Y—Tyrosine; V—Valine; X—any of the twenty amino acids.

FIG. 4 shows SEQ ID NO: 5 or 23, and the amino acid translation (SEQ ID NOS: 6 or 24). SEQ ID NO: 5 is a 5-prime and 3-prime extension of the cDNA sequence, SEQ ID NO: 2. Resequencing of pEGFR-HY2 and pEGFR-HY3 indicated an error in SEQ ID NO: 5 as presented in FIG. 4 and clarified an ambiguous nucleotide within the coding region. Nucleotide 244 was reported to be a cytosine (C) in SEQ ID NO: 5 and should be a thymidine (T). Nucleotide 1273 was reported to be a tryptophan (W) in SEQ ID NO: 5 and should be an adenine (A). The correct sequence is presented in SEQ ID NO: 23.

SEQ ID NO: 6 or 24 is the amino acid translation from nucleotide 205 to 1866 of SEQ ID NO: 5 or 23, including the starting methionine and stop codon. The first 21 amino-acids comprise the hydrophobic region that represents the signal peptide. The sequencing error described above caused an error in the translated amino acid sequence shown in SEQ ID NO: 6 where a proline (P) residue was reported at amino acid 14. The corrected nucleotide sequence (SEQ ID NO: 23) resulted in a serine (S) at position 14 and an isoleucine at position 357, and this corrected amino acid sequence is presented as SEQ ID NO: 24.

FIG. 5 shows three-dimensional ribbon diagrams comparing the peptidyl backbone of amino acids 221–260 of EGFL6 with that of the 53 amino acid EGF protein. Although amino acids 221–260 of EGFL6 show only 22% identity with the amino acid sequence of EGF, 5 out of the 6 cysteines in EGF are conserved and the three-dimensional structures look similar to each other.

6. DETAILED DESCRIPTION

6.1. Definitions

The term “nucleotide sequence” refers to a heteropolymer of nucleotides or the sequence of these nucleotides. The terms “nucleic acid” and “polynucleotide” are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms “oligonucleotide fragment” or a “polynucleotide fragment”, “portion.” or “segment” is a stretch of polypeptide nucleotide residues which is long enough to use in polymerase chain reaction (PCR) or various hybridization procedures to identify or amplify identical or related parts of mRNA or DNA molecules.

The terms “oligonucleotides” or “nucleic acid probes” are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250).

The term “probes” includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al, 1989, Current Protocols in Molecular Biology, John Wiley & Sons, New York N.Y., both of which are incorporated herein by reference in their entirety.

The term “stringent” is used to refer to conditions that are commonly understood in the art as stringent. Stringent conditions can include highly stringent conditions (i.e., hybridization to filter-bound DNA under in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i e., washing in 0.2×SSC/0.1% SDS at 42° C.).

In instances wherein hybridization of deoxyoligonucleotides is concerned, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term “recombinant,” when used herein to refer to a polypeptide or protein, means that a polypeptide or protein is derived from recombinant (e.g., microbial or mammalian) expression systems. “Microbial” refers to recombinant polypeptides or proteins made in bacterial or fungal (e.g., yeast) expression systems. As a product, “recombinant microbial” defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

The term “recombinant expression vehicle or vector” refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term “recombinant expression system” means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term “open reading frame,” ORF, means a series of nucleotide triplets coding for amino acids without any termination codons and is a sequence translatable into protein.

The term “expression modulating fragment,” EMF, means a series of nucleotides which modulates the expression of an operably linked ORF or another EMF.

As used herein, a sequence is said to “modulate the expression of an operably linked sequence” when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an “uptake modulating fragment,” UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term "active" refers to those forms of the polypeptide which retain the biologic and/or immunologic activities of any naturally occurring polypeptide.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20% (i.e., the number of individual residue substitutions, additions, and/or deletions in a substantially equivalent sequence, as compared to the corresponding reference sequence, divided by the total number of residues in the substantially equivalent sequence is about 0.2 or less). Such a sequence is said to have 80% sequence identity to the listed sequence. In one embodiment, a substantially equivalent, e.g., mutant, sequence of the invention varies from a listed sequence by no more than 10% (90% sequence identity); in a variation of this embodiment, by no more than 5% (95% sequence identity); and in a further variation of this embodiment, by no more than 2% (98% sequence identity). Substantially equivalent, e.g., mutant, amino acid sequences according to the invention generally have at least 95% sequence identity with a listed amino acid sequence, whereas substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded.

Nucleic acid sequences encoding such substantially equivalent sequences, e.g., sequences of the recited percent identities, can routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e g, polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

The term "secreted" protein includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Each of the above terms is meant to encompasses all that is described for each, unless the context dictates otherwise.

6.2 Nucleic Acids and Polypeptides of the Invention

Nucleotide and amino acid sequences of the invention are reported below. Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al, J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fe portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides both full-length and mature forms (for example, without a hydophobic signal peptide) of the disclosed proteins. The full-length form of the such proteins is identified in the sequence listing by translation of the nucleotide sequence of each disclosed clone. The mature form of such protein may be obtained by expression of the disclosed full-length polynucleotide (for example, obtained from using the clones deposited with ATCC using standard techniques) in a suitable mammalian cell or other host cell. The sequence of the mature form of the protein is also determinable from the amino acid sequence of the full-length form.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Species homologs of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides.

Species homologs of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

6.2.1. Nucleic Acids of the Invention

The isolated polynucleotides of the invention include, but are not limited to polynucleotides encoding a polypeptide comprising the amino acid sequence of SEQ ID NOS:3, 6 or 24 or amino acid residues 1–502 of SEQ ID NO: 4 as well as polynucleotides which encode specific domains thereof. For example, a polynucleotide encoding a polypeptide comprising amino acid residues 1–21 of SEQ ID NOS: 6 or 24; a polynucleotide encoding a polypeptide comprising amino acid residues 80–93 of SEQ ID NO:6 or 24; a polynucleotide encoding a polypeptide comprising amino acid residues 95–128 of SEQ ID NO:6 or 24; a polynucleotide encoding a polypeptide comprising amino acid residues 133–168 of SEQ ID NO:6 or 24; a polynucleotide encoding a polypeptide comprising amino acid residues 175–214 of SEQ ID NO:6 or 24; a polynucleotide encoding a polypeptide comprising amino acid residues 220–259 of SEQ ID NO:6 or 24; a polynucleotide encoding a polypeptide comprising amino acid residues 446–465 of SEQ ID NO:6 or 24; or a polynucleotide encoding a polypeptide comprising amino acid residues 363–365 of SEQ ID NO:6 or 24.

In particular embodiments, the isolated polynucleotides of the invention include, but are not limited to, a polynucleotide comprising the nucleotide sequence of SEQ ID NOS:1, 2, 5 or 23; a polynucleotide comprising nucleotides 205–267 of the nucleotide sequence of SEQ ID NO:5 or 23; a polynucleotide comprising nucleotides 442–483 of the nucleotide sequence of SEQ ID NO:5 or 23; a polynucleotide comprising nucleotides 487–588 of the nucleotide sequence of SEQ ID NO:5 or 23; a polynucleotide comprising nucleotides 601–708 of the nucleotide sequence of SEQ ID NO:5 or 23; a polynucleotide comprising nucleotides 727–846 of the nucleotide sequence of SEQ ID NO:5 or 23; a polynucleotide comprising nucleotides 862–981 of the nucleotide sequence of SEQ ID NO:5 or 23; a polynucleotide comprising nucleotides 1540–1599 of the nucleotide sequence of SEQ ID NO:5 or 23; a polynucleotide comprising nucleotides 1729–1731 of the nucleotide sequence of SEQ ID NO:5 or 23; or a polynucleotide comprising nucleotides 1291–1299 of the nucleotide sequence of SEQ ID NO:5 or 23.

The polynucleotides of the present invention still further include, but are not limited to, a polynucleotide comprising the nucleotide sequence of the cDNA insert of clone pEGFR-HY1 deposited with the ATCC; a polynucleotide comprising the nucleotide sequence of the cDNA insert of clone pEGFR-HY2 deposited with the ATCC; a polynucleotide comprising the nucleotide sequence of the cDNA insert of clone pEGFR-HY3 deposited with the ATCC; a polynucleotide comprising the nucleotide sequence encoding a polypeptide comprising the amino acid sequence encoded by the cDNA insert of clone pEGFR-HY1; a polynucleotide comprising the nucleotide sequence encoding a polypeptide comprising the amino acid sequence encoded by the cDNA insert of clone pEGFR-HY2; a polynucleotide comprising the nucleotide sequence encoding a polypeptide comprising the amino acid sequence encoded by the cDNA insert of clone pEGFR-HY3; a polynucleotide comprising the full length protein coding sequence of SEQ ID NOS: 6 or 24 which polynucleotide comprises the cDNA insert of clone pEGFR-HY2, nucleic acids 323–357 of SEQ ID NOS. 5 or 23 and the cDNA insert of clone pEGFR-HY1; a polynucleotide comprising the nucleotide sequence of the mature protein coding sequence of SEQ ID NOS: 6 or 24 which polynucleotide comprises the cDNA insert of clone pEGFR-HY2, nucleic acids 323–357 of SEQ ID NOS: 5 or 23 and the cDNA insert of clone pEGFR-HY1; a polynucleotide comprising the full length protein coding sequence of SEQ ID NOS: 6 or 24 which polynucleotide is assembled from the the cDNA insert of clone pEGFR-HY2, the cDNA insert of clone pEGFR-HY3 and the cDNA insert of clone pEGFR-HY1, or; a polynucleotide comprising the nucleotide sequence of the mature protein coding sequence of SEQ ID NOS: 6 or 24 which polynucleotide is assembled from the cDNA insert of clone pEGFR-HY2, the cDNA insert of clone pEGFR-HY3 and the cDNA insert of clone pEGFR-HY1.

Following the methods of Example 1, below, a splice variant (SEQ ID NO: 27) and a SNP (SEQ ID NO: 29) of EGFL6 were identified. The predicted amino acid sequence of SEQ ID NOs: 27 and 29 are set forth in SEQ ID NOs: 28 and 30, respectively. Sequence analysis determined that SEQ ID NO: 27 has a 6 amino acid insertion at about amino acid 30 of SEQ ID NO: 23; and is 98% identical to the amino acid sequence of EGFL6. Sequence analysis also revealed that SEQ ID NO: 29 has a His residue inserted at about amino acid 29 of SEQ ID NO: 23, and is 99% identical to the amino acid sequence of EGFL6. An additional SNP, which was previously identified as SEQ ID NO: 189 in U.S. patent application Ser. No. 09/620,312 filed Jul. 19, 2000, is set forth in SEQ ID NO: 31. The amino acid encoded by SEQ ID NO: 31 is set forth in SEQ ID NO: 32. Sequence analysis of this SNP shows that it contains an Ala residue inserted at about amino acid 395 of SEQ ID NO: 23.

The polynucleotides of the present invention also include, but are not limited to, a polynucleotide that hybridizes to the complement of the nucleotide sequence of SEQ ID NOS: 1, 2, 5 or 23 under stringent hybridization conditions; a polynucleotide which is an allelic variant of any polynucleotide recited above; a polynucleotide which encodes a species homologue of any of the proteins recited above; or a polynucleotide that encodes a polypeptide comprising an additional specific domain or truncation of the polypeptide of SEQ ID NOS: 3, 6 or 24, or amino acid residues 1–502 of SEQ ID NO:4.

The polynucleotides of the invention additionally include the complement of any of the polynucleotides recited above.

The polynucleotides of the invention also provide polynucleotides including nucleotide sequences that are substantially equivalent to the polynucleotides recited above. Polynucleotides according to the invention can have at least about 80%. 81%, 82%, 83%, 84%, 85%, 86%, 87%, 88%, or 89%, more typically at least about 90% 91%, 92%, 93%, or 94%, and even more typically at least about 95%, 96%, 97%, 98% or 99%, sequence identity to a polynucleotide recited above. The invention also provides the complement of the polynucleotides including a nucleotide sequence that has at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99% sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the sequence provided in SEQ ID NOS:1, 2, 5 or 23, a representative fragment thereof, or a nucleotide sequence at least 99.9% identical to SEQ ID NOS: 1, 2, 5 or 23, with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NOS:1, 2 5 or 23 or a fragment thereof. The recombinant constructs of the present invention comprise a vector, such as a plasmid or viral vector, into which a nucleic acid having the sequence of SEQ ID NOS:1, 2, 5 or 23, or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the penplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that specifically hybridize under stringent conditions to a fragment of the DNA sequence in FIG. 2 or 4 (SEQ ID NOS: 1, 2 or 5), or SEQ ID NOS: 23, 27, 29, or 31 or their complements, which fragment is greater than about 10 bp, preferably 20–50 bp, or 30–75 bp and even greater than 100 bp. Such fragments are preferably less than about 300 bp, or more preferably less than about 250 bp, or less than about 200 bp, or less than about 150 bp in length. In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al, Gene 34:315 (1985); and other mutagenesis techniques well known in the art, such as, for example, the techniques in Sambrook et al, supra, and Current Protocols in Molecular Biology, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

6.2.2. Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al, *Basic Methods in Molecular Biology* (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in *Molecular Cloning: A Laboratory Manual*, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g, inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al, each of which is incorporated by reference herein in its entirety.

6.2.3. Polypeptides of the Invention

The isolated polypeptides of the invention include, but are not limited to, a polypeptide comprising the amino acid sequence of SEQ ID NOS: 3, 6 or 24 or amino acid residues 1–502 of SEQ ID NO: 4. The polypeptides of the invention further include polypeptides which comprise one or more specific domains of the amino acid sequence in SEQ ID NOS:3, 6 or 24 or amino acid residues 1–502 of SEQ ID NO: 4. For example, but not limited to, a polypeptide comprising amino acid residues 1–21 of SEQ ID NOS: 6 or 24; a polypeptide comprising amino acid residues 80–93 of SEQ ID NO:6 or 24; a polypeptide comprising amino acid residues 95–128 of SEQ ID NO:6 or 24; a polypeptide comprising amino acid residues 133–168 of SEQ ID NO:6 or 24; a polypeptide comprising amino acid residues 175–214 of SEQ ID NO:6 or 24; a polypeptide comprising amino acid residues 220–259 of SEQ ID NOS: 6 or 24; a polypeptide comprising amino acid residues 446–465 of SEQ ID NO:6 or 24 or; a polypeptide comprising amino acid residues 363–365 of SEQ ID NO:6 or 24.

The polypeptides of the present invention further include, but are not limited to, a polypeptide comprising the amino acid sequence encoded by the cDNA insert of clone pEGFR-HY1 deposited with the ATCC; a polypeptide comprising the amino acid encoded by the cDNA insert of clone pEGFR-HY2 deposited with the ATCC; a polypeptide comprising the amino acid encoded by the cDNA insert of clone pEGFR-HY3 deposited with the ATCC; a full length protein coding sequence of SEQ ID NOS: 6 or 24 comprising the cDNA insert of clone pEGFR-HY2, nucleic acids 323–357 of SEQ ID NOS: 5 or 23 and the cDNA insert of clone pEGFR-HY1 or; a mature protein coding sequence of SEQ ID NOS: 6 or 24 comprising the cDNA insert of clone pEGFR-HY2, nucleic acids 323–357 of SEQ ID NOS: 6 or 24 and the cDNA insert of clone pEGFR-HY1. The polypeptides of the present invention also include, but are not limited to, a full length protein of SEQ ID NO:6 or 24 encoded by the open reading frame (ORF) assembled from the cDNA insert of clone pEGFR-HY2, the cDNA insert of clone pEGFR-HY3 and the cDNA insert of clone pEGFR-HY1; or a mature protein coding sequence of SEQ ID NOS: 6 or 24 encoded by the ORF assembled from the cDNA insert of clone pEGFR-HY2, the cDNA insert of clone pEGFR-HY3 and the cDNA insert of clone pEGFR-HY1.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture For example, the methods of the invention include a process for producing a polypeptide in which a host cell containing a suitable expression vector that includes a polynucleotide of the invention is cultured under conditions that allow expression of the encoded polypeptide.

The polypeptide can be recovered from the culture, conveniently from the culture medium, and further purified. Preferred embodiments include those in which the protein produced by such process is a full length or mature form of the protein.

The invention further provides a polypeptide including an amino acid sequence that is substantially equivalent to SEQ ID NOS:3, 6 or 24 or amino acid residues 1–502 of SEQ ID NO:4. Polypeptides according to the invention can have at least about 95%, and more typically at least about 98%, sequence identity to SEQ ID NO:3, 6 or 24 or amino acid residues 1–502 of SEQ ID NO: 4.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., *Scopes, Protein Purification: Principles and Practice*, Springer-Verlag (1994); Sambrook, et al., in *Molecular Cloning: A Laboratory Manual*; Ausubel et al., *Current Protocols in Molecular Biology*.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to a tumor or other cell by the specificity of the binding molecule for SEQ ID NOS: 3, 6 or 24 or amino acid residues 1–502 of SEQ ID NO: 4.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat.RTM. kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl.RTM. or Cibacrom blue 3GA Sepharose.RTM.; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and In Vitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

6.2.3. Deposit of Clones

The clones, pEGFR-HY1 and pEGFR-HY2 were deposited with the American Type Culture Collection (ATCC) 10801 University Avenue, Manassas, Va., on Nov. 20, 1998 under the terms of the Budapest Treaty. The clone pEGFR-HY3 was deposited with the American Type Culture Collection (ATCC) 10801 University Avenue, Manassas, Va., on Nov. 25, 1998 under the terms of the Budapest Treaty. The cDNA insert of clone pEGFR-HY1 corresponds to nucleic acids 358–2365 of SEQ ID NOS: 5 or 23. The vector containing the cDNA insert is pT7T3D-pac; the cDNA insert is flanked by EcoR1 and Pac1 restriction sites. The cDNA insert of pEGFR-HY2 corresponds to nucleic acids 1–322 of SEQ ID NOS: 5 or 23. The vector containing the cDNA insert is pGEM®-T Easy Vector (Promega) with Marathon® cDNA Adaptor 2 Primer (Clontech) sequence attached to the 5' end. The cDNA insert is flanked by EcoRI sites. The clone pEGFR-HY3 was deposited the American Type Culture Collection (ATCC) 10801 University Avenue, Manassas, Va., on Nov. 25, 1998 under the terms of the Budapest Treaty. The cDNA insert of clone pEGFR-HY3 corresponds to nucleic acids 223 to 1193 of SEQ ID NOS: 5 or 23. The vector containing the cDNA insert is pGEM®-T Easy Vector (Promega) with Marathon® cDNA Adaptor 2 Primer (Clontech) sequence attached to the 5' end. The cDNA insert is flanked by EcoRI sites. The clones represent plasmid clones as described in the Examples set forth below.

| Microorganism/Clone | ATCC Accession No. |
|---|---|
| pEGFR-HY1 | 203492 |
| pEGFR-HY2 | 203493 |
| pEGFR-HY3 | 203498 |

6.3. Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

6.3.1. Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A R. Kimmel eds., 1987.

6.3.2. Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

6.3.3. Cytokine and Cell Proliferation/ Differentiation Activity

A protein of the present invention may exhibit cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK. The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152–1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin .gamma., Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al, J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S.C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al, J. Immunol. 140:508–512, 1988.

6.3.4. Immune Stimulating or Suppressing Activity

A protein of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by vital (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally maybe desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-vital immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I .alpha. chain protein and .beta.sub.2 microglobulin protein or an MHC class II .alpha. chain protein and an MHC class II .beta. chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al, J. Immunol. 128:1968–1974, 1982; Handa et al, J. Immunol. 135:1564–1572, 1985; Takai et al, I. Immunol. 137:3494–3500, 1986; Takai et al, J. Immunol. 140:508–512, 1988; Herrmann et al, Proc. Natl. Acad. Sci. USA 78:2488–2492, 1981; Herrmann et al., J. Immunol. 128:1968–1974, 1982; Handa et al, J. Immunol. 135:1564–1572, 1985; Takai et al, J. Immunol. 137:3494–3500, 1986; Bowmanet al., J. Virology 61:1992–1998; Takai et al, J. Immunol. 140:508–512, 1988; Bertagnolli et al, Cellular Immunology 133:327–341, 1991; Brown et al, J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J Immunol. 134:536–544, 1995; Inaba et al., Journal of Experimental Medicine 173:549–559, 1991: Macatonia et al, Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al, Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al, Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al, Blood 85:2770–2778, 1995; Toki et al., Proc. Nat. Acad Sci. USA 88:7548–7551, 1991.

6.3.5. Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e, traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoictic cells and therefore find therapeutic utility in various stem cell disorders (such as those usually treated with transplantation. including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al eds. Vol pp. 23–39, Wiley-Liss, Inc., New York, N.Y. 1994: Neben et al., Experimental Hematology 22:353–359, 1994: Cobblestone area forming cell assay, Ploemacher, R. E. In Culture of Hematopoietic Cells. R. I. Freshney, et al eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al eds. Vol pp. 163–179, Wiley-Liss, Inc., New York, N.Y. 1994, Long term culture initiating cell assay, Sutherland, H. J. In Culture of Hematopoietic Cells. R. I. Freshney, et al. eds. Vol pp. 139–162, Wiley-Liss, Inc., New York, N.Y. 1994

6.3.6. Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells, or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); international Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

6.3.7. Activin/Inhibin Activity

A protein of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin $\alpha$-family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

6.3.8. Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al J. Clin. Invest. 95:1370–1376, 1995; Lind et al. APMIS 103:140–146, 1995; Muller et al Eur. J. Immunol. 25:1744–1748; Gruber et al J. of Immunol. 152:5860–5867, 1994; Johnston et al J. of Immunol. 153:1762–1768, 1994.

6.3.9. Hemostatic and Thrombolytic Activity

A protein of the invention may also exhibit hemostatic or thrombolytic activity. A polynucleotide of the invention can encode a polypeptide exhibiting such attributes. Such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al, Thrombosis Res. 45:413–419, 1987; Humphrey et al., Fibrinolysis 5:71–79 (1991); Schaub, Prostaglandins 35:467–474, 1988.

6.3.10. Receptor/Ligand Activity

A protein of the present invention may also demonstrate activity as receptors, receptor ligands or inhibitors or agonists of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell—cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

6.3.11. Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell—cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation intimation associated with infection (such as septic shock, sepsis or systemic inflammatory response syndrome (SIRS)), ischemia-reperfision injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

6.3.12 Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myclocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, *Medicine,* 2d Ed., J. B. Lippincott Co., Philadelphia).

6.3.13. Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyclinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980. Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

6.3.14 Cancer Diagnosis And Therapy

The demonstration that EGFL6 promotes proliferation of cells and its highly specific and significant expression in cancer cells indicates not only that detection of EGFL6 polynucleotides and polypeptides (including variants thereof) are useful for diagnostic purposes, but also indicates that cell proliferation, and preferably cancer cell generation, proliferation and metastasis, can be inhibited using compounds that inhibit the activity of EGFL6. Such compounds include antisense polynucleotides, antibodies (including polyclonal antibodies, monoclonal antibodies, fragments thereof, chimeric antibodies, single chain antibodies, humanized antibodies, and human antibodies) and small molecule compounds that inhibit EGFL6 by binding to EGFL6 or by inhibiting interaction between EGFL6 and its receptor. Such compounds that bind EGFL6 polypeptides (including variants) can be identified using any methods known in the art, including by testing the compound for ability to inhibit EGFL6-induced cell proliferation.

Polypeptides of the invention may be involved in cancer cell generation, proliferation or metastasis. Detection of the presence or amount of polynucleotides or polypeptides of the invention may be useful for the diagnosis and/or prognosis of one or more types of cancer. For example, the presence or increased expression of a polynucleotide/polypeptide of the invention may indicate a hereditary risk of cancer, a precancerous condition, or an ongoing malignancy. Conversely, a defect in the gene or absence of the polypeptide may be associated with a cancer condition. Identification of single nucleotide polymorphisms associated with cancer or a predisposition to cancer may also be useful for diagnosis or prognosis.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions of the invention may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, sarcomas including fibrosarcoma and osteosarcoma, skin cancers including malignant melanoma, tumor progression of human skin keratinocytes, squamous cell carcinoma, basal cell carcinoma, hemangiopericytoma and Karposi's sarcoma.

Polypeptides, polynucleotides, or modulators of polypeptides of the invention (including inhibitors and stimulators of the biological activity of the polypeptide of the invention) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anticancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxundine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethyhmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g exposure to carcinogens) known in the art that predispose an individual to developing cancers. Under these circumstances, it may be beneficial to treat these individuals with therapeutically effective doses of the polypeptide of the invention to reduce the risk of developing cancers.

In vitro models can be used to determine the effective doses of the polypeptide of the invention as a potential cancer treatment. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921–30 (1974), mobility and invasive potential of tumor cells in Boyden Chamber assays as described in Pilkington et al., Anticancer Res., 17: 4107–9 (1997), and angiogenesis assays such as induction of vascularization of the chick chorioallantoic membrane or induction of vascular endothelial cell migration as described in Ribatta et al., Intl. J. Dev. Biol., 40: 1189–97 (1999) and Li et al, Clin. Exp. Metastasis, 17:423–9 (1999) respectively. Suitable tumor cells lines are available, e.g. from American Type Tissue Culture Collection catalogs.

6.3.15. Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

6.4. Pharmaceutical Formulations and Routes of Administration

A protein of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the invention in such multimeric or complexed form.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoictic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

6.4.1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

6.4.2. Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein of the present invention is administered orally, protein of the present invention will be in the form of a tablet, capsule, powder, solution or elixir When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution. dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity charactenstics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the proteinase inhibiting compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminatephosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

Delivery of a functional EGFL6 gene to appropriate cells may be effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp. 25–20 (1998). For additional reviews of gene therapy technology see Friedmann, Science, 244: 1275–1281 (1989); Verma, Scientific American: 68–84 (1990); and Miller, Nature, 357: 455–460 (1992). Alternatively, it is contemplated that in other human disease states, preventing the expression of or inhibiting the activity of EGFL6 or mutants thereof will be useful in treating the disease states. It is contemplated that antisense therapy or gene therapy could be applied to negatively regulate the expression of EGFL6.

6.4.3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1.Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

6.4.4. Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6.5. Antibodies

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1–21 (1990); Kohler and Milstein, Nature 256:495–497 (1975)), the trioma technique, the human B-cell hybridoma technique (Kozbor et al., Immunology Today 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Research. 175:109–124 (1988)).

Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures. The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

6.6. Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention. By providing the nucleotide sequence of SEQ ID NOS:1, 2, 5 or 23 or a representative fragment thereof, or a nucleotide sequence at least 99.9% identical to SEQ ID NOS:1, 2, 5 or 23 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

6.7. Triple Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

6.8. Diagnostic Assays and Kits

The present invention further provides methods to identify the presence or expression of one of the ORFs of the present invention, or homolog thereof, in a test, using a nucleic acid probe or antibodies of the present invention.

In general, methods for detecting a polynucleotide of the invention can comprise contacting a with a compound that binds to and forms a complex with the polynucleotide for a period sufficient to form the complex, and detecting the complex, so that if a complex is detected, a polynucleotide of the invention is detected in the. Such methods can also comprise contacting a under stringent hybridization conditions with nucleic acid primers that anneal to a polynucleotide of the invention under such conditions, and amplifying annealed polynucleotides, so that if a polynucleotide is amplified, a polynucleotide of the invention is detected in the.

In general, methods for detecting a polypeptide of the invention can comprise contacting a with a compound that binds to and forms a complex with the polypeptide for a period sufficient to form the complex, and detecting the complex, so that if a complex is detected, a polypeptide of the invention is detected in the.

In detail, such methods comprise incubating a test with one or more of the antibodies or one or more of nucleic acid probes of the present invention and assaying for binding of the nucleic acid probes or antibodies to components within the test.

Conditions for incubating a nucleic acid probe or antibody with a test sample will vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al. Techniques in Immunocytochemistry, Academic Press, Orlando, Fla. Vol. 1 (1982). Vol. 2(1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test s-samples of the present invention include cells, protein or membrane extracts of cells, or biological fluids such as sputum, blood, serum, plasma, or urine. The test samples used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the s and reagents are not cross-contaminated, and the agents or solutions of each container can be added in a quantitative fashion from one compartment to another. Such containers will include a container which will accept the test, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

6.9. Screening Assays

Using the isolated proteins and polynucleotides of the invention, the present invention further provides methods of obtaining and identifying agents which bind to a polypeptide encoded by the ORF from a polynucleotide with a sequence of SEQ ID NOS:1, 2, 5 or 23 to a specific domain of the polypeptide encoded by the nucleic acid, or to a nucleic acid with a sequence of SEQ ID NOS:1, 2, 5 or 23. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In Synthetic Peptides, A User's Guide, W. H. Freeman, NY (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents. Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

6.10. Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NOS: 1, 2,5, or 23. Because the corresponding gene is only expressed in a limited number of tissues, especially adult tissues, a hybridization probe derived from SEQ ID NOS: 1,2,5, or 23 can be used as an indicator of the presence of RNA of cell type of such a tissue.

Any suitable hybridization technique can be employed, such as, for example, in situ hybridization. PCR as described U.S. Pat. Nos. 4,683,195 and 4,965,188 provides additional uses for oligonucleotides based upon the nucleotide sequences. Such probes used in PCR maybe of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals. The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search. Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology that were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid [between the query and reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

7. EXAMPLES

7.1. Example 1

A Novel Nucleic Acid Sequence Obtained from a cDNA Library of Fetal Liver-Spleen Encoding an EGF-Receptor Like Protein.

A plurality of novel nucleic acids were obtained from cDNA libraries prepared from various human tissues including fetal skin, fetal liver spleen, and lung tumor, and in some cases genomic libraries derived from human chromosome, as described in Bonaldo et al., Genome Res. 6:791–806 (1996), using standard PCR, SBH sequence signature analysis and Sanger sequencing techniques. The inserts of the library were amplified with PCR using primers specific for vector sequences which flank the inserts. These s-samples were spotted onto nylon membranes and screened with oligonucleotide probes to give sequence signatures. The clones were clustered into groups of similar or identical sequences, and single representative clones were selected from each group for gel sequencing. In some cases the 5' sequence of the amplified inserts was then deduced using the reverse M13 sequencing primer in a typical Sanger sequencing protocol. PCR products were purified and subjected to fluorescent dye terminator cycle sequencing. Single pass gel sequencing was done using a 377 Applied Biosystems (ABI) sequencer. In some cases, RACE was performed to further extend the sequence. Two (2) of these inserts from the $b^2$HFLS20W cDNA library prepared from human fetal liver-spleen tissue, as described in Bonaldo et at, Genome Res. 6:791–806 (1996) have been identified as novel sequences not previously obtained from this library, and not previously reported in public databases. These sequences are shown in FIG. 2 as SEQ ID NO. 1-2. The polypeptide sequence corresponding to the nucleic acid sequence of SEQ ID NO: 1 is shown in FIG. 2 as SEQ ID NO: 3. The polypeptide sequence corresponding to SEQ ID NO: 2 is shown in FIG. 2 as amino acid residues 1–502 of SEQ ID NO: 4 as the designation "NNN" in SEQ ID NO: 2 represents a sequence ambiguity. These amino acid sequences contain EGF motifs that have striking homology to the EGF motifs of Notch (from drosophila) and CD97.

Epidermal growth factor and transforming growth factor transmit their signals for cellular growth through EGF-R via an intracellular tyrosine kinase domain. Signaling through EGF induces cell division. Mutated forms of EGF have been demonstrated to be involved in various cancers owing to a lack of regulation in cell division signaling (Carter et al., Crit Rev Oncog 1994;5(4):389–428, Chrysogelos, et al., Breast Cancer Res Treat Jan. 29, 1994; (1):29–40). This has provided the opportunity to use EGF and other ligands of EGF-R as therapeutic targets for human cancers (Rusch, et al., Cytokine Growth Factor Rev August 1996; 7(2): 133–141). Mice with targeted mutations to both alleles of the EGF receptor gene die very young after birth from multiorgan failure revealing EGF receptor as essential mammalian protein (Miettinen, et al., Nature 1995 July 27;376( ):377–341). Notch is a receptor protein initially identified in drosophlia (Kidd, et al., Mol Cell Biol September 1986; 6(9):3094–3108).

The Notch family of transmembrane receptor proteins are key developmental regulators. Mutations in mammalian Notch genes have been implicated in leukaemia, breast cancer, stroke and dementia (Panin, et al., Nature Jun. 26, 1997;387(6636):908–912). The extracellular domain of Notch contains 36 EGF-like repeats, a transmembrane domain and three other repetative elements (Kidd, et al., Mol Cell Biol September 1986; 6(9):3094–3108).

CD97 is a surface molecule expressed mainly on leukocytes. It has five EGF-like domains and seven transmembrane domains, a defining feature of G protein-coupled receptors (Gray, et al., Journal of Immunology 1996 157:5438–5447). It also has a RGD motif (involved in binding to integrin molecules) and eight potential N-linked glycosylation sites. CD97 has links to cancer (it is a dedifferentiation marker of human thyroid carcinomas; Aust, et al, Cancer Res May 1, 1997;57(9):1798–1806) and inflammation (Gray, et al., Journal of Immunology 1996 157:5438–5447).

Additional sequences SEQ ID Nos: 27, 29 and 31 were assembled from sequences obtained as described above or from one or more public databases. The nucleic acids were assembled using an EST sequence as a seed. Then a recursive algorithm was used to extend the seed EST into an extended assemblage by pulling additional sequences from different databases (i.e., Hyseq's database containing EST sequences, dbEST version 114, gb pri 114 and UniGene version 101) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater then 95%.

Using PHRAP (University of Washington) or CAP4 (Paracel), a full length cDNA sequence and its corresponding protein sequence were generated from the assemblage. Any frame shifts and incorrect stop codons were corrected by hand editing. During editing, the sequence was checked using FASTY and/or BLAST against Genbank (i.e., dbEST version 117, gb pri 117, UniGene version 117, Genepet release 117). Other computer programs which may have been used in the editing process were Phred-Phrap and Consed (University of Washington) and ed-ready, ed-xt anf gc-zip-2 (Hyseq, Inc.).

7.2. Example 2

Expression Studies with SEQ ID NOS 1–2.

To determine if SEQ ID No. 2 is expressed specifically in diseased or normal human tissues, a Northern blot analysis was performed. The entire cDNA insert was labeled with radioisotope using a multiprime labeling method. A high stringency wash was performed to ensure specific hybridization. The resultant hybridization pattern produced a total of five different bands (approximately 6.5, 4.0, 2.1, 0.5 and 0.2 kb). Two of these bands (6.5 and 4 kb) were uniquely expressed in a sample derived from a brain tumor (astrocytoma of cerebellum) and not in a panel of samples from 19 other tissues (normal brain, kidney tumor and normal kidney, liver tumor and normal liver, lung tumor and normal lung, normal heat, pancreas, spleen and skeletal muscle and fetal brain, liver, lung, and skeletal muscle). The other 3 bands were expressed to varying degrees in the other tissues. These results indicate that the two higher molecular weight bands are specific to the brain tumor tissue and not to the other samples surveyed. As EGF-motif containing receptors have been previously been linked to the progression of various cancers, we believe that the full length message to SEQ ID No. 2 is involved in brain tumor development In addition, cDNA libraries prepared from a wide variety of tissue types were surveyed for expression of SEQ ID NO:5 or 23 (EGFL6) using a screening by hybridization approach. The expression level (mRNA transcript frequency) of a gene is determined by dividing the number of clones corresponding to that gene (cluster size) by the total number of clones analyzed in the cDNA library survey. EGFL6 expression was detected only in lung tumor and a subset of fetal libraries at the following transcript frequencies: 0.003% of lung tumor (adenocarcinoma), 0.01% of fetal lung, 0.007% of fetal skin, 0.006% of fetal umbilical cord, 0.0035% of fetal liver-spleen and 0.0027% of placenta, with the total number of cDNA transcripts ranging from about 10 to 30 copies per cell in these six libraries. In contrast, none of the normal adult tissues, including lung, express EGFL6 transcript at a detectable level.

To expand the survey of tumor tissues, a further Northern blot analysis of mRNA from normal and cancer tissues was performed. To eliminate the possibility of cross-hybridizing to other EGF motif-containing sequences, the probe used was generated from sequences outside of the EGF repeat region (nucleotides 1105–1906 of SEQ ID NO: 5). This 801 bp probe was amplified by PCR using gene specific primers (5'-CCAGAACCCACCAGGACTCC-3', SEQ ID NO: 21; 5'-GGGAACTGACATACAAAGTC-3', SEQ ID NO: 22) and labeled using the Prime-IT® II Random Primer Labeling Kit from Stratagene (LA Jolla, Calif.) in the presence of [$^{33}$P]-α-dCTP. A high stringency hybridization and wash was performed to ensure specific hybridization, using the ExpressHyb™ hybridization solution (Clontech, Palo Alto, Calif.) according to the instructions of the manufacturer. A human multiple tissue Northern blot (Clontech) and a human brain tumor blot (Invitrogen, Carlsbad, Calif.) were tested. The results showed a single band (approximately 2.4 kb) expressed specifically in placenta and meningioma tumor tissues. All other normal tissues (brain, heart, skeletal muscle, colon, thymus, spleen, kidney, liver, small intestine, lung and peripheral blood leukocytes), glioma brain tumor tissue and malignant lymphoma tumor tissue did not yield a signal. The same panels were probed with a β-actin specific probe as a positive control, and all tissues yielded a signal with this probe.

7.3. Example 3

Use of Molecules Which Bind SEQ ID NOS. 3–4.

Molecules which bind SEQ ID Nos. 3, 4, 6 or 24 or amino acid residues 1–502 of SEQ ID NO: 4 will include, e.g., monoclonal antibodies and and other small molecules which act as blocking agents, or as activators. See above. These molecules are identified as agonists or antagonists of SEQ ID Nos. 3, 4, 6, or 24 or amino acid residues 1–502 of SEQ ID NO: 4 by the following types of assays. Tumor cell lines which are well known in the art, e.g., astrocytoma cell line 1321N1, are cultured in the presence of the binding molecules, and antagonist or agonist activity is identified by changes in the growth rate of the tumor cells. In one embodiment, the binding molecule is an antagonist which causes cell death.

Antibodies or other suitable binding molecules which bind to SEQ ID Nos. 3, 4, 6, or 24 or amino acid residues 1–502 of SEQ ID NO: 4 are also useful in receptor protein purification and for in situ hybridization analyses. Initial in situ analyses identify associations between the expression of SEQ ID Nos. 3, 4, 6, or 24 or amino acid residues 1–502 of SEQ ID NO: 4 and genetic disorders of the immune system or development. In situ hybridization with these binding molecules then diagnoses these genetic disorders of the immune system or development in patients.

7.4. Example 4

SEQ ID NOS. 5 of 23 and 6 or 24

SEQ ID NO. 5 (FIG. 4) is a 5' and 3' extension of the original cDNA sequence, SEQ ID NO. 2. In the 5' direction, additional sequence was obtained by a PCR based method of extending 5' sequence information from truncated cDNAs called 5' RACE (Rapid Amplification of cDNA Ends) (Frohman, M. A., Dush, M. K. and Martin, G. R., (1988) Proc. Natl. Acad. Sci. USA 85, 8998–9002). Fetal Liver Marathon-Ready cDNA (Clontech) was used as template for PCR reactions. Adaptor primer AP1 provided by Clontech was used as the 5' PCR primer, a gene-specific primer 10244-52 (5'-CTCATCCTCAAGCCCCT CTTT-3', SEQ ID NO:12) was used as the 3' PCR primer. The products of this PCR reaction were diluted 100 fold and used as a template for a nested PCR reaction with API as the 5' primer and another gene specific primer 10244-51 (5'-CCATGAGAGTTCCCGCCTCTG-3', SEQ ID NO:13) as the 3' primer. The products of this PCR reaction were cloned into the pGEM®-T Easy vector using the pGEM®-T Easy Vector System (Promega) as instructed in the user manuel. Bacterial suspensions of individual colonies derived from this cloning reaction were used as template for PCR reactions using vector primers (T7: 5'-GTAATACGACTCACTATAGGG-3', SEQ ID NO:14, SP6: 5'-ATTTAGGTGACACTATAGAAGG-3', SEQ ID NO:15) to generate DNA fragments for sequencing reactions. Using the same primers as in the PCR reactions (T7 and SP6), these DNA fragments were sequenced using the BigDYE terminator (Perkin Elmer ABI) cycle sequencing reactions (Sanger dideoxy). 138 nucleotides are contiguous with the original cDNA sequence SEQ ID NO: 2 on the 5' end. Based on these additional sequences, two additional gene specific primers were designed (10244-A: 5'-CCCAGGCTGACGTGCCGATGC-3', SEQ ID NO:16; 10244-B: 5'-GCAGCAGGCCAGTTTAGTTCC-3', SEQ ID NO:17), and these were used to repeat the 5' RACE process.

Fetal Liver Marathon-Ready cDNA (Clontech) was used again as template for PCR reactions with primers AP1 and the gene-specific primer 10244-B. The products of this PCR reaction were used as a template for the nested PCR reaction wtih AP1 as the 5' primer and the gene specific primer 10244-A as the 3' primer. The products of this PCF reaction were similarly cloned into the pGEM®-T Easy vector and inserts of individual colonies were similarly sequenced. Additional nucleotide sequences were obtained from sequencing reactions that produced sequnces that are contiguous with the sequence obtained above to complete SEQ ID NO. 5 (2365 bp) as shown in FIG. 4.

SEQ ID NO: 6 (FIG. 4) is the amino-acid translation from nucleotide 205 to 1866 of SEQ ID NO: 5, including the starting methionine and stop codon. The first 21 amino-acids comprise the hydrophobic region that represents the signal peptide. EGF motifs are located at amino acid residues 80–93 of SEQ ID NO:6 (EGF motif 1), amino acid residues 95–123 of SEQ ID NO:6 (EGF motif 2), amino acid residues 133–168 of SEQ ID NO:6 (EGF motif 3), amino acid residues 175–2 14 of SEQ ID NO:6 (EGF motif 4), amino acid residues 220–259 (EGF motif 5). A hydrophobic region suggestive of a possible transmembrane domain is located at amino acid residues 446–465 of SEQ ID NO:6, two potential N-glycosylation sites at amino acid residues 247 and 346 of SEQ ID NOS: 6 or 24, a potential tyrosine phosphorylation site at amino acid residue 509 of SEQ ID NOS: 6 or 24, and a RGD motif at amino acid residues 363–365 of SEQ ID NO:6.

The presence of an RGD motif predicts an interaction with integrins. The putative tyrosine phosphorylation motif suggests that the molecule might act as a kinase substrate, so that phosphorylation could be used to regulate EGFL6 expression or to modulate its function.

Further analysis of the deduced amino acid sequence of SEQ ID NOS: 6 or 24 using SignalP prediction [Nielsen et at, Protein Eng., 10:1–6(1997)] indicates that an 18-amino acid putative signal peptide region is located at the N-terminus. Further analysis of the hydrophobic portions ax the C-terminus by the TMHMM server Center for Biological Sequence Analysis, Technical University of Denmark, Lyngby, Denmark) indicate that these portions do not encode typical transmembrane domains. The presence of a signal peptide and the absence of a typical transmembrane domain suggests that this protein actually is secreted.

Thus, SEQ ID No. 1 encodes the polypeptide sequence of SEQ ID Nos. 3 which contains EGF motifs that are similar to the EGF motif of the drospophila developmental gene Notch (32% amino acid sequence homology), the EGF motif of CD97 (38% amino acid sequence homology), and the EGF consensus motif (26% amino acid homology). SEQ ID No 1 is an EST for a family member of the EGF-containing genes with most similarity to the EGF motifs of drosophila Notch and human CD97.

Likewise SEQ ID No. 5 encodes the polypeptide sequence of SEQ ID No. 6 which is similar in protein sequence to the EGF motif of the drospophila developmental gene Notch (31% amino acid sequence homology), the EGF motif of CD97 (34% amino acid sequence homology), and the EGF consensus motif (24% amino acid homology). The protein sequence also has homology to latent TGF (a protein implicated in osteoporosis).

In general, the content and position of certain highly conserved amino acid residues identifies SEQ ID No. 6 as a member of the EGF-repeat containing family (conserved amino acid residues are shown in FIG. 1). Six cysteines and two glycines are highly conserved among EGF-repeats which define an EGF motif. Four cysteines and one glycine are absolutely conserved in the consensus sequence from known EGF-repeat domains. The four and a half EGF motifs in SEQ ID No. 6 contain the cysteines and the one glycine residue with the appropriate spacing between these residues. Thus, SEQ ID No. 6 is properly classfied as a protein containing the EGF-repeat motif. SEQ ID No. 6 has the highest amino acid similarity to CD97, but the conserved residues of the motif are most similar to drosophila Notch. As noted above, resequencing of plasmids pEGFR-HY2 and pEGFR-HY3 showed that a sequence error had been reported in SEQ ID NOS: 5 and 6 which has been corrected in SEQ ID NOS: 23 and 24.

7.5. Example 5

Chromosomal Localization OF SEQ ID NOS: 5 OR 23 (EGFL6)

The chromosomal location of EGFL6 was mapped as follows: PCR primers (5'-GTCATTTCTGAATCTTTCCAC-3', SEQ ID NO: 19 and 5'-GAAATGTTGCAGAGAGAAGCTC-3', SEQ ID NO: 20) specific for the 3' untranslated region were used to screened against the NIGMS human/rodent somatic cell hybrid mapping panel #2 [Drwinga et al., Genomics, 16:311–314 (1993)]. This PCR yielded a 117-nucleotide product using the following conditions: initial denaturation for 2 mm at 94° C. followed by 40 cycles of amplification at 94° C. for 30 sec., 54° C. for 1 min. and 72° C. for 1 min. The analysis revealed that EGFL6 localized to chromosome X. Interestingly, aberrations to chromosome X have been implicated in both meningiomas and lung tumors [Dave et al., Cancer Genet. Cytogenet., 87:35–38 (1996); Lekanne Deprez et al., J. Neuropathol. Exp. Neurol. 54:224–235 (1995); Amo-Takyi et al, Histopathology 34:163–169 (1999), all of which are incorporated by reference herein].

7.6 Example 6

In Situ Hybridization with EGFL6

In situ hybridization studies were performed to determine if the EGFL6 transcript is differentially expressed in tumor tissues as compared to normal tissues. In situ hybridization was carried out in the following human tissues: placenta, normal tonsil, normal prostate, prostate carcinoma, normal colon, colon carcinoma, normal lung, lung carcinoma, normal breast and breast carcinoma. Each carcinoma tissue type included s from 3 different patients.

The in situ hybridization analysis was carried out with digoxigenin (DIG) labeled riboprobes derived from the EGFL6 cDNA sequence (SEQ ID NO: 23). PCR was used to generate a 384 nucleotide fragment of EGFL6 cDNA corresponding to nucleotides 1667–2050 of SEQ ID NO: 32, using primer L6riboB5; (CCCTGGCATGGGAGAAGACCAC; SEQ ID NO: 25) and primer L6riboB3; (GTGATATGATATTTAAAGCAAATATTGGCA; SEQ ID NO: 26). The PCR product was subcloned into the pCR™II-TOPO plasmid (Invitrogen) and sense and antisense RNA were generated. The resulting riboprobes were labeled with the DIG RNA Labeling kit according to the manufacturer's instructions (Roche Molecular Biochemicals). Automated in situ hybridization was performed by QualTek Molecular Labs (Santa Barbara, Calif.) using a modified version of a previously published procedure (Myers et al., *J. Surg. Pathol.* 1: 191–203, 1995). The Ventana Medical Systems, Inc. (Tuscan, Ariz.) TechMate™ Automated Staining System was used for the automated in situ procedure.

All tissues were fixed in 10% neutral buffer formalin, paraffin-embedded and cut into 4 μm thick sections. The sections were placed on ChemMate™ Capillary Slides (Ventura; cat no. POP75), and the slides were hybridized with the antisense and sense riboprobes. DIG labeled riboprobes bound to the slides were detected with sheep anti-DIG antibodies bound to alkaline phosphatase. The slides were then stained with chromagen BCIP/NBT (blue color) and counter stained with Eosin (pink stain in cytoplasm) for 2 hours. The results are summarized in Table 1.

TABLE 1

| Tissue | Conc. of Probe | Expression |
|---|---|---|
| Placenta | 2.0 ng/ml | Epithelial cells and while blood cells |
| Normal Tonsil | 1.0 ng/ml | White cells including cells undergoing mitosis |
| Normal Lung | 1.0 ng/ml | None |
| Lung Carcinoma | 0.5 ng/ml | Tumor cells with polarized distribution towards the lumen |
| Normal Prostate | 1.0 ng/ml | None |
| Prostate Carcinoma | 1.0 ng/ml | Very strong signal observed. Tumor cells with polarized distribution towards the lumen |
| Normal Breast | 1.0 ng/ml | Light staining in the epithelial cells |
| Breast Carcinoma | 1.0 ng/ml | Very strong signal observed. Polarized cytoplasmic staining of tumor cells. |
| Normal Colon | 1.0 ng/ml | None |
| Colon Carcinoma | 0.05 ng/ml | Very strong signal observed. Strong cytoplasmic staining in tumor cells. |

TABLE 1-continued

In summary, differential expression of the EGFL6 transcript was detected in placenta, tonsil, prostate carcinoma, colon carcinoma, lung carcinomas, breast carcinoma and to a lesser extent in normal breast. Very strong signals were detected in prostate, breast and colon carcinoma. The EGFL6 transcript did not appear to be expressed in normal prostate, normal colon or normal lung. The sense riboprobe only produced background staining in all tissues tested. β-actin antisense detection in normal prostate tissue was used as a positive control.

7.7 Example 7

In Vitro Proliferation Assay Using EGFL6

In vitro proliferation assays were performed to determine whether EGFL6 was capable of inducing cell division. CHO-K1 cells in exponential phase were harvested and seeded into 12-well plates in F12K medium (Gibco) containing 10% fetal bovine serum at a concentration of $1\times10^5$ cells/well. The cells were then transiently transfected by adding a mixture of 1.5 μl of FuGene6 reagent (Roche) and 0.5 μg of plasmid DNA to the cells in each well. Cells were either transfected with pcDNA 3.1/myc-His vector alone (Invitrogen) or with pcDNA 3.1-EGFL6-myc-His (pcDNA 3.1/myc-His vector into which DNA encoding EGFL6 was cloned). The pcDNA 3.1/myc-His vector contains a myc epitope and a His tag, both of which are located 3' to the multiple cloning site. Thus, pcDNA 3.1/myc-His vector into which DNA encoding EGFL6 was cloned in frame with the myc epitope and His tag, expresses an EGFL6 protein that has a myc tag followed by a His tag at the C-terminus. Western blot analysis using an anti-myc antibody confirmed that the EGFL6 protein was expressed by cells transfected with pcDNA 3.1-EGFL6-myc-His DNA. All transfections were carried out in triplicates. Forty eight hours after transfection, cells from each well were suspended using trypsin and counted using a hemocytometer. Results from these experiments demonstrated that cells expressing EGFL6 divide 2–3 times faster than cells expressing vector alone, suggesting that EGFL6 stimulates cell division.

The above transfection experiments were repeated in CHO-K1 cells using pcDNA3.1 His-myc or pcDNA3.1-EGFL6-His-myc. Twenty four hours after transfection, stably transfected cells were selected against 600 μg/ml of G418 for 10 days. Transfected cells were measured for their proliferation rates. Results demonstrated that cells expressing EGFL6-His-myc divided every 18 hours while cells expressing vector alone doubled every 42 hours, confirming that EGFL6 stimulates cell growth.

7.8 Example 8

Additional In Situ Hybridization Analysis of EGFL6 Expression in Cancer Tissue Additional in situ hybridization studies were carried out to analyze expression of EGFL6 transcript in a variety of cancer tissues. In situ hybridization was carried out as described in Example 6 in the following human tissues: prostate adenocarcinoma, normal prostate, colorectal carcinoma, normal colon, melanoma, normal skin, lymphoma, normal lymph nodes, sarcoma, normal skeletal and smooth muscle, meningioma, neuroblastoma, astrocytoma and normal brain.

Fourteen prostate adenocarcinoma tissue samples of various grades and stages were collected from different patients and analyzed with 3 samples of normal prostate tissue. Strong EGFL6 transcript expression was detected in 100% of the prostate adenocarcinoma tissues. Expression was detected in low Gleason Grade samples. EGFL6 expression was not detected in any normal prostate samples tested.

Sixteen colorectal carcinoma tissue samples of various grades were collected from different patients and analyzed with 3 samples of normal colon tissue. 81.25% of the colon carcinoma tissues were positive for EGFL6 expression including the low grade samples. EGFL6 transcript expression was not detected in any normal colon samples tested. In addition, EGFL6 transcript expression was detected in the plasma cells, lymphocytes and endothelial cells in the lamina propria and in the transition areas where dysplasia and carcinoma were closest.

Four melanoma tissue samples of various stages and sites of origin were collected from different patients and analyzed with one of normal skin tissue. 75% of the melanoma tissues were positive for EGFL6 transcript expression including the low stage samples. EGFL6 transcript expression was not detectable in the normal skin tissue samples tested.

Three lymphoma samples of various stages collected from different patients were analyzed with one sample of normal lymph node tissue. 66.7% of the lymphoma tissue samples were positive for EGFL6 transcript expression. EGFL6 transcript expression was not detectable in normal lymph node tissue tested.

Three sarcoma samples of various stages collected from different patients were analyzed with one sample of normal skeletal and smooth muscle tissue. 33.3% of the sarcoma tissues were positive for EGFL6 expression. EGFL6 expression was not detectable in normal skeleton and smooth muscle samples tested.

Three brain tumor samples of various types were collected from different patients and analyzed along with one sample of normal brain tissue. 66.7% of the brain tumor samples (menigioma and astrocytoma) were positive for EGFL6 transcript expression. EGFL6 transcript expression was not detectable in the sample normal brain tissue tested.

7.9 Example 9

Detection of EGFL6 Protein Expression in Colorectal Cancer

EGFL6 mRNA was detected in colorectal cancer tissues (see Examples 6 and 8) d therefore it was of interest to determine if EGFL6 protein correlates with EGFL6 transcript expression in colorectal cancer tissue. The immunohistochemical analysis was carried out as follows by QualTeck Molecular Laboratories (Santa Barbara, Calif.) with a polyclonal anti-human EGFL6 antibody directed against the EGFL6 peptide QDREDDFDWNPADR (SEQ ID NO: 33). The tissues used for the immunohistochemistry were obtained from the same paraffin blocks as those samples in Example 8 but the sections were cut from a different level of the cut sections and therefore the tissue s were similar but not identical.

Fourteen colorectal cancer samples of various grades and stages and three normal colorectal tissues were fixed in 10% neutral buffer formalin, paraffin-embedded and cut into 4 μm thick sections. Tissue sections were deparrifrinized by 4 immersions in xylenes followed by a an immersion in a graded alcohol series to distilled water.

To enhance epitope recovery, the tissues underwent steam induced epitiope recovery with a retrieval solution. several different SHIER solutions with and without enzyme digestion at two different concentrations. The tissues were heated in the capillary gap in the upper chamber of a Black and Decker Steamer as described in Ladner et al (*Cancer Reserach,* 60: 3493–3503, 2000).

Automated immunohistochemistry was carried out with the TECHMATE 1000 or TECHMATE 500 (BioTek Soultions, Ventura Medical System). Specifically, the tissues were then blocked with 3% and 10% normal goat serum for 15 and 30 minutes respectively. Subsequently, the tissues were incubated with the primary antibody (anti-EGFL6 polyclonal antibody) for 60 minutes at 3.0 μg/ml. Then the tissues were stained with the biotinylated goat-anti-rabbit IgG secondary antibody for 25 minutes. Optimal results were obtained with the overnight incubation. To ensure the staining procedure was working appropnately, anti-vimentin was used as a positive control and rabbit IgG was used as a negative control.

The antibody binding was then detected by an avidin-biotin based tissue staining system where horse-radish peroixidase was used as a reporter enzyme and DAB (3,3'-Diaminobenzididine Tetrahydrochloride) was used as a chromogen. Specifically, the endogenous peroxides were blocked for 30 minutes, the avidin-biotin complex reagent was added and then the tissues were incubated in DAB for a total of 15 minutes. Finally, the tissues were counterstained with hemotoxylin to assess cell and tissue morphology.

After staining, the slides were dehydrated through an alcohol series to absolute ethanol followed by xylenes rinses. The slides were permanently covered with glass coverslips and permount. The tissues were examined visually under a light microscope.

Fourteen samples of colorectal carcinoma tissues of various grades were collected from different patients and analyzed with 3 samples of normal colon tissue. 71% of the colon carcinoma tissues were positive for EGFL6 protein expression, including the low grade samples, and expression was mainly localized in the cytoplasm. EGFL6 protein and mRNA expression was not detectable in any of the normal colon samples. Three of the tumor samples negative for EGFL6 protein expression were found to express EGFL6 mRNA in Example 8. One tumor positive for EGFL6 protein expression was found negative for EGFL6 mRNA expression in Example 8. Lymphocytes in the lamina propia were positive for EGFL6 protein expression similar to EGFL6 transcript expression. This immunohistochemical analysis demonstrates EGFL6 protein expression correlates with the detected EGFL6 transcript expression in colon carcinoma.

7.10 Example 10

Production and Purification of Recombinant EGFL6-Fc Fusion Protein

A. Preparation of EGFL6-Fc Constructs

To prepare constructs with express the EGFL6-$IgG_4$ Fc fusion protein (EGFL6-Fc), EGFL6 cDNA (SEQ ID NO: 23) within the pcDNA3.1 vector was digested with the restriction enzymes HindIII and XhoI, purified, and ligated into a pDEF2S-Fc vector which was linearized by the same enzymes. This ligation generated a EGFL6 cDNA fragment linked in-frame to the Fe cDNA at the 3' end. The EGFL6-Fc cDNA fragment was excised from the pDEF2S-Fc vector with the restriction enzyme SfiI and ligated into the pDEF38 vector which was pre-cut with SfiI. The orientation of EGFL6-Fc cDNA fragment in the pDEF38 vector was determined by sequencing using standard sequences methods known in the art with a primer (atctgtctaatggcgttgg; SEQ ID NO: 33) that flanks the SfiI site of the promoter region. EGFL6-Fc cDNA sequence was verified with standard DNA sequencing methods known in the art. EGFL6-Fc protein expression was confirmed by Western blots on conditioned media collected from COS-7 cells (ATCC accession no. CRL-1651) transiently transfected with the EGFL6-Fc cDNA.

B. Expression of EGFL6-Fc in COS-7 Cells

EGFL6-Fc cDNA was stably transfected into Cos-7 cells for recombinant expression. Initially, Cos-7 cells were seeded into 25 dishes (150 $mm^5$) at $4\times10^6$ cells/dish. On the following day, the cells were transfected with the Fugene-6 reagent (Roche Molecular Biochemical) according to the manufacturer's instructions. For each dish, 100 μl of Fugene-6 and 30 μg of EGFL6-Fc cDNA were added to 2 ml of DMEM media and incubated at room temperature for 20 minutes. Subsequently, the 2 ml of DNA-Fugene mixture was added dropwise to each dish and the cells were incubated at 37° C. in a 5% $CO_2$ incubator for 24 hours. The cells were then washed with PBS and fresh Hyclone PF—CHO serum free medium was added. After a 72 hour incubation at 37° C. in a 5% $CO_2$ incubator, the conditioned medium was pooled, centrifuged and the supernatant collected.

C. Purification of EGFL6-Fc Fusion Protein

The conditioned medium (CM) containing the EGFL6-$IgG_4$ fusion protein collected from transiently transfected COS-7 cells (described in B) was stored at −80° C. until processing. Prior to processing, the CM was thawed (630 mL volume), treated with Sigma mammalian protease inhibitor cocktail (Sigma #P8340) at a 1/500 dilution. Subsequently, the CM was filtered through a 0.8 mm Millipore AP25 prefilter, followed by filtration through a 0.2 mm surfactant-free cellulose acetate membrane filter unit (Nalgene).

The starting material (CM) was characterized by Bradford assay for total protein concentration (43.5 μg/mL total protein). The concentration of EGFL6-Fc protein was measured by Western blots and enhanced chemiluminence (0.75 μg/mL) and ELISA (0.52 μg/mL). This analysis indicated that the starting material contained 328 μg of EGFL6-Fc fusion protein (based on ELISA data).

The volume of the filtrate was reduced approximately 21-fold using an Amicon 8400 stir cell equipped with a 76 mm, YM-30 membrane (30K MWCO) at 2–8□C and 50 psi $N^2$. After concentrating, the YM-30 membrane was rinsed with 10 mL of Dulbecco's PBS (D-PBS), and the rinse was added to the retentate. The retentate was filtered through a 0.45 mm filter unit (Pall Acrodisc/low protein binding HT Tuffryn membrane). The recovered volume was 33 mL with a total protein concentration of 663 μg/mL as determined by the Bradford assay.

The recovered volume was further purified with affinity chromatography using a 1 ml, Pharmacia HiTrap Recombinant Protein A Fast Flow column (capacity: 50 mg human IgG/ml drained gel). The column was initially washed with 10 mL of D-PBS. The filtered retentate was loaded onto the column at a flow rate of approximately 0.5 ml/min. The non-bound (flow-through) material was collected and reapplied to the column. Subsequently, the column was washed with 5 ml of D-PBS.

The column was attached to a Pharmacia Akta Explorer 10s chromatograph for elution of bound material. The column was washed at a flow rate of 1 mL/min with 10 ml of PBS pH 7.2 (Gibco), followed by 10 ml of 0.1 M sodium citrate pH 5. Bound material was eluted with 10 ml of 0.1 M glycine pH 2.5, and 0.5 ml fractions were collected during elution. The collected fractions were immediately neutralized with 1 M Hepes pH 8.

The fractions that demonstrated significant absorbance at 280 nm were combined (fractions 23–25=Main Pool; fractions 26–28=Side Pool) and stored at 2–8° C. Insoluble material was observed in each of the pools after overnight refrigeration. The insoluble material in each pool was separated by centrifugation. The supernatant solutions were concentrated using Amicon Microcon-30 (30K MWCO) devices. The pellets were resolubilized in 1 ml of 0.01 M HCl (pH 2).

Portions of the resolubilized material from the Main Pool were alliquoted, pH-adjusted to pH 3, 4, 5, and 6, and stored at 2–8° C. Bradford protein assays, spectrometry at 280 nm, SDS-PAGE/Coomassie Blue R-250 staining, and ELISA assays indicated that the material remained in solution at pH 2 through 4.

To provide material for biological assays, the following fractions were pooled: main pool supernatant solution, main pool resolubilized pellets at pH 2 through 4, side pool supernatant solution and side pool resolubilized pellet. The soluble, pooled material was concentrated using an Amicon Microcon-30 device. The concentrated material was buffer exchanged into 0.1 M glycine pH 3.5 using the same Microcon-30 device. The Microcon-30 membrane was rinsed with 100 ml of 0.1 M glycine pH 3.5 buffer, and this rinse was added to the concentrate. The total volume of concentrate at this point was 110 ml.

The level of EGFL6-Fc protein contained in the concentrate was analyzed by ELISA (11.9 μg/mL EGFL6-IgG). The ELISA assay indicated the total yield of purified EGFL6-Fc protein was 1.3 μg EGFL6-Fc. The level of EGFL6-Fc was also determined by SDS-PAGE/Coomassie Blue R-250 staining (47 μg/mL EGFL6-Fc). The SDS-PAGE analysis indicated that the concentrate of EGFL6-Fc was 61% pure.

7.11 Example 11

Biological Activity of Recombinant EGFL6-Fc Fusion Protein

Various cell lines were treated with recombinant EGFL6-Fc at increasing concentrations (0, 0.6, 1.25, 2.5, 5, 7.5 ng/ml) for 72 hours in media containing 0.1% fetal bovine serum. Cell growth was determined by a colormetric dye celltiter96 assay according to the manufacturer's instructions (Promega). This colormetric dye labeled viable cells. Recombinant Fc protein (0, 0.625, 1.25, 2.5, 5, 7.5 ng/ml) was used as a negative control and EGF (0, 0.6, 1.25, 2.5, 5, 7.5 ng/ml) was used as a positive control. The following tumor cell lines were tested: A549 (lung adenocarcinoma, ATCC accession no. CCRL-185), MCF-7 (breast carcinoma, ATCC accession no. HTB-26), SK-N-Mc (human brain tumor, ATCC accession no. HTB-10). In addition, normal human lung fibroblasts (HNLF; Clonetics), human umbilical vein endothelial cells (HUVEC, Clonetics) and rat neuronal cells (PC 12, ATCC accession no. CRL-1721) were tested.

These assays indicated that treatment with EGFL6-Fc protein stimulated proliferation of the tumor cells tested (A549, MCF-7 and SK-N-Mc) in a dose-dependent manner. Recombinant Fe protein did not affect cell growth on all cell lines in this assay. These assays confirmed that EGFL6 polypeptide stimulates cell growth as shown in Example 7.

Treatment with EGFL6-Fc also stimulated cell proliferation in HUVEC cells and HNLF cells. Treatment with EGFL6-Fc had no effect on PC12 cell growth, but EGF did stimulate cell growth in these cells in a dose-dependent manner. These results indicate that EGFL-6 mediated growth stimulation is cell-type specific.

7.12 Example 12

Analysis of Integrin Receptor Gene Expression and Proliferation Marker Gene Expression in EGFL6 Expressing Cells Quantitative PCR was used to analyze the expression of integrin receptor genes and the p53 expression EGFL6 expressing cells. Human A549 and human 293 cells (ATCC accession no. CRL-1573) were transfected with the EGFL6 cDNA, as described above in Example 7. Total RNA was isolated from $1\times10^6$ cells using the Qiagen RNeasy mini kit (approximately 2–10 $\mu$g). The isolated RNA was digested with DNase I (Gibco) and transcript expression was quantitated by TAQMAN analysis (ABI). Briefly, total RNA (4 $\mu$g) was used for the reverse-transcription (RT) reaction in total volume of 20 $\mu$l with GIBCO "Superscript First-Strand Synthesis System for RT-PCR" kit according to the manufacturer's instructions. The mixture was incubated at 42° C. for 1 hour. After the incubation, the reaction was diluted with 80 $\mu$l of DEPC-$H_2O$. For the Real-Time PCR reaction, 0.5 $\mu$l of the diluted RT reaction was used with ABI SYBR Green PCR Master Mix reagents in a total reaction volume of 25 $\mu$l. The Real-Time PCR was carried out at 50° C. for 2 minutes, 95° C. for 10 minutes, followed by 40 cycles of 95° C. for 15 seconds, and 60° C. for 1 minute. ELFI$\alpha$ RNA was used as an internal control. Kanamycin RNA was used as standards for quantitation: 50,000 copies/27 cycles and 5000 copies/32 cycles.

Expression of the following intergrin receptor genes was quantitified: $\alpha$3, $\beta$1, and $\beta$4. Expression of EGFL6 in A549 cells abolished expression of these integrin receptor genes. Expression of the EGFL6 gene in 293 cells had no effect on the expression of these integrin receptor genes. Integrins play a role in cell—cell adhesion and therefore, these studies suggest that EGFL6 expression may modulate cellular motility and reduce contact inhibition rendering these cells more anchorage independent. This modulation may enhance the ability for tumor cells to invade and metastasize. For example, intergrin $\beta$1 has been shown to be down-regulated in many tumor tissues (Fung et al., Life Sci. Jul. 14, 2000;67(8):923–36, Manzotti et al., Am J Pathol. 2000 January; 156(1):169–74.)

Expression of the proliferation marker, p53, was also analyzed with qualitative PCR. Expression of EGFL6 in A549 cells down-regulated expression of the p53 gene but EGFL6 expression in 293 cells had no effect on p53 gene expression. In normal cells with damaged DNA, the p53 protein acts as a signal to delay cellular entry into S phase and prohibit the accumulation of cells with damaged DNA. Mutations that cause decreased expressioof the p53 gene or inhibit expression of the p53 gene play a role in tumor progression. Therefore, the down-regulation of the p53 gene in EGFL6 expressing cells further suggests that EGFL6 plays a role in tumor progression.

7.13 Example 13

EGFL6 Expression Increased Tumorgenicity in Soft Agar

Soft agar assays were used to analyze the effect of EGFL6 overexpression on tumor cell tumorgenicity. To form the base agar for these assays, 0.5% agar (Sigma) was melted in F-12K media. 10% FBS was added to the liquid agar and the mixture was allowed to cool to 40° C. in a water bath for at least 30 minutes. Subsequently, 1.5 ml of the mixture was poured into each well of a six-well tissue culture plate. To form the top agar, 0.35% agar was melted in F-12K media and allowed to cool to 40° C. in a water bath. 1% FBS was added to the liquid agar. A549 cells transfected with the EGFL6 gene (A549-EGFL6; as described in Example 7) and wild type A549 cells (wt) were added to the liquid top agar mixture at a concentration of 5000 cell/well. This mixture was poured onto the 6-well plates containing the base agar.

Subsequently, 0.5 ml of F-12K medium containing either rEGFL6-Fc (0, 5, and 10 ng/ml) or rEGF (0, 5, and 10 ng/ml) was layered over the cells. The plates were incubated at 37° C. in a humidified environment for 14–25 days. To visualize the cellular colonies, the cells were stained with crystal-violet (0.1%) for 15 minutes and wash extensively with 2 ml of PBS. The stained colonies were counted under a light microscope. The results are summarized in Table 2 below after 14 days incubation.

TABLE 2

NUMBER OF COLONIES FORMED IN SOFT AGAR

| Cell Type | Well #1 | Well #2 |
|---|---|---|
| wt A549 alone | 2 | 1 |
| A549-EGFL6 alone | 140 | 148 |
| A549-EGFL6 + 5 ng/ml EGFL6-Fc | 187 | 190 |
| A549-EGFL6 + 10 ng/ml EGFL6-Fc | 153 | 151 |

Wild type A549 cells formed few colonies in soft agar after 14 days, while they normally form colonies within 21–25 days. In addition, EGF is known to increase the number of colonies formed in soft agar by A549 cells after 21–25 days. A549 cells transfected with the EGFL6 gene formed colonies in soft agar after 14 days. Further, the addition of 5 ng/ml of recombinant EGFL6-Fc fusion protein increased the number of colonies formed within the 14 day period. These assays demonstrate that over-expression of EGFL6 increased the tumorgenicity of the tumor cells.

7.14 Example 14

EGFL6 was Detected on the Cell Surface

To demonstrate that EGFL6 is a secreted protein, Western blot analysis was carried out on conditioned media harvested from cells expressing EGFL6 polypeptide. Human 293 cells were stably transfected with a vector containing a c-terminal myc-tagged EGFL6 cDNA using FuGene reagent (Roche) according to the manufacturer's instructions. The resulting EGFL6-expressing cells were isolated, resuspended in DMEM supplemented with 3% fetal bovine serum and seeded into 6 well petri dishes. The conditioned medium was harvested on days 1–3 after seeding and analyzed by Western blot using standard techniques. Specifically, the conditioned medium was run on a 10% SDS-PAGE gel. The gel was transferred to a nitrocellulose membrane and blotted with an anti-Myc antibody (Invitrogen) diluted at 1:5000. EGFL6 protein was detected as a 68 kD band in the conditioned medium after two days of culture, indicating EGFL6 is a secreted protein.

In addition, the EGFL6 protein was detected on the surface of live cells using fluorescent activated cell sorting (FACS). Human 293 cells were stably transfected with a vector containing the EGFL6 cDNA. FACS analysis was carried out on cells transfected with EGFL6 cDNA or wild type in the presence or absence of an anti-EGFL6 primary polyclonal antibody generated against the peptide QDREDDFDWNPADR (SEQ ID NO: 33) which corresponds to residues 413–426 of SEQ ID NO: 19. Binding of the primary antibody was detected with anti-rabbit FITC secondary antibody. Controls were carried out using secondary antibody alone on both wild type 293 cells and EGFL6 transfected cells. Results showed that the anti-EGFL6 antibody bound to the EGFL6-expressing cells but not wild type cells, indicating EGFL6 was present on the cell surface after expression and was detectable using an antibody.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

---

What is claimed is:

1. A method of detecting a cancerous cell selected from the group consisting of a brain cancer, prostate cancer, skin cancer, lymphoma, sarcoma, colon cancer, pancreatic cancer, and leukemia cell-expressing the polynucleotide of SEQ ID NO: 23 in a biological sample, comprising a) containing the sample with a labeled polynucleotide complementary to said polynucleotide of SEQ ID NO: 23 or a fragment of SEQ ID NO: 23 selected from the group consisting of nucleotides 268 to 1866 and nucleotides 1 to 1366 for a period sufficient to form a complex;

b) detecting the complex, so that if a complex is detected it indicates the expression of polynucleotide of SEQ ID NO: 23 in the cancerous cell; and c) comparing said expression to normal, control samples.

2. The method of claim 1, wherein the biological sample is selected from the group consisting of tissue, cell, blood, serum, lymphatic fluid, and prostatic fluid.

3. The method of claim 1 wherein the labeled polynucleotide comprises a radioisotope, affinity label, enzymatic label or fluorescent label.

* * * * *